(12) United States Patent
MacPhee et al.

(10) Patent No.: US 6,908,591 B2
(45) Date of Patent: Jun. 21, 2005

(54) METHODS FOR STERILIZING BIOLOGICAL MATERIALS BY IRRADIATION OVER A TEMPERATURE GRADIENT

(75) Inventors: Martin MacPhee, Montgomery Village, MD (US); Glenn Calvert, Frederick, MD (US); Tom Lynch, Rockville, MD (US); Randall S. Kent, Thousand Oaks, CA (US); David Mann, Gaithersburg, MD (US); Wilson Burgess, Clifton, VA (US); Shirley Miekka, Gaithersburg, MD (US); William N. Drohan, Springfield, VA (US)

(73) Assignee: Clearant, Inc., Los Angeles, CA (US)

( * ) Notice: Subject to any disclaimer, the term of this patent is extended or adjusted under 35 U.S.C. 154(b) by 127 days.

(21) Appl. No.: 10/197,249

(22) Filed: Jul. 18, 2002

(65) Prior Publication Data

US 2004/0033160 A1 Feb. 19, 2004

(51) Int. Cl.$^7$ ................................. A61L 2/08
(52) U.S. Cl. ........................... 422/22; 422/21; 422/23; 422/24; 435/1.1; 435/2
(58) Field of Search ............................. 422/21, 22, 24, 422/23; 435/1.1, 2

(56) References Cited

U.S. PATENT DOCUMENTS

| | | |
|---|---|---|
| RE23,195 E | 2/1950 | Brasch |
| 2,832,689 A | 4/1958 | Proctor et al. |
| 2,920,969 A | 1/1960 | Stoddard |
| 2,962,380 A | 11/1960 | Wertheim |
| 3,620,944 A | 11/1971 | Tanito |
| 3,743,480 A | 7/1973 | Falk |
| 3,779,706 A | 12/1973 | Nablo |
| 3,962,038 A | 6/1976 | Kawashima et al. .......... 195/68 |
| 4,136,094 A | 1/1979 | Condie |
| 4,251,437 A | 2/1981 | Rasmussen et al. |
| 4,282,863 A | 8/1981 | Beigler et al. |
| 4,330,626 A | 5/1982 | Blair et al. |
| 4,336,247 A | 6/1982 | Eriksen |
| 4,370,264 A | 1/1983 | Kotitschke et al. |
| 4,409,105 A | 10/1983 | Hayashi et al. |
| 4,472,840 A | 9/1984 | Jefferies |
| 4,620,908 A | 11/1986 | Van Duzer |
| 4,727,027 A | 2/1988 | Wiesehahn et al. ......... 435/173 |
| 4,784,850 A | 11/1988 | Abraham |
| 4,798,611 A | 1/1989 | Freeman, Jr. |
| 4,865,602 A | 9/1989 | Smestad et al. |
| 4,894,253 A | 1/1990 | Heineman et al. ............. 427/36 |
| 4,931,361 A | 6/1990 | Baldeschwieler et al. |
| 4,933,145 A | 6/1990 | Uchida et al. |
| 4,946,648 A | 8/1990 | Dichtelmüller et al. |
| 4,963,356 A | 10/1990 | Calenoff et al. |
| 4,994,237 A | 2/1991 | Login et al. ................... 422/21 |
| 5,000,951 A | 3/1991 | Bass et al. |
| 5,002,766 A | 3/1991 | Ransberger et al. ....... 424/94.2 |
| 5,012,503 A | 4/1991 | Nambu et al. |
| 5,044,091 A | 9/1991 | Ueda et al. |
| 5,106,619 A | 4/1992 | Wiesehahn et al. |
| 5,134,295 A | 7/1992 | Wälischmiller |
| 5,185,371 A | 2/1993 | Rubinstein |
| 5,226,065 A | 7/1993 | Held et al. |
| 5,283,034 A | 2/1994 | Okrongly et al. |
| 5,362,442 A | 11/1994 | Kent |
| 5,418,130 A | 5/1995 | Platz et al. |
| 5,460,962 A | 10/1995 | Kemp |
| 5,510,122 A | 4/1996 | Sreebny et al. |
| 5,548,066 A | 8/1996 | Leneau et al. |
| 5,603,894 A | 2/1997 | Aikus et al. |
| 5,609,864 A | 3/1997 | Shanbrom |
| 5,637,451 A | 6/1997 | Ben-Hur et al. |
| 5,643,464 A | 7/1997 | Rhee et al. |
| 5,712,086 A | 1/1998 | Horowitz et al. |
| 5,730,933 A | 3/1998 | Peterson |
| 5,817,528 A | 10/1998 | Bohm et al. |
| 5,837,313 A | 11/1998 | Ding et al. |
| 5,856,172 A | 1/1999 | Greenwood et al. |
| 5,881,534 A | 3/1999 | Ahlqvist et al. |
| 5,911,951 A | 6/1999 | Girardot et al. .............. 422/28 |
| 5,958,669 A | 9/1999 | Ogle et al. .................... 435/1.1 |
| 5,965,349 A | 10/1999 | Lin et al. ......................... 435/2 |
| 5,981,163 A | 11/1999 | Horowitz et al. |
| 5,986,168 A | 11/1999 | Noishiki |
| 5,989,498 A | 11/1999 | Odland |
| 6,010,719 A | 1/2000 | Remon et al. |
| 6,046,024 A | 4/2000 | Burton et al. |
| 6,049,025 A | 4/2000 | Stone et al. |

(Continued)

FOREIGN PATENT DOCUMENTS

| | | |
|---|---|---|
| CA | 2056619 | 10/1991 |
| EP | 310 316 | 4/1989 |
| EP | 334 679 | 9/1989 |

(Continued)

OTHER PUBLICATIONS

Zabal, O. et al. Abstract of"Contamination of fetal bovine serum with bovine viral diarrhea virus," Revista Argentina de Microbiologia, (2000) vol.32, No. 1, pp. 27–32.*
Salim–Hanna et al. Abstract of "Free radical scavenging activity of carnosine," Free radical research communications, (1991) 14 (4), pp. 263–270.*
Robert J. Woods, "Food Irradiation," Endeavor, New Series, vol. 18, No. 3, 1994, pp. 104–108.

(Continued)

Primary Examiner—Elizabeth McKane
(74) Attorney, Agent, or Firm—Morgan, Lewis & Bockius LLP

(57) ABSTRACT

Methods are disclosed for sterilizing tissue to reduce the level of one or more active biological contaminants or pathogens therein, such as viruses, bacteria, (including inter- and intracellular bacteria, such as mycoplasmas, ureaplasmas, nanobacteria, *chlamydia*, rickettsias), yeasts, molds, fungi, spores, prions or similar agents responsible, alone or in combination, for TSEs and/or single or multi-cellular parasites. The methods involve sterilizing one or more tissues with irradiation.

50 Claims, 2 Drawing Sheets

U.S. PATENT DOCUMENTS

| | | | |
|---|---|---|---|
| 6,060,233 A | 5/2000 | Wiggins | |
| 6,066,626 A | 5/2000 | Yew et al. | |
| 6,087,141 A | 7/2000 | Margolis-Nunno et al. | |
| 6,120,592 A | 9/2000 | Brault et al. | |
| 6,159,490 A | 12/2000 | Deghenghi | |
| 6,171,549 B1 | 1/2001 | Kent | |
| 6,187,572 B1 | 2/2001 | Platz et al. | |
| 6,190,855 B1 | 2/2001 | Herman et al. | |
| 6,197,207 B1 | 3/2001 | Chapman et al. | |
| 6,203,544 B1 | 3/2001 | Gotzen | |
| 6,214,534 B1 | 4/2001 | Horowitz et al. | |
| 6,235,508 B1 | 5/2001 | Sowemimo-Coker et al. | |
| 6,258,821 B1 | 7/2001 | Stogniew et al. | |
| 6,312,931 B1 | 11/2001 | O'Dwyer et al. | 435/173.1 |
| 6,346,216 B1 | 2/2002 | Kent | 422/22 |
| 6,358,284 B1 | 3/2002 | Fearnot et al. | 623/23.72 |
| 6,375,989 B1 | 4/2002 | Badylak et al. | 424/551 |
| 6,383,732 B1 | 5/2002 | Stone | 435/1.1 |
| 6,384,419 B1 | 5/2002 | Purtle | 250/526 |
| 6,461,630 B1 | 10/2002 | Tucker et al. | 424/423 |
| 6,485,723 B1 | 11/2002 | Badylak et al. | 424/93.7 |
| 6,548,242 B2 | 4/2003 | Horowitz et al. | 435/2 |
| 2002/0064807 A1 | 5/2002 | Badylak et al. | 435/34 |
| 2002/0068267 A1 | 6/2002 | Horowitz et al. | 435/2 |
| 2002/0106394 A1 | 8/2002 | Tucker et al. | 424/423 |
| 2002/0188319 A1 | 12/2002 | Morris et al. | 606/213 |
| 2003/0068815 A1 | 4/2003 | Stone et al. | 435/325 |

FOREIGN PATENT DOCUMENTS

| | | |
|---|---|---|
| EP | 919 198 A2 | 6/1999 |
| EP | 919 198 A3 | 6/1999 |
| EP | 0808167 B1 | 6/2002 |
| EP | 0820301 B1 | 7/2002 |
| JP | 408098688 A | 4/1996 |
| JP | 11-216147 | 8/1999 |
| RU | 1321420 A | 7/1987 |
| WO | WO 90/00907 | 2/1990 |
| WO | WO 91/16060 | 10/1991 |
| WO | WO 95/03071 | 2/1995 |
| WO | WO 00/25839 | 3/2000 |
| WO | WO 00/28552 | 5/2000 |
| WO | WO 00/52031 | 9/2000 |
| WO | WO 01/08611 A1 | 2/2001 |
| WO | WO 01/12318 A1 | 2/2001 |
| WO | WO 01/32107 A2 | 5/2001 |
| WO | WO 01/32110 A2 | 5/2001 |
| WO | WO 01/45720 A1 | 6/2001 |
| WO | WO 01/49219 A1 | 7/2001 |
| WO | WO 01/72233 A1 | 10/2001 |
| WO | WO 01/72244 A1 | 10/2001 |
| WO | WO 01/91818 A1 | 12/2001 |

OTHER PUBLICATIONS

A. Dziedzic–Goclawska et al., "Sterilisation of Tissue Allografts," Advances in Tissue Banking, vol. 1, pp. 261–321, prior art.

P.V. Kapanin et al., "Feasibility of liposome cryoradiation sterilization," Khimiko–Farmatsevticheskii Zhurnal, 1988, vol. 22(4), Abstract, pp. 479–482.

AABB FDA Liaison Meeting, ABC Newsletter, p. 14 (Dec. 12, 1997).

Alladine, M.F. et al., γ–Radiation Damage to Starr–Edwards Valves, The Lancet, 1:594 (1968).

Alper, T. et al., Protection by Anoxia of the Scrapie Agent and some DNA and RNA Viruses Irradiated as Dry Preparations, J. Gen. Virol., 3:157–166 (1968).

Alper, T. et al., Does the Agent of Scrapie Replicate Without Nucleic Acid?, Nature, 214:764–766 (1967).

Alper, T. et al., The Exceptionally Small Size of the Scrapie Agent, Biochemical and Biophysical Research Communications, 22:278–284 (1966).

Alper, T. et al., The Scrapie Agent: Evidence Against its Dependence For Replication on Intrinsic Nucleic Acid, J. Gen. Virol., 41:503–516 (1978).

Akkus, O. et al., Fracture Resistance of Gamma Radiation Sterilized Cortical Bone Allografts, J. Orthapaedic Research, 19:927–934 (2001) (Elsevier Science Ltd.).

Aparicio, S.R. et al., Light and Electron Microscopy Studies on Homograft and Heterograft Heart Valves, J. Path., 115:147–162 (1975).

Baksa, J. et al., The Use of Pig's Skin (xenograft) for the Treatment of Burns, Magyar Traumatologia, 19:138–145 (1976).

Baldwin, M.L. et al., Irradiation of Blood Components, pp. 10–78 (1992) (American Association of Blood Banks).

Baquey, C. et al., Radiosterilization of Albuminated Polyester Prostheses, Biomaterials, 8:185–189 (1987).

Bassin, R.H. et al., Abrogation of $Fv-1^b$ Restriction With Murine Leukemia Viruses Inactivated by Heat or by Gamma Irradiation, Journal of Virology, 26:306–315 (1978) (American Society for Microbiology).

Beauregard, G. et al., Temperature Dependence of the Radiation Inactivation of Proteins, Analytical Biochemistry, 150:117–120 (1985) (Academic Press Inc.).

Bedrossian Jr., E.H. et al., HIV and Banked Fascia Lata, Ophthalmic Plastic and Reconstructive Surgery, 7:284–288 (1991) (Raven Press Ltd.).

Belov, A.A. et al., The influence of γ–Radiation on Enzyme Activity of Collalitin in the Process of Storage, Radiobiologiia, 30:519–521(1990).

Bingci, L., Mouse Antibody Response Following Repetitive Injections of Gamma–Irradiated Human Placenta Collagen, Chinese Medical Sciences Journal, 9:100–103 (1994).

Blakeslee, S., Lack of Oversight in Tissue Donation Raising Concerns, The New York Times, Late Edition, pp. 1, 22 (Jan. 20, 2002) (http://query.nytimes.com).

Blanchy, B.B. et al., Immobilization of Factor VIII on Collagen Membranes, J. Biomedical Materials Research, 20:469–479 (1986) (John Wiley & Sons, Inc.).

Block, S.S., Disinfection, Sterilization, and Preservation,, Fourth Edition, pp. 31–33 (1991) (Lea & Febiger) (Philadelphia).

Bogers, A.J.J.C. et al., Long–Term Results of the Gamma–Irradiation–Preserved Homograft Monocusp for Transannular Reconstruction of the Right–Ventricular Outflow Tract in Tetralogy of Fallot, Thorac. Cardiovasc. Surgeon, 42:337–339 (1994) (Georg Thieme Verlag Stuttgart).

Borisova, E.A. et al., Protein Degradation During Interphase Death of Thymocytes Induced by Radation and Dexamethasone, Radiobiologiia, 30:517–519 (1990).

Boyer, T.D. et al., Radiation Inactivation of Microsomal Glutathione S–Transferase, The Journal of Biological Chemistry, 261:16963–16968 (1986).

Brown, D.R. et al., Antioxidant Activity Related to Copper Binding of Native Prion Protein, J. Neurochem., 76:69–76 (2001) (Int'l Society for Neurochem.).

Brown, P. et al., The Distribution of Infectivity in Blood Components and Plasma Derivatives in Experimental Models of Transmissible Spongiform Encephalopathy, Transfusion, 38:810–816 (1998).

Brown, P. et al., Effect of Chemicals, Heat and Histopathologic Processing on High–Infectivity Hamster–Adapted Scrapie Virus, J. Infectious Diseases, 145:683–687 (1982) (University of Chicago).

Brown, P. et al., Further Studies of Blood Infectivity in an Experimental Model of Transmissible Spongiform Encephalopathy, With an Explantation of Why Blood Components Do Not Transmit Creutzfeldt–Jakob Disease in Humans, Transfusion, 39:1169–1178 (1999).

Brown, P., The Risk of Blood–Borne Creutzfeldt–Jakob Disease, Advances in Transfusion Safety Dev. Biol., 102:53–59 (1999).

Burwell, R.G., The Fate of Freeze–Dried Bone Allograts, Transplantation Proceedings, 8(Suppl):95–111 (1976).

Callegaro, L. et al., Hollow Fiber Immobilized L–Asparaginase: In Vivo and In Vitro Immunological Studies, The International Journal of Artificial Organs, 6:91–96 (1983) (Wichtig Editore).

Campalani, G. et al., Aortic Valve Replacement With Frozen Irradiated Homografts, Eur. J. Cardio–thorac. Surg., 3:558–561 (1989) (Springer–Verlag).

Campbell, D.G. et al., Sterilization of HIV With Irradiation: Relevance to Infected Bone Allografts, Aust. N.Z. J. Surg., 69:517–521 (1999).

Chanderkar, L.P. et al.., The Involvement of Aromatic Amino Acids in Biological Activity of Bovine Fibrinogen as Assessed by Gamma–Irradiation, Radiation Research, 65:283–291 (1976) (Academic Press, Inc.).

Chanderkar, L.P. et al.., Radiation–Induced Changes In Purified Prothrombin and Thrombin, Biochimica et Biophysica Acta, 706:1–8 (1982) (Elsevier Biomedical Press).

Cheung, D. T. et al., The Effect of γ–Irradiation on Collagen Molecules, Isolated α–chains, and Crosslinked Native Fibers, J. Biomedical Materials Research, 24:581–589 (1990) (John Wiley & Sons, Inc.).

Chin, S. et al., Virucidal Treatment of Blood Protein Products With UVC Radiation, Photochemistry and Photobiology, 65:432–435 (1997) (American Society for Photobiology).

Chuchalin, A.G. et al., Clinical Immunosorbents Basing on Space–Network Polymers, Bioorg Khim, 14:1524–1529 (1988) (Russia).

Cohen, D. J. et al., The Fate of Aortic Valve Homografts 12 to 17 Years After Implantation, Chest, 93:482–484 (1988).

Conrad, E. U. et al., Transmission of the Hepatitis–C Virus by Tissue Transplantation, J. Bone and Joint Surgery, 77–A:214–224 (1995).

Cornu, O. et al., Effect of Freeze–Drying and Gamma Irradiation on the Mechanical Properties of Human Cancellous Bone, J. Orthopaedic Research, 18:426–431 (2000).

Dagli, A. S., Correction of Saddle Nose Deformities by Coral Implantation, Eur. Arch. Otorhinolaryngol., 254:274–276 (1997) (Springer–Verlag).

Defeng et al., Sterilization of Silver–Acidum Pipermedicum Skin for the Treatment of Burns by Radioactive Cobalt–60–.Gamma.–Ray, Radiat. Phys. Chem., 46:4–6 (Caplus Abstract No. 1995:923966) (1995).

De Deyne, P. et al., Some Effects of Gamma Irradiation on Patellar Tendon Allografts, Connective Tissue Research, 27:51–62 (1991) (Gordon and Breach Science Publishers S. A.).

Di Simplicio, P. et al., The Reactivity of the SH Group of Bovine Serum Albumin With Free Radicals, Free Rad. Res. Commsl., 14:253–262 (1991) (Harwood Academic Publishers GmbH).

Donnelly, R.J. et al., Gamma–radiation of Heart Valves at 4°C; A Comparative Study Using Techniques of Histochemistry and Electron and Light Microscopy, Thorax, 28:95–101 (1973).

Dyskin, E.A. et al., Hemomicrocirculatory Bed in the Wall of Hollow Organs of the Dog Gastrointestinal Tract at Portal Hypertension, Arkh Anat Gistol Embiol, 93:58–68 (1987).

Dziedzic–Goclawska, A. et al., Effect of Radiation Sterilization on the Osteoinductive Properties and the Rate of Remodeling of Bone Implants Preserved by Lyophilization and Deep–Freezing, Clinical Orthopaedics and Related Research, 272:30–37 (1991).

Eichler, D.C. et al., Radiation Inactivation Analysis of Enzymes, J. Biological Chemistry, 262:9433–9436 (1987).

Elliot, L.H. et al., Inactivation of Lassa, Marburg and Ebola Viruses by Gamma Irradiation, J. Clinical Microbiology, 16:704–708 (1982) (American Society for Microbiology).

Fideler, B. M. et al., Gamma Irradiation: Effects of Biomechanical Properties of Human Bone–Patellar Tendon–Bone Allografts, American Journal of Sports Medicine, 23:643–646 (1995).

Fidelar, B.M. et al., Effects of Gamma Irradiation on the Human Immunodeficiency Virus, J. Bone and Joint Surgery, 76–A:1032–1035 (1994) (The Journal of Bone and Joint Surgery, Inc.).

Field, E.J. et al., Susceptibility of Scrapie Agent to Ionizing Radiation, Nature, 222:90–91 (1969).

Ghosh, M.M. et al., A Comparison of Methodologies for the Preparation of Human Epidermal–Dermal Composites, Annals of Plastic Surgery; 39:390–404 (1997) (Lippincott–Raven Publishers).

Gibbons, M.J. et al., Effects of Gamma Irradiation on the Initial Mechanical and Material Properties of Goat Bone–Patellar Tendon–Bone Allografts, J. Orthop Res., 9:209–218 (1991) (Orthopaedic Research Society).

Gibbons, J.R.P. et al., Gamma Ray Sterilisation of Homograft Valves, Bulletin De La Societe Internationale De Chirugie, 3:353–358 (1969).

Goertzen, M.J. et al., Anterior Cruciate Ligament Reconstruction Using Cryopreserved Irradiated Bone–ACL–Bone–Allograft Transplants, Knee Surg. Sports Traumatol. Arthroscopy, 2:150–157 (1994) (Springer–Verlag).

Goertzen, M.J. et al., Sterilisation of Canine Anterior Cruciate Allografts by Gamma Irradiation in Argon, J. Bone and Joint Surgery, 77–B:205–212 (1995) (British Editorial Society of Bone and Joint Surgery) (Retracted).

Gregorczyn, S. et al., Strength of Lyophilized and Irradiated Cortical Bone of the Human Femur, Chir. Narz. Ruchu Ortop. Pol., 60:129–133 (1995).

Guidoin, R. et al., A Compound Arterial Prosthesis: The Importance of the Sterilization Procedure on the Healing and Stability of Albuminated Polyester Grafts, Biomaterials, 6:122–128 (1985).

Haig, D.A. et al., Further Studies on the Inactivation of the Scrapie Agent by Ultraviolet Light, J. Gen. Virol, 5:455–457 (1969).

Hehrlein, F. W. et al., Biochemical Changes in Heterologous Aortic Valve Transplants Following Application of Various Sterilization Methods, Langenbecks Arch Chair, 325:1183–1185 (1969).

Hehrlein, F.W. et al., Morphological Studies on Heterologous Heart Valve Transplants Under Various Sterilization Conditions, Thoraxchir vask Chir, 17: 244–251 (1969).

Hernigou, P. et al., Radiation Sterilization of Bone and the HIV Virus, Revue de Chirurgie Orthopédique, 79:445–451 (1993) (Masson, Paris).

Hiemstra, H. et al., Inactivation of Human Immunodeficiency Virus by Gamma Radiation and its Effect on Plasma and Coagulation Factors, Transfusion, 31:32–39 (1991).

Hinton, R. et al., A Biomechanical Analysis of Solvent–dehydrated and Freeze–Dried Human Fascia Lata Allografts, The American Journal of Sports Medicine, 20:607–612 (1992) (Am. Orthopaedic Soc. for Sports Medicine).

Horowitz, B. et al., Inactivation of Viruses in a Labile Blood Derivatives, II. Physical Methods, Transfusion, 25:523–527 (1985).

Horowitz, M., Sterilization of Homograft Ossicles by Gamma Radiation, J. Laryngology and Otology, 93:1087–1089 (1979).

House, C. et al., Inactivation of Viral Agents in Bovine Serum by Gamma Irradiation, Can. J. Microbiol., 36:737–740 (1990).

Hsiue, G. et al., Absorbable Sandwich–Like Membrane for Retinal–Sheet Transplantation, pp. 20–25 (2002) (Wiley Periodicals, Inc).

Ijiri, S. et al., Effect of Sterilization on Bone Morphogenetic Protein, J. Orthopaedic Research, 12:628–636 (1994) (Orthopaedic Research Society).

Imamaliev, A.S. et al., Biological Properties of Bone Tisue Conserved in Plastic Material and Sterilized With Gama Rays, ACTA Chirurgiae Plasticae, 16:129–135 (1974) (Avicenum, zdravotnické nakladatelství).

Ingegneri, A. et al., An 11–Year Assessment of 93 Flash–frozen Homograft Valves in the Aortic Position, Thorac., Cardiovasc. Surgeon, 27:304–307 (1979) (Georg Thieme Verlag Stuttgart).

Jensen, J. et al., Membrane–bound Na, K–ATPase: Target Size and Radiation Inactivation Size of Some of Its Enaymatic Reactions, J. Biological Chemistry, 263:18063–18070 (1988) (Am. Soc. for Biochem. and Mol. Biol.).

Jensen, O. T. et al., Vertical Guided Bone–Graft Augmentation in a New Canine Mandibular Model, The Int'l Journal of Oral and Maxillofacial Implants, 10:335–343 (1995).

Jerosch, J. et al., A New Technique for Bone Sterilization, Biomed. Technik, 34:117–120 (1989).

Jerosch, J. et al., Influence of Different Rehydration Periods on the Stability and the Water Content of Bone Allografts After Lyophilization, Gamma–Irradiation, and Lipid Extraction, Z. Orthop., 132:335–341 (1994) (F. Enke Verlag Stuttgart).

Karnat, H.N. et al., Corrrelation of Structural Alterations in Bovine Fibrinogen with Loss of Clotting Properties After Gamma Irradiation, Radiation Research, 49:381–389 (1972) (Academic Press, Inc.).

Katz, R.W. et al., Radiation –Sterilized Insoluble Collagenous Bone Matrix is a Functional Carrier of Osteogenin for Bone Induction, Calcified Tissue Int., 47:183–185 (1990) (Springer–Verlag New York Inc.).

Keathly, J.D. et al., Is There Life After Irradiation? Part II: Gamma–Irradiated FBS in Cell Culture, BioPharm, (Jul.–Aug.) pp. 46, 50–52 (1993).

Kempner, E.S. et al., Effect of Environmental Conditions on Radiation Target Size Analyses, Analytical Biochemistry, 216:451–455 (1994).

Kempner, E.S. et al., Radiation–Damaged Tyrosinase Molecules are Inactive, Biophysical Journal, 55:159–162 (1989) (Biophysical Society).

Kempner, E.S. et al., Size Determination of Enzymes by Radiation Inactivation, Analytical Biochemistry, 92:2–10 (1979) (Academic Press, Inc.).

Kerboull, L. et al., In Vitro Study of the Influence of Various Conservation Methods on the Mechanical Properties of Patellar Tendon Allografts, Chirurgie, 117:751–762 (1991) (Masson, Paris).

Kitchen, A.D. et al., Effect of Gamma Irradiation on the Human Immunodeficiency Virus and Human Coagulation Proteins, Vox Sang, 56:223–229 (1989) (S. Karger AG, Basel).

Komender, A. et al., Some Biological Properties of Bovine Trypsinized Fascia Xenografts, Archivum Immunologiae et Therapiae Experimentalis, 29:485–489 (1981).

Komendar, A. et al., Some Biological Properties of Preserved Bovine Fascia Enriched With Pulverized Calf Cartilage, Archivum Immunologiae et Therapiae Experimentalis, 32:211–219 (1984).

Kouvalchouk, J.F. et al., The Use of Sterilized Bone Allografts in Reconstruction After Tumour Resection, Revue de Chirurgie Orthopédique, 72:393–401 (1986) (Masson, Paris).

Kuijpers, A.J. et al., In vivo Compatibility and Degradation of Crosslinked Gelatin Gels Incorporated in Knitted Dacron, J. Biomed Mater Res., 51:136–145 (2000) (John Wiley & Sons, Inc.).

Latarjet, R. Inactivation of the Agents of Scrapie, Creutzfeldt–Jakob Disease, and Kuru by Radiations, Slow Transmissible Diseases of the Nervous System, 2:387–407 (1979) (Academic Press, Inc.) (New York).

Latarjet, R. et al., Inactivation of the Scrapie Agent by Near Monochromatic Ultraviolet Light, Nature, 227:1341–1343 (1970).

Lee, D.C. et al., A Direct Relationship Between the Partitioning of the Pathogenic Prion Protein and Transmissible Spongiform Encephalopathy Infectivity During the Purification of Plasma Proteins, Transfusion, 41:449–455 (2001).

Leitman, S. F. Use of Blood Cell Irradiation in the Prevention of Posttransfusion Graft–vs–Host Disease, Transfus. Sci., 10:219–232 (1989).

Le Maire, M. et al., Effects of Ionizing Radiations on Proteins, Journal of Biochem., 267:431–439 (1990).

License Amendment and Procedures for Gamma Irradiation of Blood Products, Dept. of Health & Human Services, Food and Drug Administration, pp. 1–18 (Jun. 22, 1993).

Linberg, J.V. et al., Preserved Irradiated Homologous Cartilage For Orbital Reconstruction, Ophthalmic Surgery, 11:457–462 (1980).

Lüssi–Schlatter, B. et al., Antimicrobial Treatment of Enzyme Preparations With Gamma Rays, Pharm Acta Helv, 49:66–75 (1974).

McDowell, S., Irradiated Cartilage, Plastic Surgical Nursing, pp. 14–15 (Spring 1988).

Ma, J.T. et al., Functional Size Analysis of F–ATPase from *Escherichia coli* by Radiation Inactivation, The Journal of Biological Chemistry, 268:10802–10807 (1993) (The Am. Soc. for Biochem. and Mol. Bio., Inc.).

Maeda, A. et al., Effects of Solvent Preservation With or Without Gamma Irradiation on the Material Properties of Canine Tendon Allografts, Journal of Orthopaedic Research, 11:181–189 (1993) (Orthopaedic Research Society).

Maeda, A. et al., Solvent–dried and Gamma–irradiated Tendon Allografts in Rats, The Journal of Bone and Joint Surgery, 80–B:731–736 (1998).

Malawski, S. et al., The Use of Dry–Freezed Bone Grafts Sterilized by Gamma Rays in Orthopaedic Surgery, Chir. Narz. Ruchu Ortop. Pol., 34:61–68 (1969).

Malm, J. R. et al., An Evaluation of Aortic Valve Homografts Sterilized by Electron Beam Energy, J. Thoracic and Cardiovascular Surgery, 54:471–477 (1967).

Malm, J.R. et al., Results of Aortic Valve Replacement Utilizing Irradiated Valve Homografts, Ann. N. Y. Acad. Sci., 147:740–747 (1969).

Martindale, The Extra Pharmacopoeia, Glucose, Twenty–ninth Edition, Glucose, p. 1265 (1989) (The Royal Pharmaceutical Society of Great Britain).

Marton, L.S. et al., Disinfection and Inactivation of the Human T. Lymphotropic Virus Type III/Lymphadenopathy–Associated Virus, The Journal of Infectious Diseases, 151:400–403 (1985).

Marx, G. Protecting Fibrinogen with Rutin During UVC Irradiation for Viral Inactivation, Photochemistry and Photobiology, 63:541–546 (1996) (American Society for Photobiology).

The Merck Index, Eleventh Edition, Glucose, pp. 699–700 (1989) (Merck & Co., Inc.).

Miekka, S.I. et al., New Methods for Inactivation of Lipid–enveloped and Non–enveloped Viruses, Haemophilia, 4:402–408 (1998) (Blackwell Science Ltd.).

Moore, G.L. et al., Effects of 4000 Rad. Irradiation on the In Vitro Storage Properties of Packed Red Cells, Final Rept., Pub. in Transfusion, 25:583–585 (1985) (Abstract).

Munting, E. et al., Effect of Sterilization on Osteoinduction, Acta Orthop. Scand., 59:34–38 (1988).

Nagrani, S. et al., The Radiation–Induced Inactivation of External Yeast Invertase in Dilute Aqueous Solution, Int. J. Radiat. Biol., 55:191–200 (1989) (Taylor & Francis Ltd.).

Nakata, K. et al, Reconstruction of the Lateral Ligaments of the Ankle Using Solvent–dried and Gamma–Irradiated Allogeneic Fascia Lata, The Journal of Bone & Joint Surgery, 82–B:579–582 (2000) (British Editorial Society of Bone and Joint Surgery).

Nielsen, M. et al., The Apparent Target Size of Rat Brain Benzodiazepine Receptor, Acetylcholinesterase, and Pyruvate Kinase Is Highly Influenced by Experimental Conditions, The Journal of Biological Chemistry, 263:11900–11906 (1988) (The American Society for Biochemistry and Molecular Biology, Inc.).

Oh, W. et al., Mitral Valve Replacement With Preserved Cadaveric Aortic Homografts, J. Thoracic and Cardiovascular Surgery, 65:712–721 (1973).

Pardo, M.E.M. et al., Clinical Application of Amniotic Membranes on a Patient With Epidermolysis Bullosa, Annals of Transplantation, 4:68–73 (1999).

Parizek, J. et al., Duraplasty With Pretreated Freeze–Dried Sterilized Human Dura Mater, Sbor. vĕd. Prací I.F UK Hrader. Králové., 33:135–143 (1990).

Parizek, J. et al., Ovine Pericardium: A New Material For Duraplasty, J. Neurosurg, 84:508–513 (1996).

Patel, K. M. et al., Effect of Gamma Radiation and Ethylene Oxide on Papain, Indian J. Pharm. Sci., 41:81–83 (1979) (The Indian Pharmaceutical Association).

Pietrucha, K. et al., New Collagen Implant As Dural Substitue, Biomaterials, 12:320–323 (1991) (Butterworth–Heinemann Ltd.).

Plavsic, Z. M. et al., Resistance of Porcine Circovirus to Gamma Irradiation, BioPharm, pp. 32–34, 36 (Apr. 2001).

Polezhaev, L.V. et al., Repair of Cranial Defects With Regenerating Bone in Grafting Gamma–Irradiated Bone Filings, ZH Vopr Neifokhir Im N.N. Burdenko, (6):57–60 (1984).

Pollard, The Effect of Ionizing Radiation on Viruses, pp. 65–67, Chapter 4, prior art.

Potier, M. et al., Radiation Inactivation of Proteins: Temperature–Dependent Inter–Protomeric Energy Transfer in Ox Liver Catalase, Biochem. J., 298:571–574 (1994).

Prolo, D.J. et al., Composite Autogeneic Human Cranioplasty: Frozen Skull Supplemented With Fresh Iliac Corticocancellous Bone, Neurosurgery, 15:846–851 (1984) (The Congress of Neurological Surgeons).

Prolo, D.J. et al., Superior Osteogenesis in Transplanted Allogeneic Canine Skull Following Chemical Sterilization, In Clinical Orthopaedics and Related Research; Section III: Basic Science and Pathology, (168):230–242 (1982) (J.B. Lippincott Co.).

Puolakkainen, P.A. et al., The Effect of Sterilization on Transforming Growth Factor $\beta$ Isolated From Demineralized Human Bone, Transfusion, 33:679–685 (1993).

Quaglio, E. et al., Copper Converts the Cellular Prion Protein into a Protease–resistant Species That Is Distinct from the Scrapie Isoform, J. Biological Chemistry, 276:11432–11438 (2001) (The American Society for Biochemistry and Molecular Biology, Inc.).

Raptopoulou–Gigi, M. et al., Antimicrobial Proteins in Sterilised Human Milk, British Medical Journal, 1:12–14 (1977).

Rasmussen, T.J. et al., The Effects of 4 Mrad of $\gamma$ Irradiation on the Initial Mechanical Properties of Bone–Patellar Tendon–Bone Grafts, Arthroscopy: J. Arthroscopic and Related Surgery, 10:188–197 (1994) (Raven Press, Ltd.).

Reid, B.D., The Sterways Process: a New Approach to Inactivating Viruses Using Gamma Radiation, Biologicals, 26:125–130 (1998) (The Int'l Assoc. of Biological Standardization).

Ripamonti, U. et al., Long–Term Evaluation of Bone Formation by Osteogenic Protein 1 in the Baboon and Relative Efficacy of Bone–Derived Bone Morphogenetic Proteins Delivered by Irradiated Xenogeneic Collagenous Matrices, J. Bone and Mineral Research, 15:1798–1809 (2000) (Am. Soc. for Bone and Mineral Res.).

Rittenhouse, E. A. et al., Sterilization of Aortic Valve Grafts for Transplantation, Archives of Surgery, 101:1–5 (1970).

Roe, S.C. et al., The Effect of Gamma Irradiation on Xenograft Tendon Bioprosthesis, Clinical Materials, 9:149–154 (1992) (Elsevier Science Publishers Ltd.).

Rohwer, R.G., Estimation of Scrapie Nucleic Acid MW from Standard Curves for Virus Sensitivity to Ionizing Radiation, Nature, 320:381 (1986) (Macmillan Journals Ltd.).

Rohwer, R.G., Scrapie Infectious Agent is Virus–like in Size and Susceptibility to Inactivation, Nature, 308:658–662 (1984).

Rohwer, R.G., The Scrapie Agent: "A Virus by Any Other Name", Current Topics in Microbiology and Immunology, 172:195–232 (1991).

Rohwer, R.G. et al., Scrapie–Virus or Viroid, The Case For a Virus, National Institutes of Neurological and Communicative Disorders and Stroke, NIH, pp. 333–355 (1980).

Rohwer, R.G., Virus–Like Sensitivity of the Scrapie Agent to Heat Inactivation, Science, 223:600–602 (1984) (American Association for the Advancement of Science).

Sakai, T. et al., Microbiological Studies on Drugs and Their Raw Materials. IV.[1)] Sterilization of Microbial Contaminants in Enzyme Powder by Gamma Irradiation, Chem. Pharm. Bull., 26:1130–1134 (1978).

Salehpour, A. et al., Dose–Dependent Response of Gamma Irradiation on Mechanical Properties and Related Biochemical Composition of Goat Bone–Patellar Tendon–Bone Allografts, J. Orthopaedic Research, 13:898–906 (1995).

Salim–Hanna, M. et al., Free Radical Scavenging Activity Of Carnosine, Free Rad. Res. Comms., 14:263–270 (1991) (Harwood Academic Publishers GmbH).

Sato, H. et al., Sterilization of Therapeutic Immunoadsorbents by Ionizing Radiation, The International Journal of Artificial Organs, 9:131–136 (1986).

Schwarz, N. et al., Irradiation–sterilization of Rat Bone Matrix Gelatin, Acta Orthop Scand, 59:165–167 (1988).

Shcheglova, S.G. et al., The Effect of the Power of Gamma–Radiation on the Radiation dose in the Sterilization of Drugs, Khim Farm ZH, 18:730–732 (1984) Derwent (Abstract) No. 111469.

Smith, C.W. et al., Mechanical Properties of Tendons: Changes With Sterilization and Preservation, J. Biomechanical Engineering, 118:56–61 (1996) (ASME).

Smith, R.A. et al., Gamma Irradiation of HIV–1, J. Orthopaedic Research, 19:815–819 (2001).

Song, K.B. et al., Effect of Gamma–irradiation on the Physicochemical Properties of Blood Plasma Proteins, 2002 Annual Meeting and Food Expo–Anaheim, California, Session 30C–1, Food and Chemistry: Proteins, (Jun. 2002) (Abstract).

Sullivan, R. et al., Inactivation of Thirty Viruses by Gamma Radiation, Applied Microbiology, 22:61–65 (1971) (American Society for Microbiology).

Sung, H. et al., Effects of Various Chemical Sterilization Methods on the Crosslinking and Enzymatic Degradation Characteristics of an Epoxy–Fixed Biological Tissue, Sterilization of Biological Tissues, J. Biomed. Mater. Res., 37:376–383 (1997) (John Wiley & Sons, Inc.).

Suomela, H., Inactivation of Viruses in Blood and Plasma Products, Transfusion Medicine Reviews, 7:42–57 (1993) (W.B. Saunders Company.).

Toritsuka, Y. et al., Effect of Freeze–Drying or γ–Irradiation on Remodeling of Tendon Allograft in Rat Model, J. Orthopaedic Research, 15:294–300 (1997) (Orthopaedic Research Society).

Tylman, D., Mechanical Character of Liofilized and Sterilized by γ–Rays Bone Tissue, Chirurgia Naradow Ruchu Ortop Pol, 31:229–234 (1966).

Vaida, R.I. et al., Structural–Functional Peculiarities of Myocardial Capillaries After Resecton of the Lungs, Arkn. Anat. Gistol. Embriol., 8:68–73 (1987).

Wangerin, K., et al., Behavior of Differently Sterilized Allogenic Lyophilized Cartilage Implants in Dogs, J. Oral Maxillofac Surg., 45:236–242 (1987).

Welch, W., A Comparative Study of Different Methods of Processing Aortic Homografts, Thorax, 24:746–749 (1969).

White, J.M. et al, Sterilization of Teeth by Gamma Radiation, J. Dent Res., 73:1560–1567 (1994).

Wientroub, S. et al., Influence of Irradiation on the Osteoinductive Potential of Demineralilzed Bone Matrix, Calcified Tissue International, 42:255–260 (1988) (Springer–Verlag New York Inc.).

Wong, B. et al., Copper Refolding of Prion Protein, Biochemical and Biophysical Research Communications, 276:1217–1224 (2000) (Academic Press).

Wong, B. et al., Differential Contribution of Superoxide Dismutase Activity by Prion Proteinin Vivo, Biochemical and Biophysical Research Communications, 273:136–139 (2000) (Academic Press).

Wong, B. et al., Prion Disease: A Loss of Antioxidant Function? Biochemical and Biophysical Research Communications, 275:249–252 (2000) (Academic Press).

Wyatt, D.E. et al., Is there Life After Irradiation? Part I: Inactivation of Biological Contaminants, BioPharm, pp. 34–39 (Jun. 1993).

Yarygina, G.A., Dose Rate Effect on Survival of Microorganisms Used As Test–Cultures in Radiation Sterilization of Medical Products, 9:32–39 (1973) (Radiats Tekh) Caplus Abstract No. 2159557 (1973).

Zhang, Q. et al., Ethylene Oxide Does Not Estinguish the Osteoinductive Capacity of Demineralized Bone, Acta Orthop Scand, 68:104–108 (1997) (Scandinavian University Press).

Zhang, Y. et al., A Comprehensive Study of Physical Parameters, Biomechanical Properties and Statistical Correlations of Iliac Crest Bone Wedges Used in Spinal Fusion Surgery, Spine, 19:304–308 (1994) (J.B. Lippincott Co.).

(Abstract of EP0919198A2 and EP0919198A3 (Delphion–DERABS Abstract #G1999–304614)), prior art.

Website: www.wslfweb.org/docs/dstp2000.dtopdf/19–MD.pdf (Defense Science and Technology Plans, (Feb. 2000) p. 176, Section II, MD.03, U.S. Department of Defense Deputy Under Secretary of Defense (Science and Technology)).

Website: www.usacc.org/ataccc/ppt.html, (Advanced Technology Applications for Combat Casualty Care, 2001 Presentations, US Army Medical Research and Material Command Combat Casualty Care Research Program (2001)).

Website: www.usacc.org/RevisedStepB.html, Bakaltcheva, I. et al., (FY01 Request for Proposals–Intramural–Revised 2, Combat Casualty Care Research Program, (2002)).

Website: www.benvue.com/history/history_content.html, (2002).

Website: www.phase–technologies.com/html/vol.2no1.html, Jennings, T.A., (Glossary of Terms for Lyophilization) (1999).

Website: www.phase–technologies.com/html/vol.1no9.html, Jennings, T.A., (Overview of the Lyophilization Process) (1998).

Website: www.phase–technologies.com/html/vol.1no2.html, Jennings, T.A., (Role of Product Temperature in the Lyophilization Process) (1998).

Website: www.phase–technologies.com/html/vol.2no2.html, Jennings, T.A., (What I Wish I Knew About Lyophilization) (1999).

Website: www.phase–technologies.com/html/vol.1no7.html, Jennings, T.A., (Which Shelf Temperature During Lyophilization?) (1998).

Website: www.phase–technologies.com/html/vol.1no10.html , Jennings, T.A., (Yes, You have no Eutectic) (1998).

* cited by examiner

METHODS FOR STERILIZING BIOLOGICAL MATERIALS BY IRRADIATION OVER A TEMPERATURE GRADIENT

BACKGROUND OF THE INVENTION

1. Field of the Invention

The present invention relates to methods for sterilizing tissue to reduce the level of one or more active biological contaminants or pathogens therein, such as viruses, bacteria (including inter- and intracellular bacteria, such as mycoplasmas, ureaplasmas, nanobacteria, chlamydia, rickettsias), yeasts, molds, fungi, spores, prions or similar agents responsible, alone or in combination, for transmissible spongiform encephalopathies (TSEs) and/or single or multicellular parasites. The present invention particularly relates to methods of sterilizing tissue with irradiation, wherein the tissue may subsequently be used in transplantation to replace diseased and/or otherwise defective tissue in an animal.

2. Background of the Related Art

Many biological materials that are prepared for human, veterinary, diagnostic and/or experimental use may contain unwanted and potentially dangerous biological contaminants or pathogens, such as viruses, bacteria, in both vegetative and spore states, (including inter- and intracellular bacteria, such as mycoplasmas, ureaplasmas, nanobacteria, chlamydia, rickettsias), yeasts, molds, fungi, prions or similar agents responsible, alone or in combination, for TSEs and/or single-cell or multicellular parasites. Consequently, it is of utmost importance that any biological contaminant or pathogen in the biological material be inactivated before the product is used. This is especially critical when the material is to be administered directly to a patient, for example in blood transfusions, blood factor replacement therapy, tissue implants, including organ transplants, and other forms of human and/or other animal therapy corrected or treated by surgical implantation, intravenous, intramuscular or other forms of injection or introduction. This is also critical for the various biological materials that are prepared in media or via the culture of cells, or recombinant cells which contain various types of plasma and/or plasma derivatives or other biologic materials and which may be subject to mycoplasmal, prion, ureaplasmal, bacterial, viral and/or other biological contaminants or pathogens.

Recently, the safety of the widespread practice in orthopedic medicine of using human donor tissue to replace damaged cartilage or tendons has come into question. In fact, Federal investigators started looking into the deaths of three patients in Minnesota following knee surgery and found that some people have contracted severe infections after receiving implanted knee tissue, which appeared to be infected with a type of bacteria, known as Clostridium. Maura Lerner, et al, "Knee Surgery Deaths Turn Focus on Donor Tissue", Star Tribune, Dec. 8, 2001. See also "Septic Arthritis Following Anterior Cruciate Ligament Reconstruction Using Tendon Allografts—Florida and Louisiana, 2000", MMWR Weekly, 50(48):1081–1083 (Dec. 7, 2001).

The tissue in these knee surgery cases was cartilage, which is not sterilized as it is believed such sterilization would damage the implant. Instead, tissue suppliers attempt to provide safe tissue through screening donors, testing for bacteria and applying antibiotic solutions. In fact, many procedures for producing human compatible biological materials have involved methods that screen or test the biological materials for one or more particular biological contaminants or pathogens rather than removal or inactivation of the contaminant(s) or pathogen(s) from the biological material. The typical protocol for disposition of materials that test positive for a biological contaminant or pathogen simply is non-use/discarding of that material. In certain cases, known microbial contaminants may be permitted in the implant material at the time it is harvested from the host organism. Examples of screening procedures for contaminants include testing for a particular virus in human blood and tissues from donors. Such procedures, however, are not always reliable, as evidenced by the death of at least one Minnesota man who received a cartilage implant, and are not able to detect the presence of prions or certain viruses, particularly those present in very low numbers. This reduces the value, certainty, and safety of such tests in view of the consequences associated with a false negative result, which can be life threatening in certain cases, for example in the case of Acquired Immune Deficiency Syndrome (AIDS). Furthermore, in some instances it can take weeks, if not months, to determine whether or not the material is contaminated. Moreover, to date, there is no commercially available, reliable test or assay for identifying prions, ureaplasmas, mycoplasmas, and chlamydia within a biological material that is fully suitable for screening out potential donors or infected material (Advances in Contraception 10(4):309–315(1994)). This serves to heighten the need for an effective means of destroying prions, ureaplasmas, mycoplasmas, chlamydia, etc., within a biological material, while still retaining the desired activity of that material. Therefore, it would be desirable to apply techniques that would kill or inactivate contaminants or pathogens during and/or after manufacturing and/or harvesting the biological material.

The importance of ready availability of effective techniques is apparent regardless of the source of the biological material. All living cells and multi-cellular organisms can be infected with viruses and other pathogens. Thus, the products of unicellular natural or recombinant organisms or tissues virtually always carry a risk of pathogen contamination. In addition to the risk that the producing cells or cell cultures may be infected, the processing of these and other biological materials also creates opportunities for environmental contamination. The risks of infection are more apparent for multicellular natural and recombinant organisms, such as transgenic animals. Interestingly, even products from species as different from humans as transgenic plants carry risks, both due to processing contamination as described above, and from environmental contamination in the growing facilities, which may be contaminated by pathogens from the environment or infected organisms that co-inhabit the facility along with the desired plants. For example, a crop of transgenic corn grown out doors, could be expected to be exposed to rodents such as mice during the growing season. Mice can harbor serious human pathogens such as the frequently fatal Hanta virus. Since these animals would be undetectable in the growing crop, viruses shed by the animals could be carried into the transgenic material at harvest. Indeed, such rodents are notoriously difficult to control, and may gain access to a crop during sowing, growth, harvest or storage. Likewise, contamination from overflying or perching birds has the potential to transmit such serious pathogens as the causative agent for psittacosis. Thus, any biological material, regardless of its source, may harbor serious pathogens that must be removed or inactivated prior to administration of the material to a recipient human or other animal.

In conducting experiments to determine the ability of technologies to inactivate viruses, the actual viruses of concern are seldom utilized. This is a result of safety concerns for the workers conducting the tests, and the difficulty and expense associated with facilities for containment and waste disposal. In their place, model viruses of the same family and class are usually used. In general, it is acknowledged that the most difficult viruses to inactivate are those with an outer shell made up of proteins, and that among these, the most difficult to inactivate are those of the smallest size. This has been shown to be true for gamma irradiation and most other forms of radiation because these viruses' diminutive size is associated with a small genome. The magnitude of direct effects of radiation upon a molecule is directly proportional to the size of the molecule; that is, the larger the target molecule, the greater is the effect. As a corollary, it has been shown for gamma-irradiation that the smaller the viral genome, the higher is the radiation dose required to inactive it Among the viruses of concern for both human and animal-derived biological materials, the smallest, and thus most difficult to inactivate, belong to the family of Parvoviruses and the slightly larger protein-coated Hepatitis virus. In humans, the Parvovirus B19, and Hepatitis A are the agents of concern. In porcine-derived materials, the smallest corresponding virus is Porcine Parvovirus. Since this virus is harmless to humans, it is frequently chosen as a model virus for the human B19 Parvovirus. The demonstration of inactivation of this model parvovirus is considered adequate proof that the method employed will kill human B 19 virus and Hepatitis A, and, by extension, that it will also kill the larger and less hardy viruses, such as HIV, CMV, Hepatitis B, Hepatitis C, and others.

More recent efforts have focused on methods to remove or inactivate contaminants in products intended for use in humans and other animals. Such methods include heat treating, filtration and the addition of chemical inactivants or sensitizers to the product.

According to current standards of the U.S. Food and Drug Administration, heat treatment of biological materials may require heating to approximately 60° C. for a minimum of 10 hours, which can be damaging to sensitive biological materials. Indeed, heat inactivation can destroy 50% or more of the biological activity of certain biological materials. Tissues are particularly sensitive to these high temperature treatments.

Filtration involves filtering the product in order to physically remove contaminants. Unfortunately, this method may also remove products that have a high molecular weight. Further, in certain cases, small viruses may not be removed by the filter.

The procedure of chemical sensitization involves the addition of noxious agents which bind to the DNA/RNA of the virus, and which are activated either by UV or other radiation. This radiation produces reactive intermediates and/or free radicals which bind to the DNA/RNA of the virus, break the chemical bonds in the backbone of the DNA/RNA, and/or cross-link or complex it in such a way that the virus can no longer replicate. This procedure requires that unbound sensitizer be washed from products since the sensitizers are toxic, if not mutagenic or carcinogenic, and cannot be administered to a patient.

Irradiating a product with gamma radiation is another method of sterilizing a product. Gamma radiation is effective in destroying viruses and bacteria when given in high total doses (Keathly, et al., "Is There Life After Irradiation? Part 2," *BioPharm* July–August, 1993, and Leitman, "Use of Blood Cell Irradiation in the Prevention of Post Transfusion Graft-vs-Host Disease," *Transfusion Science* 10:219–239 (1989)). The published literature in this area, however, teaches that gamma radiation can be damaging to radiation sensitive products, such as blood, blood products, tissues, protein and protein-containing products. In particular, it has been shown that high radiation doses are injurious to red blood cells, platelets and granulocytes (Leitman). U.S. Pat. No. 4,620,908 discloses that protein products must be frozen prior to irradiation in order to maintain the viability of the protein product. This patent concludes that "[i]f the gamma irradiation were applied while the protein material was at, for example, ambient temperature, the material would be also completely destroyed, that is the activity of the material would be rendered so low as to be virtually ineffective." Unfortunately, many sensitive biological materials, such as monoclonal antibodies (Mab), may lose viability and activity if subjected to freezing for irradiation purposes and then thawing prior to administration to a patient.

It has recently been reported that federal officials had turned up at least 25 cases of serious bacterial infections in people who received tissue transplants; at least one case resulted in death. (The New York Times, Mar. 15, 2002). In the case resulting in death, the Centers for Disease Control and Prevention in Atlanta found that the tissue that had fatally infected a Minnesotan who was having kneecap repair surgery had not been refrigerated until 19 hours after the donor's death, by which time lethal bacteria from the donor's intestines might have spilled into his body. As noted in the article, gamma irradiation may be used to kill various pathogens. However, according to a representative of the CDC, such irradiation may result in weakened tissue, like cartilage and tendons, used to repair damaged joints. Therefore, there is a recognition in the art of a long felt need for improved methods of sterilizing tissue without deleteriously affecting the tissue. See also, U.S. Pat. Nos. 6,326,018 and 6,203,755.

When the product to be sterilized is biological tissue that is to be transplanted, even greater sensitivity to irradiation or other sterilization methods is often encountered. This greater sensitivity is the result of the molecular integration of the biochemical, physiological, and anatomical systems that is required for normal function of that biological tissue. Thus, special procedures are typically required to maintain the tight molecular integration that underpins normal function during and after transplantation of a biological tissue. Furthermore, special procedures may be required in addition to other considerations, such as histocompatibility (matching of HLA types, etc.) between donor and recipient, and including compatibility between species when there is inter-species (i.e., heterografting) transplantation.

Tissues and organs that may be used in transplantation are numerous. Non-limiting examples include heart, lung, liver, spleen, pancreas, kidney, corneas, bone, joints, bone marrow, blood cells (red blood cells, leucocytes, lymphocytes, platelets, etc.), plasma, skin, fat, tendons, ligaments, hair, muscles, blood vessels (arteries, veins), teeth, gum tissue, fetuses, eggs (fertilized and not fertilized), eye lenses, and even hands. Active research may soon expand this list to permit transplantation of nerve cells, nerves, and other physiologically and anatomically complex tissues, including intestine, cartilage, entire limbs, and portions of brain.

As surgical techniques become more sophisticated, and as storage and preparation techniques improve, the demand for various kinds of transplantation may reasonably be expected to increase over current levels.

Another factor that may feed future transplantation demand is certain poor lifestyle choices in the population, including such factors as poor nutrition (including such trends as the increasing reliance on so-called fast foods and fried foods; insufficient intake of fruits, vegetables and true whole grains; and increased intake of high glycemic, low nutritional value foods, including pastas, breads, white rice, crackers, potato chips and other snack foods, etc.), predilections toward a sedentary lifestyle, and over-exposure to ultraviolet light in tanning booths and to sunlight. The increasing occurrence of such factors as these have resulted, for example, in increased incidences of obesity (which also exacerbates such conditions as arthritis and conditions with cartilage damage, as well as impairs wound healing, immune function, cancer risk, etc.), type II diabetes and polycystic ovary syndrome (high post prandial glucose values causing damage to such tissues as nerve, muscle, kidney, heart, liver, etc., causing tissue and organ damage even in persons who are not diabetic), many cancers, and hypertension and other cardiovascular conditions, such as strokes and Alzheimer's disease (recent data suggesting that Alzheimer's may be the result of a series of mini-strokes). Thus, poor lifestyle choices ultimately will increase demand for bone, cartilage, skin, blood vessels, nerves, and the specific tissues and organs so destroyed or damaged.

Infections comprise yet another factor in transplantation demand. Not only can bacterial and viral infections broadly damage the infected host tissue or organ, but they can also spread vascularly or by lymphatics to cause lymph vessel or vascular inflammation, and/or plaque build up that ultimately results in infarct (for example, stroke, heart attack, damaged or dead tissue in lung or other organ, etc.). In addition, there is an epidemic of infection by intracellular microbes for which reliable commercial tests are not available (for example, mycoplasma, ureaplasma, and *chlamydia*), for example, as a result of sexual contact, coughing, etc. [for example, more than 20% of sore throats in children are due to *chlamydia* (E. Normann, et al., "*Chlamydia* Pneumoniae in Children Undergoing Adenoidectomy," *Acta Paediatrica* 90(2): 126–129(2001))].

Some intravascular infectious agents, via the antibodies that are produced to fight them, result in attack of tissue having surface molecules that have a molecular structure similar to the structure of surface or other groups of the infectious agent. Such is the case with some *Streptococci* infections (antibodies produced against M proteins of *Streptococci* that cross-react with cardiac, joint and other tissues), for example, in which tissue and other cardiac tissue may be attacked to cause reduced cardiac function, and which can result in death if the infection is not properly treated before extensive damage occurs. Another antibody mediated condition that can affect cardiac tissue, among other tissues/cells, is antiphospholipid antibody syndrome (APLA), in which antibodies are directed against certain phospholipids (cardiolipin) to produce a hypercoagulable state, thrombocytopenia, fetal loss, dementia, strokes, optic changes, Addison's disease, and skin rashes, among other symptoms. Tissue vegetations and mitral regurgitation are common in intravascular infections, although tissue destruction so extensive as to require valve replacement is rare.

Other intravascular infectious agents directly attack tissues and organs in/on which they establish colonies. Non-limiting examples include *Staphylococci* (including, for example, *S. aureus, S. epidermidis, S. saprophyticus*, among others), *Chlamydia* (including, for example, *C. pneumoniae*, among others), *Streptococci* (including, for example, the viridians group of *Streptococci: S. sanguis, S. oralis* (mitis), *S. salivarius, S. mutans*, and others; and other species of *Streptococci*, such as *S. bovis* and *S. pyogenes*), *Enterococci* (for example, *E. faecalis* and *E. faecium*, among others), various fungi, and the "HACEK" group of gram-negative bacilli (*Haemophilus parainfluenzae, Haemophilus aphrophilus, Actinibacillus actnomycetemcomitans, Cardiobacterium hominis, Eikenella corrodens*, and *Kingella kingae*), *Neisseria gonorrhoeae, Clostridia* sp., *Listeria moncytogenes, Salmonella* sp., *Bacteroides fragilis, Escherichia coli, Proteus* sp., mycoplasmas, ureaplasmas, various viruses (for example, cytomegalovirus, HIV, and herpes simplex virus), and *Klebsiella-Enterobacter-Serratia* sp., among others.

An exemplary study by Nystrom-Rosander, et al. may be cited for showing the presence of *Chlamydia pneumoniae* in sclerotic tissue that required replacement as a result of the sclerosis. (C. Nystrom-Rosander, et al., "High Incidence of *Chlamydia pneumoniae* in Sclerotic Tissue of Patients Undergoing Aortic Valve Replacement," *Scandinavian Journal of Infectious Disease* 29:361–365 (1997)).

Yet another factor in transplantation demand is drug use, particularly the use of illicit drugs, but also including inappropriate and sometimes illegal use of otherwise licit drugs (such as overuse of alcohol/alcoholism causing cirrhosis of the liver, and therefore requiring liver transplantation). Such drug use often strongly damages or even destroys sensitive tissues and organs such as kidney, liver, lung, heart, brain/nerves, and/or portions thereof. In addition, intravenous drug use greatly increases the odds of contracting intravascular infections by any one or more of the above-cited infectious agents (among many others), which infections can attack virtually any organ or portion thereof, including the tricuspid valve (located between the right atrium and the right ventricle), the mitral valve (located between the left atrium and the left ventricle), the pulmonary or pulmonic valve (located between the right ventricle and the pulmonary artery), and the aortic valve (located between the left ventricle and the aorta) with any infectious agent that may enter through implanted tissue.

In view of the difficulties discussed above, there remains a need for methods of sterilizing biological materials that are effective for reducing the level of active biological contaminants or pathogens without an adverse effect on the material (s).

The above references are incorporated by reference herein where appropriate for appropriate teachings of additional or alternative details, features and/or technical background.

SUMMARY OF THE INVENTION

An object of the invention is to solve at least the related art problems and disadvantages, and to provide at least the advantages described hereinafter.

Accordingly, it is an object of the present invention to provide methods of sterilizing tissue by reducing the level of active biological contaminants or pathogens without adversely affecting the tissue or other material. Other objects, features and advantages of the present invention will be set forth in the detailed description of preferred embodiments that follows, and in part will be apparent from the description or may be learned by practice of the invention. These objects and advantages of the invention will be realized and attained by the compositions and methods particularly pointed out in the written description and claims hereof.

In accordance with these and other objects, a first embodiment of the present invention is directed a method for sterilizing one or more tissues that are sensitive to radiation, the method comprising: (i) adding to the one or more tissues at least one stabilizer; and (ii) irradiating the one or more tissues with radiation for a time effective to sterilize the one or more tissues and at a rate effective to sterilize the one or more tissues, wherein the at least one stabilizer and the rate of irradiation are together effective to protect the one or more tissues from the radiation.

Another embodiment of the present invention is directed to a method for sterilizing one or more tissues that are sensitive to radiation, said method comprising: (i) adding to the one or more tissues at least one cryopreservative; and (ii) irradiating the one or more tissues with radiation for a time effective to sterilize the one or more tissues and at a rate effective to sterilize the one or more tissues.

Another embodiment of the present invention is directed to a method for sterilizing one or more tissues that are sensitive to radiation, said method comprising: (i) adding to the one or more tissues at least one stabilizer; (ii) subjecting the at least one tissue to a treatment effective to enhance penetration of the at least one stabilizer into the one or more tissues; and (iii) irradiating the one or more tissues with radiation for a time effective to sterilize the one or more tissues and at a rate effective to sterilize the one or more tissues wherein said at least one stabilizer and the rate of irradiation are together effective to protect said one or more tissue from said radiation.

Another embodiment of the present invention is directed to a method for sterilizing one or more tissues that are sensitive to radiation, said method comprising: (i) adding to the one or more tissues at least one cryopreservative; (ii) subjecting the one or more tissues to a treatment effective to enhance penetration of the at least one cryopreservative into the one or more tissues; and (iii) irradiating the one or more tissues with radiation for a time effective to sterilize the one or more tissues and at a rate effective to sterilize the one or more tissues.

Another embodiment of the present invention is directed to a composition including one or more tissues and at least one cryopreservative in an amount effective to preserve the one or more tissues for their intended use following sterilization with radiation.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

DETAILED DESCRIPTION OF PREFERRED EMBODIMENTS

A. Definitions

Figure 1:
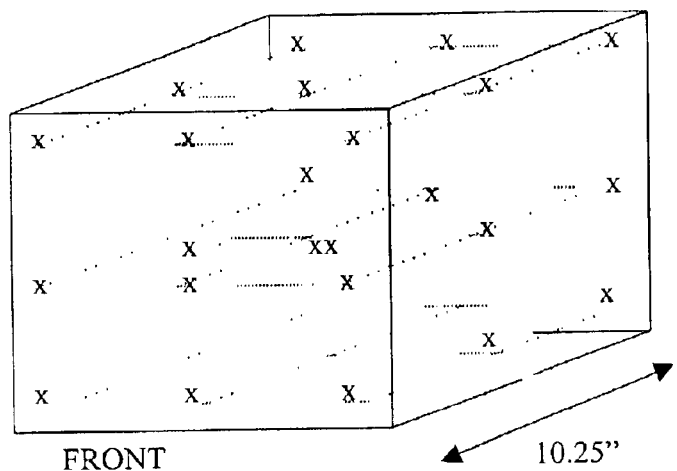
FIG. 1 illustrates the internal thermocouple/dosimeter placement scheme of Example 29 of the present invention.

Unless defined otherwise, all technical and scientific terms used herein are intended to have the same meaning as is commonly understood by one of ordinary skill in the relevant art.

As used herein, the singular forms "a," "an," and "the" include the plural reference unless the context clearly dictates otherwise.

As used herein, the term "sterilize" is intended to mean a reduction in the level of at least one active biological contaminant or pathogen found in the tissue being treated according to the present invention.

As used herein, the term "non-aqueous solvent" is intended to mean any liquid other than water in which a biological material, such as one or more tissues, may be dissolved or suspended or which may be disposed within a biological material, such as one or more tissues, and includes both inorganic solvents and, more preferably, organic solvents. Illustrative examples of suitable non-aqueous solvents include, but are not limited to, the following: alkanes and cycloalkanes, such as pentane, 2-methylbutane (isopentane), heptane, hexane, cyclopentane and cyclohexane; alcohols, such as methanol, ethanol, 2-methoxyethanol, isopropanol, n-butanol, t-butyl alcohol, and octanol; esters, such as ethyl acetate, 2-methoxyethyl acetate, butyl acetate and benzyl benzoate; aromatics, such as benzene, toluene, pyridine, xylene; ethers, such as diethyl ether, 2-ethoxyethyl ether, ethylene glycol dimethyl ether and methyl t-butyl ether; aldehydes, such as formaldehyde and glutaraldehyde; ketones, such as acetone and 3-pentanone (diethyl ketone); glycols, including both monomeric glycols, such as ethylene glycol and propylene glycol, and polymeric glycols, such as polyethylene glycol (PEG) and polypropylene glycol (PPG), e.g., PPG 400, PPG 1200 and PPG 2000; acids and acid anhydrides, such as formic acid, acetic acid, trifluoroacetic acid, phosphoric acid and acetic anhydride; oils, such as cottonseed oil, peanut oil, culture media, polyethylene glycol, poppyseed oil, safflower oil, sesame oil, soybean oil and vegetable oil; amines and amides, such as piperidine, N,N-dimethylacetamide and N,N-deimethylformamide; dimethylsulfoxide (DMSO); nitriles, such as benzonitrile and acetonitrile; hydrazine; detergents, such as polyoxyethylenesorbitan monolaurate (Tween 20) and monooleate (Tween 80), Triton and sodium dodecyl sulfate; carbon disulfide; halogenated solvents, such as dichloromethane, chloroform, carbon tetrachloride, 1,2-dichlorobenzene, 1,2-dichloroethane, tetrachloroethylene and 1-chlorobutane; furans, such as tetrahydrofuran; oxanes, such as 1,4-dioxane; and glycerin/glycerol. Particularly preferred examples of suitable non-aqueous solvents include non-aqueous solvents which also function as stabilizers, such as ethanol and acetone.

As used herein, the term "biological contaminant or pathogen" is intended to mean a biological contaminant or pathogen that, upon direct or indirect contact with a biological material, such as one or more tissues, may have a deleterious effect on the biological material or upon a recipient thereof. Such other biological contaminants or pathogens include the various viruses, bacteria, in both vegetative and spore states, (including inter- and intracellular bacteria, such as mycoplasmas, ureaplasmas, nanobacteria, chlamydia, rickettsias), yeasts, molds, fungi, prions or similar agents responsible, alone or in combination, for TSEs and/or single or multicellular parasites known to those of skill in the art to generally be found in or infect biological materials. Examples of other biological contaminants or pathogens include, but are not limited to, the following: viruses, such as human immunodeficiency viruses and other retroviruses, herpes viruses, filoviruses, circoviruses, paramyxoviruses, cytomegaloviruses, hepatitis viruses (including hepatitis A, B, C, and D variants thereof, among others), pox viruses, toga viruses, Ebstein-Barr viruses and parvoviruses; bacteria, such as *Escherichia, Bacillus, Campylobacter, Streptococcus* and *Staphylococcus*; nanobacteria; parasites, such as *Trypanosoma* and malarial parasites, including *Plasmodium* species; yeasts; molds; fungi; mycoplasmas and ureaplasmas; chlamydia; rickettsias, such as *Coxiella burnetti*; and prions and similar agents responsible, alone or in combination, for one or more of the disease states known as transmissible spongiform encephalopathies (TSEs) in mammals, such as scrapie, transmissible mink encephalopathy, chronic wasting disease (generally observed in mule deer and elk), feline spongiform encephalopathy, bovine spongiform encephalopathy (mad cow disease), Creutzfeld-Jakob disease (including variant CJD), Fatal Familial Insomnia, Gerstmann-Straeussler-Scheinker syndrome, kuru and Alpers syndrome. As used herein, the term "active biological contaminant or pathogen" is intended to mean a biological contaminant or pathogen that is capable of causing a deleterious effect, either alone or in combination with another factor, such as a second biological contaminant or pathogen or a native protein (wildtype or mutant) or antibody, in a biological material, such as one or more tissues, and/or a recipient thereof.

As used herein, the term "a biologically compatible solution" is intended to mean a solution to which a biological material, such as one or more tissues, may be exposed, such as by being suspended or dissolved therein, and retain its essential biological and physiological characteristics. Such solutions may be of any suitable pH, tonicity, concentration and/or ionic strength.

As used herein, the term "a biologically compatible buffered solution" is intended to mean a biologically compatible solution having a pH and osmotic properties (e.g., tonicity, osmolality and/or oncotic pressure) suitable for maintaining the integrity of the material(s) therein, such as one or more tissues. Suitable biologically compatible buffered solutions typically have a pH between 2 and 8.5 and are isotonic or only moderately hypotonic or hypertonic. Biologically compatible buffered solutions are known and readily available to those of skill in the art. Greater or lesser pH and/or tonicity may also be used in certain applications. The ionic strength of the solution may be high or low, but is typically similar to the environments in which the tissue is intended to be used.

As used herein, the term "stabilizer" is intended to mean a compound or material that, alone and/or in combination, reduces damage to one or more tissues being irradiated to a level that is insufficient to preclude the safe and effective use of the material. Illustrative examples of stabilizers that are suitable for use include, but are not limited to, the following, including structural analogs and derivatives thereof: antioxidants; free radical scavengers, including spin traps, such as tert-butyl-nitrosobutane (tNB), a-phenyl-tert-butylnitrone (PBN), 5,5-dimethylpyrroline-N-oxide (DMPO), tert-butylnitrosobenzene (BNB), a-(4-pyridyl-1-oxide)-N-tert-butylnitrone (4-POBN) and 3,5-dibromo-4-nitroso-benzenesulphonic acid (DBNBS); combination stabilizers, i.e., stabilizers which are effective at quenching both Type I and Type II photodynamic reactions; and ligands, ligand analogs, substrates, substrate analogs, modulators, modulator analogs, stereoisomers, inhibitors, and inhibitor analogs, such as heparin, that stabilize the molecule(s) to which they bind. Preferred examples of additional stabilizers include, but are not limited to, the following: fatty acids, including 6,8-dimercapto-octanoic acid (lipoic acid) and its derivatives and analogues (alpha, beta, dihydro, bisno and tetranor lipoic acid), thioctic acid, 6,8-dimercapto-octanoic acid, dihydrolopoate (DL-6,8-dithioloctanoic acid methyl ester), lipoamide, bisonor methyl ester and tetranor-dihydrolipoic acid, omega-3 fatty acids, omega-6 fatty acids, omega-9 fatty acids, furan fatty acids, oleic, linoleic, linolenic, arachidonic, eicosapentaenoic (EPA), docosahexaenoic (DHA), and palmitic acids and their salts and derivatives; carotenes, including alpha-, beta-, and gamma-carotenes; Co-Q10; xanthophylls; sucrose, polyhydric alcohols, such as glycerol, mannitol, inositol, and sorbitol; sugars, including derivatives and stereoisomers thereof, such as xylose, glucose, ribose, mannose, fructose, erythrose, threose, idose, arabinose, lyxose, galactose, allose, altrose, gulose, talose, and trehalose; amino acids and derivatives thereof, including both D- and L-forms and mixtures thereof, such as arginine, lysine, alanine, valine, leucine, isoleucine, proline, phenylalanine, glycine, serine, threonine, tyrosine, asparagine, glutamine, aspartic acid, histidine, N-acetylcysteine (NAC), glutamic acid, tryptophan, sodium capryl N-acetyl tryptophan, and methionine; azides, such as sodium azide; enzymes, such as Superoxide Dismutase (SOD), Catalase, and $\Delta 4$, $\Delta 5$ and $\Delta 6$ desaturases; uric acid and its derivatives, such as 1,3-dimethyluric acid and dimethylthiourea; allopurinol; thiols, such as glutathione and reduced glutathione and cysteine; trace elements, such as selenium, chromium, and boron; vitamins, including their precursors and derivatives, such as vitamin A, vitamin C (including its derivatives and salts such as sodium ascorbate and palmitoyl ascorbic acid) and vitamin E (and its derivatives and salts such as alpha-, beta-, gamma-, delta-, epsilon-, zeta-, and eta-tocopherols, tocopherol acetate and alpha-tocotrienol); chromanol-alpha-C6; 6-hydroxy-2,5,7,8-tetramethylchroma-2 carboxylic acid (Trolox) and derivatives; extraneous proteins, such as gelatin and albumin; tris-3-methyl-1-phenyl-2-pyrazolin-5-one (MCI-186); citiolone; puercetin; chrysin; dimethyl sulfoxide (DMSO); piperazine diethanesulfonic acid (PIPES); imidazole; methoxypsoralen (MOPS); 1,2-dithiane-4,5-diol; reducing substances, such as butylated hydroxyanisole (BHA) and butylated hydroxytoluene (BHT); cholesterol, including derivatives and its various oxidized and reduced forms thereof, such as low density lipoprotein (LDL), high density lipoprotein (HDL), and very low density lipoprotein (VLDL); probucol; indole derivatives; thimerosal; lazaroid and tirilazad mesylate; proanthenols; proanthocyanidins; ammonium sulfate; Pegorgotein (PEG-SOD); N-tert-butyl-alpha-phenylnitrone (PBN); 4-hydroxy-2,2,6,6-tetramethylpiperidin-1-oxyl (Tempol); mixtures of ascorbate, urate and Trolox C (Asc/urate/Trolox C); proteins, such as albumin, and peptides of two or more amino acids, any of which may be either naturally occurring amino acids, i.e., L-amino acids, or non-naturally occurring amino acids, i.e., D-amino acids, and mixtures, derivatives, and analogs thereof, including, but not limited to, arginine, lysine, alanine, valine, leucine, isoleucine, proline, phenylalanine, glycine, histidine, glutamic acid, tryptophan (Trp), serine, threonine, tyrosine, asparagine, glutamine, aspartic acid, cysteine, methionine, and derivatives thereof, such as N-acetylcysteine (NAC) and sodium capryl N-acetyl tryptophan, as well as homologous dipeptide stabilizers (composed of two identical amino acids), including such naturally occurring amino acids, as Gly-Gly (glycylglycine) and Trp-Trp, and heterologous dipeptide stabilizers (composed of different amino acids), such as camosine ($\beta$-alanyl-histidine), anserine ($\beta$-alanyl-methylhistidine), and Gly-Trp; and flavonoids/flavonols, such as diosmin, quercetin, rutin, silybin, silidianin, silicristin, silymarin, apigenin, apiin, chrysin, morin, isoflavone, flavoxate, gossypetin, myricetin, biacalein, kaempferol, curcumin, proanthocyanidin B2-3-O-gallate, epicatechin gallate, epigallocatechin gallate, epigallocatechin, gallic acid, epicatechin, dihydroquercetin, quercetin chalcone, 4,4'- dihydroxy-chalcone, isoliquiritigenin, phloretin, coumestrol, 4',7-dihydroxy-flavanone, 4',5-dihydroxyflavone, 4',6-dihydroxy-flavone, luteolin, galangin, equol, biochanin A, daidzein, formononetin, genistein, amentoflavone, bilobetin, taxifolin, delphinidin, malvidin, petunidin, pelargonidin, malonylapiin, pinosylvin, 3-methoxyapigenin, leucodelphinidin, dihydrokaempferol, apigenin 7-O-glucoside, pycnogenol, aminoflavone, purpurogallin fisetin, 2',3'-dihydroxyflavone, 3-hydroxyflavone, 3',4'-dihydroxyflavone, catechin, 7-flavonoxyacetic acid ethyl ester, catechin, hesperidin, and naringin. Particularly preferred examples include single stabilizers or combinations of stabilizers that are effective at quenching both Type I and Type II photodynamic reactions, and volatile stabilizers, which can be applied as a gas and/or easily removed by evaporation, low pressure, and similar methods. Additional preferred examples for use in the methods of the present invention include hydrophobic stabilizers. Stabilizers may also act as cryopreservatives.

As used herein, the term "cryopreservative" is intended to mean a compound or material that, alone and/or in combination, protects the one or more tissues being irradiated during cooling or freezing. Illustrative examples of cryopreservatives include, but are not limited to, chondroitin sulfate, glycosaminoglycan dimethylsulfoxide, cell penetrating organic solutes, polysaccharides, glycerol, Dulbecco's minimum essential medium (DMEM), glutamine, D-glucose, sodium pyruvate, fetal calf serum, papaverine, DMSO, glycerol, trehalose, $KH_2PO_4$, $K_2HPO_4$, KCl, mannitol, $NaHCO_3$, sodium ascorbate, 1,2-propanediol, formamide, 2,3-butanediol, probuchol, curcumin and mixtures thereof. Cryopreservatives may also act as stabilizers.

As used herein, the term "residual solvent content" is intended to mean the amount or proportion of freely-available liquid in the biological material. Freely-available liquid means the liquid, such as water and/or an organic solvent (e.g., ethanol, isopropanol, polyethylene glycol, etc.), present in the biological material being sterilized that is not bound to or complexed with one or more of the non-liquid components of the biological material. Freely-available liquid includes intracellular water and/or other solvents. The residual solvent contents related as water referenced herein refer to levels determined by the FDA approved, modified Karl Fischer method (Meyer and Boyd, Analytical Chem., 31:215–219, 1959; May, et al., *J. Biol. Standardization,* 10:249–259, 1982; Centers for Biologics Evaluation and Research, FDA, Docket No. 89D-0140, 83–93; 1990) or by near infrared spectroscopy. Quantitation of the residual levels of water or other solvents may be determined by means well known in the art, depending upon which solvent is employed. The proportion of residual solvent to solute may also be considered to be a reflection of the concentration of the solute within the solvent. When so expressed, the greater the concentration of the solute, the lower the amount of residual solvent.

As used herein, the term "sensitizer" is intended to mean a substance that selectively targets viruses, bacteria, in both vegetative and spore states, (including inter- and intracellular bacteria, such as mycoplasmas, ureaplasmas, nanobacteria, chlamydia, rickettsias), yeasts, molds, fungi, single or multicellular parasites, and/or prions or similar agents responsible, alone or in combination, for TSEs, rendering them more sensitive to inactivation by radiation, therefore permitting the use of a lower rate or dose of radiation and/or a shorter time of irradiation than in the absence of the sensitizer. Illustrative examples of suitable sensitizers include, but are not limited to, the following: psoralen and its derivatives and analogs (including 3-carboethoxy psoralens); inactines and their derivatives and analogs; angelicins, khellins and coumarins which contain a halogen substituent and a water solubilization moiety, such as quaternary ammonium ion or phosphonium ion; nucleic acid binding compounds; brominated hematoporphyrin; phthalocyanines; purpurins; porphyrins; halogenated or metal atom-substituted derivatives of dihematoporphyrin esters, hematoporphyrin derivatives, benzoporphyrin derivatives, hydrodibenzoporphyrin dimaleimade, hydrodibenzoporphyrin, dicyano disulfone, tetracarbethoxy hydrodibenzoporphyrin, and tetracarbethoxy hydrodibenzoporphyrin dipropionamide; doxorubicin and daunomycin, which may be modified with halogens or metal atoms; netropsin; BD peptide, S2 peptide; S-303 (ALE compound); dyes, such as hypericin, methylene blue, eosin, fluoresceins (and their derivatives), flavins, merocyanine 540; photoactive compounds, such as bergapten; and SE peptide. In addition, atoms which bind to prions, and thereby increase their sensitivity to inactivation by radiation, may also be used. An illustrative example of such an atom would be the Copper ion, which binds to the prion protein and, with a Z number higher than the other atoms in the protein, increases the probability that the prion protein will absorb energy during irradiation, particularly gamma irradiation.

As used herein, the term "radiation" is intended to mean radiation of sufficient energy to sterilize at least some component of the irradiated biological material. Types of radiation include, but are not limited to, the following: (i) corpuscular (streams of subatomic particles such as neutrons, electrons, and/or protons); (ii) electromagnetic (originating in a varying electromagnetic field, such as radio waves, visible (both mono and polychromatic) and invisible light, infrared, ultraviolet radiation, x-radiation, and gamma rays and mixtures thereof); and (iii) sound and pressure waves. Such radiation is often described as either ionizing (capable of producing ions in irradiated materials) radiation, such as gamma rays, and non-ionizing radiation, such as visible light. The sources of such radiation may vary and, in general, the selection of a specific source of radiation is not critical provided that sufficient radiation is given in an appropriate time and at an appropriate rate to effect sterilization. In practice, gamma radiation is usually produced by isotopes of Cobalt or Cesium, while UV and X-rays are produced by machines that emit UV and X-radiation, respectively, and electrons are often used to sterilize materials in a method known as "E-beam" irradiation that involves their production via a machine. Visible light, both mono- and polychromatic, is produced by machines and may, in practice, be combined with invisible light, such as infrared and UV, that is produced by the same machine or a different machine.

As used herein, the term "tissue" is intended to mean a substance derived or obtained from a multi-cellular living organism that performs one or more functions in the organism or a recipient thereof. Thus, as used herein, a "tissue" may be an aggregation of intercellular substance(s), such as collagen, elastin, fibronectin, fibrin, glycosaminoglycans and the like, and/or cells which are generally morphologically similar, such as hemapoietic cells, bone cells and the like. Accordingly, the term "tissue" is intended to include both allogenic and autologous tissue, including, but not limited to, cellular viable tissue, cellular non-viable tissue and a cellular tissue, such as collagen, elastin, fibronectin, fibrin, glycosaminoglycans and the like. As used herein, the term "tissue" includes naturally occurring tissues, such as tissues removed from a living organism and used as such, or processed tissues, such as tissue processed so as to be less antigenic, for example allogenic tissue intended for transplantation, and tissue processed to allow cells to proliferate into the tissue, for example demineralised bone matrix that has been processed to enable bone cells to proliferate into and through it or heart valves that have been processed to encourage cell engraftment following implantation. Additionally, as used herein, the term "tissue" is intended to include natural, artificial, synthetic, semi-synthetic or semi-artificial materials comprised of biomolecules structured in such a way as to permit the replacement of at least some function(s) of a natural tissue when implanted into a recipient. Such constructs may be placed in a cell-containing environment prior to implantation to encourage their cellularization. Illustrative examples of tissues that may be treated according to the methods of the present invention include, but are not limited to, the following: connective tissue; epithelial tissue; adipose tissue; cartilage, bone (including demineralised bone matrix); muscle tissue; and nervous tissue. Non-limiting examples of specific tissues that may be treated according to the methods of the present invention include heart, lung, liver, spleen, pancreas, kidney, corneas, joints, bone marrow, blood cells (red blood cells, leucocytes, lymphocytes, platelets, etc.), plasma, skin, fat, tendons, ligaments, hair, muscles, blood vessels (arteries, veins), teeth, gum tissue, fetuses, eggs (fertilized and not fertilized), eye lenses, hands, nerve cells, nerves, and other physiologically and anatomically complex tissues, such as intestine, cartilage, entire limbs, cadavers, and portions of brain, and intracellular substances, such as collagen, elastin, fibrinogen, fibrin, fibronectin, glycosaminoglycans, and polysaccharides.

As used herein, the term "to protect" is intended to mean to reduce any damage to the biological material, such as one or more tissues, being irradiated, that would otherwise result from the irradiation of that material, to a level that is insufficient to preclude the safe and effective use of the material following irradiation. In other words, a substance or process "protects" a biological material, such as one or more tissues, from radiation if the presence of that substance or carrying out that process results in less damage to the material from irradiation than in the absence of that substance or process. Thus, a biological material, such as one or more tissues, may be used safely and effectively after irradiation in the presence of a substance or following performance of a process that "protects" the material, but could not be used with as great a degree of safety or as effectively after irradiation under identical conditions but in the absence of that substance or the performance of that process.

As used herein, an "acceptable level" of damage may vary depending upon certain features of the particular method(s) of the present invention being employed, such as the nature and characteristics of the particular one or more tissues and/or non-aqueous solvent(s) being used, and/or the intended use of the material being irradiated, and can be determined empirically by one skilled in the art. An "unacceptable level" of damage would therefore be a level of damage that would preclude the safe and effective use of the biological material, such as one or more tissues, being sterilized. The particular level of damage in a given biological material may be determined using any of the methods and techniques known to one skilled in the art.

B. Particularly Preferred Embodiments

A first preferred embodiment of the present invention is directed to a method for sterilizing one or more tissues that are sensitive to radiation, said method comprising: (i) adding to said one or more tissues at least one stabilizer; and (ii) irradiating said one or more tissues with radiation for a time effective to sterilize said one or more tissues and at a rate effective to sterilize said one or more tissues, wherein said at least one stabilizer and the rate of irradiation are together effective to protect said one or more tissues from said radiation.

A second preferred embodiment of the present invention is directed to a method for sterilizing one or more tissues that are sensitive to radiation, said method comprising: (i) adding to said one or more tissues at least one cryopreservative; and (ii) irradiating said one or more tissues with radiation for a time effective to sterilize said one or more tissues and at a rate effective to sterilize said one or more tissues.

A third preferred embodiment of the present invention is directed to a method for sterilizing one or more tissues that are sensitive to radiation, said method comprising: (i) adding to said one or more tissues at least one stabilizer; (ii) subjecting said at least one tissue to a treatment effective to enhance penetration of said at least one stabilizer into said one or more tissues; and (iii) irradiating said one or more tissues with radiation for a time effective to sterilize said one or more tissues and at a rate effective to sterilize said one or more tissues, wherein said at least one stabilizer and the rate of irradiation are together effective to protect said one or more tissue from said radiation.

A fourth preferred embodiment of the present invention is directed to a method for sterilizing one or more tissues that are sensitive to radiation, said method comprising: (i) adding to said one or more tissues at least one cryopreservative; (ii) subjecting said one or more tissues to a treatment effective to enhance penetration of said at least one cryopreservative into said one or more tissues; and (iii) irradiating said one or more tissues with radiation for a time effective to sterilize said one or more tissues and at a rate effective to sterilize said one or more tissues.

Another preferred embodiment of the present invention is directed to a composition comprising one or more tissues and at least one cryopreservative in an amount effective to preserve said one or more tissues for their intended use following sterilization with radiation.

According to certain embodiments of the present invention, the one or more tissues may contain a mixture of water and a non-aqueous solvent, such as ethanol and/or acetone. In such embodiments, the non-aqueous solvent(s) is (are) preferably a non-aqueous solvent that is not prone to the formation of free-radicals upon irradiation, and most preferably a non-aqueous solvent that is not prone to the formation of free-radicals upon irradiation and that has little or no dissolved oxygen or other gas(es) that is (are) prone to the formation of free-radicals upon irradiation. Volatile non-aqueous solvents are particularly preferred, even more particularly preferred are non-aqueous solvents that are also stabilizers, such as ethanol and acetone.

The non-aqueous solvent is preferably a non-aqueous solvent that is not prone to the formation of free-radicals upon irradiation, and more preferably a non-aqueous solvent that is not prone to the formation of free-radicals upon irradiation and that has little or no dissolved oxygen or other gas(es) that is (are) prone to the formation of free-radicals upon irradiation. Volatile non-aqueous solvents are particularly preferred, even more particularly preferred are non-aqueous solvents that are stabilizers, such as ethanol and acetone.

According to certain methods of the present invention, a stabilizer is added prior to irradiation of the one or more tissues with radiation. This stabilizer is preferably added to the one or more tissues in an amount that is effective to protect the one or more tissues from the radiation. Alternatively, the stabilizer is added to the one or more tissues in an amount that, together with a non-aqueous solvent, is effective to protect the one or more tissues from the radiation. Suitable amounts of stabilizer may vary depending upon certain features of the particular method(s) of the present invention being employed, such as the particular stabilizer being used and/or the nature and characteristics of the particular one or more tissues being irradiated and/or its intended use, and can be determined empirically by one skilled in the art.

According to certain methods of the present invention, a cryopreservative is added prior to irradiation of the one or more tissues with radiation. This cryopreservative is preferably added to the one or more tissues in an amount that is effective to protect the one or more tissues during cooling or freezing. Suitable amounts of cryopreservatives may vary depending upon certain features of the particular method(s) of the present invention being employed, such as the particular cryopreservative being used and/or the nature and characteristics of the particular one or more tissues being irradiated and/or its intended use, and can be determined empirically by one skilled in the art. Illustrative examples of suitable cryopreservatives according to the present invention include chondroitin sulfate, glycosaminoglycan dimethylsulfoxide, cell penetrating organic solutes, polysaccharides, glycerol, Dulbecco's minimum essential medium, glutamine, D-glucose, sodium pyruvate, fetal calf serum, papaverine, DMSO, glycerol, trehalose, $KH_2PO_4$, $K_2HPO_4$, KCl, mannitol, $NaHCO_3$, sodium ascorbate, 1,2-propanediol, formamide, 2,3-butanediol, probuchol, curcumin and mixtures thereof. In a particularly preferred embodiment of the present invention, the cryopreservative comprises a mixture of Dulbecco's minimum essential medium, hepes buffer, glutamine, D-glucose, sodium pyruvate, fetal calf serum, papaverine, chondroitin sulfate and DMSO.

According to certain methods of the present invention, the residual solvent content of the one or more tissues is reduced prior to irradiation of the one or more tissues with radiation. The residual solvent content is preferably reduced to a level that is effective to protect the one or more tissues from the radiation. Suitable levels of residual solvent content may vary depending upon certain features of the particular method(s) of the present invention being employed, such as the nature and characteristics of the particular one or more tissues being irradiated and/or its intended use, and can be determined empirically by one skilled in the art. There may be tissue for which it is desirable to maintain the residual solvent content to within a particular range, rather than a specific value.

According to certain embodiments of the present invention, when the one or more tissues also contain water, the residual solvent (water) content of one or more tissues may be reduced by dissolving or suspending the one or more tissues in a non-aqueous solvent that is capable of dissolving water. Preferably, such a non-aqueous solvent is not prone to the formation of free-radicals upon irradiation and has little or no dissolved oxygen or other gas(es) that is (are) prone to the formation of free-radicals upon irradiation.

While not wishing to be bound by any theory of operability, it is believed that the reduction in residual solvent content reduces the degrees of freedom of the one or more tissues, reduces the number of targets for free radical generation and may restrict the diffusability of these free radicals. Similar results might therefore be achieved by lowering the temperature of the one or more tissues below their eutectic point(s) or below their freezing point(s), or by vitrification to likewise reduce the degrees of freedom of the one or more tissues. These results may permit the use of a higher rate and/or dose of radiation than might otherwise be acceptable. Thus, the methods described herein may be performed at any temperature that doesn't result in unacceptable damage to the one or more tissues, i.e., damage that would preclude the safe and effective use of the one or more tissues. Preferably, the methods described herein are performed at ambient temperature or below ambient temperature, such as below the eutectic point(s) or freezing point(s) of the one or more tissues being irradiated.

In certain embodiments of the present invention, the desired residual solvent content of a particular tissue may be found to lie within a range, rather than at a specific point. Such a range for the preferred residual solvent content of a particular tissue may be determined empirically by one skilled in the art.

The residual solvent content of the one or more tissues may be reduced by any of the methods and techniques known to those skilled in the art for reducing solvent from one or more tissues without producing an unacceptable level of damage to the one or more tissues. Such methods include, but are not limited to, lyophilization, drying, concentration, addition of alternative solvents, evaporation, chemical extraction, sonication induced nucleation and vitrification.

A particularly preferred method for reducing the residual solvent content of one or more tissues is lyophilization.

Another particularly preferred method for reducing the residual solvent content of one or more tissues is vitrification, which may be accomplished by any of the methods and techniques known to those skilled in the art, including the addition of solute and or additional solutes, such as sucrose, to raise the eutectic point(s) of the one or more tissues, followed by a gradual application of reduced pressure to the one or more tissues in order to remove the residual solvent. The resulting glassy material will then have a reduced residual solvent content.

According to certain methods of the present invention, the one or more tissues to be sterilized may be immobilized upon or attached to a solid surface by any means known and available to one skilled in the art. For example, the one or more tissues to be sterilized may be attached to a biological or non-biological substrate.

The radiation employed in the methods of the present invention may be any radiation effective for the sterilization of the one or more tissues being treated. The radiation may be corpuscular, including E-beam radiation. Preferably the radiation is electromagnetic radiation, including x-rays, infrared, visible light, UV light and mixtures of various wavelengths of electromagnetic radiation. A particularly preferred form of radiation is gamma radiation.

According to the methods of the present invention, the one or more tissues are irradiated with the radiation at a rate effective for the sterilization of the one or more tissues, while not producing an unacceptable level of damage to the one or more tissues. Suitable rates of irradiation may vary depending upon certain features of the methods of the present invention being employed, such as the nature and characteristics of the particular tissue, which may contain a non-aqueous solvent, being irradiated, the particular form of radiation involved, and/or the particular biological contaminants or pathogens being inactivated. Suitable rates of irradiation can be determined empirically by one skilled in the art. Preferably, the rate of irradiation is constant for the duration of the sterilization procedure. When this is impractical or otherwise not desired, a variable or discontinuous irradiation may be utilized.

According to the methods of the present invention, the rate of irradiation may be optimized to produce the most advantageous combination of product recovery and time required to complete the operation. Both low (≦3 kGy/hour) and high (>3 kGy/hour) rates may be utilized in the methods described herein to achieve such results. The rate of irradiation is preferably selected to optimize the recovery of the one or more tissues while still sterilizing the one or more tissues. Although reducing the rate of irradiation may serve to decrease damage to the one or more tissues, it will also result in longer irradiation times being required to achieve a particular desired total dose. A higher dose rate may therefore be preferred in certain circumstances, such as to minimize logistical issues and costs, and may be possible particularly when used in accordance with the methods described herein for protecting tissue from irradiation.

According to a particularly preferred embodiment of the present invention, the rate of irradiation is not more than about 3.0 kGy/hour, more preferably between about 0.1 kGy/hr and 3.0 kGy/hr, even more preferably between about 0.25 kGy/hr and 2.0 kGy/hour, still even more preferably between about 0.5 kGy/hr and 1.5 kGy/hr and most preferably between about 0.5 kGy/hr and 1.0 kGy/hr.

According to another particularly preferred embodiment of the present invention, the rate of irradiation is at least about 3.0 kGy/hr, more preferably at least about 6 kGy/hr, even more preferably at least about 16 kGy/hr, even more preferably at least about 30 kGy/hr and most preferably at least about 45 kGy/hr or greater.

According to the methods of the present invention, the one or more tissues to be sterilized are irradiated with the radiation for a time effective for the sterilization of the one or more tissues. Combined with irradiation rate, the appropriate irradiation time results in the appropriate dose of irradiation being applied to the one or more tissues. Suitable irradiation times may vary depending upon the particular form and rate of radiation involved and/or the nature and characteristics of the particular one or more tissues being irradiated. Suitable irradiation times can be determined empirically by one skilled in the art.

According to the methods of the present invention, the one or more tissues to be sterilized are irradiated with radiation up to a total dose effective for the sterilization of the one or more tissues, while not producing an unacceptable level of damage to those one or more tissues. Suitable total doses of radiation may vary depending upon certain features of the methods of the present invention being employed, such as the nature and characteristics of the particular one or more tissues being irradiated, the particular form of radiation involved, and/or the particular biological contaminants or pathogens being inactivated. Suitable total doses of radiation can be determined empirically by one skilled in the art. Preferably, the total dose of radiation is at least 25 kGy, more preferably at least 45 kGy, even more preferably at least 50 kGy, still more preferably at least 75 kGy and still even more preferably at least 100 kGy or greater, such as 150 kGy or 200 kGy or greater.

The particular geometry of the one or more tissues being irradiated, such as the thickness and distance from the source of radiation, may be determined empirically by one skilled in the art. A preferred embodiment is a geometry that provides for an even rate of irradiation throughout the preparation of one or more tissues. A particularly preferred embodiment is a geometry that results in a short path length for the radiation through the preparation, thus minimizing the differences in radiation dose between the front and back of the preparation. This may be further minimized in some preferred geometries, particularly those wherein the preparation of one or more tissues has a relatively constant radius about its axis that is perpendicular to the radiation source and by the utilization of a means of rotating the preparation of one or more tissues about said axis. In a particularly preferred embodiment of the present invention, the tissue is irradiated in an arc centered about the radiation source.

Similarly, according to certain methods of the present invention, an effective package for containing the preparation of one or more tissues during irradiation is one which combines stability under the influence of irradiation, and which minimizes the interactions between the package of one or more tissues and the radiation. Preferred packages maintain a seal against the external environment before, during and post-irradiation, and are not reactive with the preparation of one or more tissues within, nor do they produce chemicals that may interact with the preparation of one or more tissues within. Particularly preferred examples include but are not limited to containers that comprise glasses stable when irradiated, stoppered with stoppers made of rubber or other suitable materials that is relatively stable during radiation and liberates a minimal amount of compounds from within, and sealed with metal crimp seals of aluminium or other suitable materials with relatively low Z numbers. Suitable materials can be determined by measuring their physical performance, and the amount and type of reactive leachable compounds post-irradiation, and by examining other characteristics known to be important to the containment of such biological materials as tissue empirically by one skilled in the art.

Similarly, in certain preferred embodiments of the present invention, "terminal sterilization" is carried out. That is, the one or more tissues are packaged prior to irradiation in a package that is impervious to pathogens. Following treatment according to the present invention, the one or more tissues may be distributed safely without contamination or degradation. Thus, as used herein, the phrase "packaged prior to sterilization" includes terminal sterilization.

According to certain methods of the present invention, an effective amount of at least one sensitizing compound may optionally be added to the one or more tissues prior to irradiation, for example to enhance the effect of the irradiation on the biological contaminant(s) or pathogen(s) therein, while employing the methods described herein to minimize the deleterious effects of irradiation upon the one or more tissues. Suitable sensitizers are known to those skilled in the art, and include psoralens and their derivatives, riboflavins and their derivatives and inactines and their derivatives.

According to the methods of the present invention, the irradiation of the one or more tissues may occur at any temperature that is not deleterious to the one or more tissues being sterilized. According to one preferred embodiment, the one or more tissues are irradiated at ambient temperature. According to an alternate preferred embodiment, the one or more tissues are irradiated at reduced temperature, i.e., a temperature below ambient temperature, such as by cooling on dry ice, liquid nitrogen or combinations thereof. Preferred temperatures below ambient temperature according to the present invention include 0° C., −20° C., −40° C., −60°C., −78° C. or −196° C. According to this embodiment of the present invention, the one or more tissues are preferably irradiated at or below the freezing or eutectic point(s) of the one or more tissues or the residual solvent therein. According to another alternate preferred embodiment, the one or more tissues are irradiated at elevated temperature, i.e., a temperature above ambient temperature, such as 37° C., 60° C., 72° C. or 80° C. While not wishing to be bound by any theory, the use of elevated temperature may enhance the effect of irradiation on the biological contaminant(s) or pathogen(s) and therefore allow the use of a lower total dose of radiation.

Most preferably, the irradiation of the one or more tissues occurs at a temperature that protects the preparation of one or more tissues from radiation. Suitable temperatures can be determined empirically by one skilled in the art.

In certain embodiments of the present invention, the temperature at which irradiation is performed may be found to lie within a range, rather than at a specific point. Such a range for the preferred temperature for the irradiation of a particular tissue may be determined empirically by one skilled in the art.

According to certain preferred embodiments of the present invention, the irradiation of the biological material is performed under conditions whereby the temperature of said biological material increases during the irradiation from an initial temperature ($T_i$) to a final temperature ($T_f$). Preferably, the increase in the temperature of the biological material ($\Delta T$) is about equal to the total dose of radiation (D) divided by the specific heat capacity (c) of the biological material. Specific heat capacities of particular biological materials are known, or may be determined empirically by one skilled in the art using known methods and techniques.

Preferably, the final temperature ($T_f$) is at or below a level effective to protect the biological material from the radiation. According to such embodiments, the maximum acceptable temperature ($T_{max}$) for a particular biological material is preferably determined empirically by one skilled in the art employing the particular irradiation conditions desired. According to such embodiments of the present invention, the initial temperature ($T_i$) of the biological material is then preferably set at a level at or below $T_{max}$-$\Delta T$ prior to irradiation.

According to other embodiments of the present invention, the increase in the temperature of the biological material is less than the total dose of radiation (D) divided by the specific heat capacity (c) of the biological material. Such variation may be due to the particular biological material being irradiated, the size of the sample being irradiated, the packaging in which the sample is contained, the particular method(s) of cooling, as well as the environment in which the package is held during irradiation. According to such embodiments, the increase in the temperature of the biological material ($\Delta T$) is preferably determined empirically by one skilled in the art using known methods and techniques. The initial temperature ($T_i$) of the biological material is then preferably set at a level at or below $T_{max}$-$\Delta T$ prior to irradiation.

According to the methods of the present invention, the irradiation of the one or more tissues may occur at any pressure which is not deleterious to the one or more tissues being sterilized. According to one preferred embodiment, the one or more tissues are irradiated at elevated pressure. More preferably, the one or more tissues are irradiated at elevated pressure due to the application of sound waves or the use of a volatile. While not wishing to be bound by any theory, the use of elevated pressure may enhance the effect of irradiation on the biological contaminant(s) or pathogen(s) and/or enhance the protection afforded by one or more stabilizers, and therefore allow the use of a lower total dose of radiation. Suitable pressures can be determined empirically by one skilled in the art.

Generally, according to the methods of the present invention, the pH of the one or more tissues undergoing sterilization is about 7. In some embodiments of the present invention, however, the one or more tissues may have a pH of less than 7, preferably less than or equal to 6, more preferably less than or equal to 5, even more preferably less than or equal to 4, and most preferably less than or equal to 3. In alternative embodiments of the present invention, the one or more tissues may have a pH of greater than 7, preferably greater than or equal to 8, more preferably greater than or equal to 9, even more preferably greater than or equal to 10, and most preferably greater than or equal to 11. According to certain embodiments of the present invention, the pH of the preparation of one or more tissues undergoing sterilization is at or near the isoelectric point of one of the components of the one or more tissues. Suitable pH levels can be determined empirically by one skilled in the art.

Similarly, according to the methods of the present invention, the irradiation of the one or more tissues may occur under any atmosphere that is not deleterious to the one or more tissues being treated. According to one preferred embodiment, the one or more tissues are held in a low oxygen atmosphere or an inert atmosphere. When an inert atmosphere is employed, the atmosphere is preferably composed of a noble gas, such as helium or argon, more preferably a higher molecular weight noble gas, and most preferably argon. According to another preferred embodiment, the one or more tissues are held under vacuum while being irradiated. According to a particularly preferred embodiment of the present invention, the one or more tissues (lyophilized, liquid or frozen) are stored under vacuum or an inert atmosphere (preferably a noble gas, such as helium or argon, more preferably a higher molecular weight noble gas, and most preferably argon) prior to irradiation. According to an alternative preferred embodiment of the present invention, the one or more tissues are held under low pressure, to decrease the amount of gas, particularly oxygen and nitrogen, dissolved in the liquid, prior to irradiation, either with or without a prior step of solvent reduction, such as lyophilization. Such degassing may be performed using any of the methods known to one skilled in the art. For example, the one or more tissues may be treated prior to irradiation with at least one cycle, and preferably three cycles, of being subjected to a vacuum and then being placed under an atmosphere comprising at least one noble gas, such as argon, or nitrogen.

In another preferred embodiment, where the one or more tissues contain oxygen or other gases dissolved within the one or more tissues or within their container or associated with them, the amount of these gases within or associated with the preparation of one or more tissues may be reduced by any of the methods and techniques known and available to those skilled in the art, such as the controlled reduction of pressure within a container (rigid or flexible) holding the preparation of one or more tissues to be treated or by placing the preparation of one or more tissues in a container of approximately equal volume to the tissue, i.e., leaving no head space.

In certain embodiments of the present invention, when the one or more tissues to be treated contains an aqueous or non-aqueous solvent, or a mixture of such solvents, at least one stabilizer is introduced according to any of the methods and techniques known and available to one skilled in the art, including soaking the tissue in a solution containing the stabilizer(s), preferably under pressure, at elevated temperature and/or in the presence of a penetration enhancer, such as dimethylsulfoxide, and more preferably, when the stabilizer(s) is a protein, at a high concentration. Other methods of introducing at least one stabilizer into tissue include, but are not limited to, the following: applying a gas containing the stabilizer(s), preferably under pressure and/or at elevated temperature; injecting the stabilizer(s) or a solution containing the stabilizer(s) directly into the tissue; placing the tissue under reduced pressure and then introducing a gas or solution containing the stabilizer(s); dehydrating the tissue, such as by using a buffer of high ionic and/or osmolar strength, and rehydrating the tissue with a solution containing the stabilizer(s); applying a high ionic strength solvent containing the stabilizer(s), which may optionally be followed by a controlled reduction in the ionic strength of the solvent; cycling the tissue between solutions of high ionic and/or osmolar strength and solutions of low ionic and/or osmolar strength containing the stabilizer(s); applying the at least one stabilizer within or as a component of a microemulsion; and combinations of two or more of these methods. One or more sensitizers may also be introduced into tissue according to such methods.

In certain embodiments of the present invention, at least one cryopreservative is introduced into the one or more tissues according to any of the methods and techniques known and available to one skilled in the art, including soaking the tissue in a solution containing the cryopreservative(s), preferably under pressure, at elevated temperature and/or in the presence of a penetration enhancer, such as dimethylsulfoxide, and more preferably. Other methods of introducing at least one cryopreservative into tissue include, but are not limited to, the following: applying a gas containing the cryopreservative(s), preferably under pressure and/or at elevated temperature; injecting the cryopreservative(s) or a solution containing the cryopreservative(s) directly into the tissue; placing the tissue under reduced pressure and then introducing a gas or solution containing the cryopreservative(s); dehydrating the tissue, such as by using a buffer of high ionic and/or osmolar strength, and rehydrating the tissue with a solution containing the cryopreservative(s); applying a high ionic strength solvent containing the cryopreservative(s), which may optionally be followed by a controlled reduction in the ionic strength of the solvent; cycling the tissue between solutions of high ionic and/or osmolar strength and solutions of low ionic and/or osmolar strength containing the cryopreservative(s); applying the at least one cryopreservative within or as a component of a microemulsion; and combinations of two or more of these methods. One or more sensitizers may also be introduced into tissue according to such methods.

According to certain preferred embodiments of the present invention, the one or more tissues may be subjected to a treatment effective to enhance penetration of the one or more stabilizers and/or cryopreservatives and/or sensitizers into the tissue. Such treatments include physical treatments and chemical treatments.

For instance, with respect to chemical treatment, the tissue may treated with one or more compounds that cause an increase in the distance between molecules in the tissue, thereby promoting penetration of the stabilizers and/or cryopreservatives and/or sensitizers into the one or more tissues. Alternatively, the chemical treatment may include treating the one or more tissues with a microemulsion effective to enhance penetration of the stabilizers and/or cryopreservatives and/or sensitizers into the one or more tissues.

Similarly, the tissue may be treated with one or more compounds that cause macromolecules in the tissue to become less compact, or relaxed, thereby promoting penetration of the stabilizer(s) and/or cryopreservatives and/or sensitizer(s) into the tissue or providing a greater surface area of tissue to be in contact with the stabilizer(s) and/or cryopreservatives and/or sensitizer(s). The compounds that cause macromolecules in the tissue to become less compact, or relaxed, may also be applied prior to introduction of the stabilizer(s) and/or cryopreservatives and/or sensitizer(s), which may then be introduced in a similar solution followed by application of a solution containing a similar amount of stabilizer(s) and/or cryopreservatives and/or sensitizer(s) but a reduced amount of the compounds that cause macromolecules in the tissue to become less compact, or relaxed. Repeated applications of such solutions, with progressively lower amounts of compounds that cause macromolecules in the tissue to become less compact, or relaxed, may subsequently be applied.

The compounds that promote penetration may be used alone or in combination, such as a combination of a compound that causes macromolecules in the tissue to become less compact and a compound that causes an increase in the distance between molecules in the tissue.

Further, in those embodiments of the present invention wherein the stabilizer(s) and/or cryopreservatives and/or sensitizer(s) is cationic, one or more anionic compounds may be added to the solution containing the stabilizer(s) and/or cryopreservatives and/or sensitizer(s) prior to and/or during application thereof to the tissue. The anionic compound(s) may also be applied prior to introduction of the stabilizer(s) and/or cryopreservatives and/or sensitizer(s), which may then be introduced in a similar solution followed by application of a solution containing a similar amount of stabilizer(s) and/or cryopreservatives and/or sensitizer(s) but a reduced amount of the anionic compound(s). Repeated applications of such solutions, with progressively lower amounts of anionic compound(s) may subsequently be applied.

Similarly, in those embodiments of the present invention wherein the stabilizer(s) and/or cryopreservatives and/or sensitizer(s) is anionic, one or more cationic compounds may be added to the solution containing the stabilizer(s) and/or cryopreservatives and/or sensitizer(s) prior to and/or during application thereof to the tissue. The cationic compound(s) may also be applied prior to introduction of the stabilizer(s) and/or cryopreservatives and/or sensitizer(s), which may then be introduced in a similar solution followed by application of a solution containing a similar amount of stabilizer(s) and/or cryopreservatives and/or sensitizer(s) but a reduced amount of the cationic compound(s). Repeated applications of such solutions, with progressively lower amounts of cationic compound(s) may subsequently be applied.

Regarding physical treatments effective to enhance penetration of the one or more stabilizer(s) and/or cryopreservative(s) and/or sensitizer(s) into the tissue, examples include, but are not limited to, physical agitation, such as by shaking or sonication, slow freezing and fast freezing.

According to embodiments of the present invention employing physical agitation, such as sonication or shaking, physical agitation is carried out for a time effective to enhance penetration of the one or more stabilizer(s) and/or cryopreservative(s) and/or sensitizer(s) into the tissue. The duration of such treatment will depend upon, among other factors, the nature of the one or more tissues, the nature of the solvent(s) employed, and the nature of the one or more stabilizer(s) and/or cryopreservative(s) and/or sensitizer(s). Suitable times may easily be determined empirically by one having ordinary skill in the art.

Fast freezing is typically carried out in a relatively short period of time, preferably less than about 15 minutes, more preferably less than about 10 minutes, even more preferably about 5 minutes, still more preferably less than about 5 minutes and most preferably less than about 1 minute. Fast freezing may be carried out, for instance, by placing the one or more tissues in a cold bath, such as, for example, dry-ice/ethanol, dry ice/acetone, dry-ice/methanol and the like, or exposing one or more tissues to the liquid phase of a gas that liquifies at low temperature or its vapor, such as liquified nitrogen, or to the solid phase of a gas that solidifies at a low temperature, such as carbon dioxide (as "dry ice") or a suitable mixture of two or more of the treatments described herein.

In embodiments of the present invention employing slow freezing, the temperature of the tissue is gradually lowered over a prolonged period of time, for instance from about one-half hour to about 2 hours, preferably about one hour, at a rate of from about 0.5 to about 2.5° C./min. Preferably, the rate is from about 0.5 to about 1.5° C./min, more preferably about 0.5 to about 1.0° C./min and most preferably about 1° C./min.

In addition to enhancing penetration of the stabilizers and/or cryopreservatives and/or sensitizers, the treatments described above may also enhance cleaning of the one or more tissues. That is, by treatment as set forth above with respect to penetration enhancement, the physical and chemical treatments are effective to clean the one or more tissues and remove infected or undesirable material therefrom. For instance, bone may be subjected to physical treatment, e.g., sonication, and/or chemical treatment, e.g., treatment with a microemulsion, to remove marrow and other residual residues therefrom. In this way, components that might give rise to infection or contamination may effectively be eliminated.

It will be appreciated that the combination of one or more of the features described herein may be employed to further minimize undesirable effects upon the one or more tissues caused by irradiation, while maintaining adequate effectiveness of the irradiation process on the biological contaminant (s) or pathogen(s). For example, in addition to the use of a stabilizer, a particular tissue may also be lyophilized, held at a reduced temperature and kept under vacuum prior to irradiation to further minimize undesirable effects.

The sensitivity of a particular biological contaminant or pathogen to radiation is commonly calculated by determining the dose necessary to inactivate or kill all but 37% of the agent in a sample, which is known as the $D_{37}$ value. The desirable components of a tissue may also be considered to have a $D_{37}$ value equal to the dose of radiation required to eliminate all but 37% of their desirable biological and physiological characteristics.

In accordance with certain preferred methods of the present invention, the sterilization of one or more tissues is conducted under conditions that result in a decrease in the $D_{37}$ value of the biological contaminant or pathogen without a concomitant decrease in the $D_{37}$ value of the one or more tissues. In accordance with other preferred methods of the present invention, the sterilization of one or more tissues is conducted under conditions that result in an increase in the $D_{37}$ value of the tissue material. In accordance with the most preferred methods of the present invention, the sterilization of one or more tissues is conducted under conditions that result in a decrease in the $D_{37}$ value of the biological contaminant or pathogen and a concomitant increase in the $D_{37}$ value of the one or more tissues.

In accordance with certain preferred methods of the present invention, the sterilization of one or more tissues is conducted under conditions that reduce the possibility of the production of neo-antigens. In accordance with other preferred embodiments of the present invention, the sterilization of one or more tissues is conducted under conditions that result in the production of substantially no neo-antigens. Additionally, in accordance with other preferred embodiments of the present invention, the neo-antigen formation may be reduced relative to tissues not treated according to the present invention. The present invention also includes tissues sterilized according to such methods.

In accordance with certain preferred methods of the present invention, the sterilization of one or more tissues is conducted under conditions that reduce the total antigenicity of the tissue(s). In accordance with other preferred embodiments of the present invention the sterilization of one or more tissues is conducted under conditions that reduce the number of reactive allo-antigens and/or xeno-antigens in the tissue(s). The present invention also includes tissues sterilized according to such methods.

A particularly preferred tissue for use with the methods of the present invention is collagen. According to certain embodiments of the present invention, collagen is employed as a model tissue for determining optimal conditions, such as preferred rates of irradiation, temperatures, residual solvent content, and the like, for sterilizing a given tissue type with gamma radiation without rendering the tissue unsafe and/or ineffective for its intended purpose. Thus, another preferred embodiment of the present invention is directed to an assay for determining the optimal conditions for sterilizing a tissue that contains collagen without adversely affective a predetermined biological characteristic or property thereof, which comprises the steps of: (i) irradiating collagen under a pre-determined set of conditions effective to sterilize the tissue; (ii) determining the turbidity of the irradiated collagen; and (iii) repeating steps (i) and (ii) with a different pre-determined set of conditions until the turbidity of the irradiated collagen reaches a pre-determined acceptable level.

According to certain preferred embodiments of the present invention, one or more tissues sterilized according to the methods described herein may be introduced into a mammal in need thereof for prophylaxis or treatment of a condition or disease or malfunction or deficit of a tissue. Methods of introducing such tissue into a mammal are known to those skilled in the art.

When employed in such embodiments, one or more tissues sterilized according to the methods described herein do not produce sufficient negative characteristics in the tissue(s) following introduction into the mammal to render the tissue(s) unsafe and/or ineffective for the intended use thereof. Illustrative examples of such negative characteristics include, but are not limited to, inflammation and calcification. Such negative characteristics may be detected by any means known to those skilled in the art, such as MRIs, CAT scans and the like.

Tissues treated according to the present invention are likely to have a decreased incidence of rejection in a recipient, since pathogens and other contaminants are either reduced or eliminated by practicing the present invention. There may also be a reduction in the number or magnitude of the response provoked by alloantigens and/or neoantigens. Additionally, tissues treated according to the present invention, for instance heart valves and ligaments, are likely to show less calcification than those not treated according to the present invention. Moreover, tissues treated according to the methods of the present invention are likely to exhibit lower toxicity and mutagenicity than tissues not so treated.

According to particularly preferred embodiments of the present invention, sterilization of the one or more tissues is conducted after the tissue(s) is packaged, i.e. as a terminal sterilization process.

EXAMPLES

The following examples are illustrative, but not limiting, of the present invention. Other suitable modifications and adaptations' are of the variety normally encountered by those skilled in the art and are fully within the spirit and scope of the present invention. For example, heart valves from animal species other than pig, such as bovine or human, are encompassed by this technology, as are heart valves from transgenic mammals. In addition, heart valves prepared/modified by practice of the present invention may be used for transplantation into any animal, particularly into mammals. Furthermore, the principles of the technology of the present invention may be practiced on animal tissues and organs other than heart valves. Unless otherwise noted, all irradiation was accomplished using a $^{60}Co$ source.

EXAMPLES

Example 1

In this experiment, porcine heart valves were gamma irradiated in the presence of polypropylene glycol 400 (PPG400) and, optionally, a scavenger, to a total dose of 30 kGy (1.584 kGy/hr at −20° C.).
Materials:
Tissue—Porcine Pulmonary Valve (PV) Heart valves were harvested prior to use and stored.
Tissue Preparation Reagents—
  Polypropylene Glycol 400. Fluka: cat# 81350, lot# 386716/1
  Trolox C. Aldrich: cat# 23,881-3, lot# 02507TS
  Coumaric Acid. Sigma: cat# C-9008, lot# 49H3600
  n-Propyl Gallate. Sigma: cat# P-3130, lot# 117H0526
  α-Lipoic Acid. CalBiochem: cat# 437692, lot# B34484
  Dulbecco's PBS. Gibco BRL: cat# 14190-144, lot# 1095027
  2.0 ml Screw Cap tubes. VWR Scientific Products: cat# 20170-221, lot# 0359
Tissue Hydrolysis Reagents—
  Nerl $H_2O$. NERL Diagnostics: cat# 9800-5, lot# 03055151
  Acetone. EM Science: cat# AX0125-5, lot# 37059711
  6 N constant boiling HCl. Pierce: cat# 24309, lot# BA42184
  Int-Pyd (Acetylated Pyridinoline) HPLC Internal Standard. Metra Biosystems Inc.: cat# 8006,
  lot# 9H142, expiration 2/2002, Store at ≦−20° C.
  Hydrochloric Acid. VWR Scientific: cat# VW3110-3, lot# n/a
  Heptafluorobutyric Acid (HFBA) Sigma: cat# H-7133, lot# 20K3482
    FW 214.0 store at 2–8° C.
  SP-Sephadex C-25 resin. Pharmacia: cat# 17-0230-01, lot# 247249 (was charged with NaCl as per manufacturer suggestion)
  Hydrolysis vials—10 mm×100 mm vacuum hydrolysis tubes. Pierce: cat# 29560, lot #BB627281
Heating module—Pierce, Reacti-therm.: Model # 18870, S/N 1125000320176
Savant—Savant Speed Vac System
Speed Vac Model SC110, model # SC110-120, serial # SC110-SD171002-1H
  a. Refrigerated Vapor Trap Model RVT100, model # RVT100-120V, serial # RVT100-58010538-1B
  b. Vacuum pump, VP 100 Two Stage Pump Model VP100, serial # 93024
Column—Phenomenex, Luna 5µ C18(2) 100 Å, 4.6×250 mm. Part # 00G-4252-E0, S/N# 68740-25, B/N# 5291-29
PLC System: Shimadzu System Controller SCL-10A
  Shimadzu Automatic Sample Injector SIL-10A (50 µl loop)
  Shimadzu Spectrofluorometric Detector RF-10A
  Shimadzu Pumps LC-10AD
  Software—Class-VP version 4.1
Low-binding tubes—MiniSorp 100×15 Nunc-Immunotube. Batch # 042950, cat# 468608
Methods:
A. Preparation of Stabilizer Solutions:
Trolox C:
  The 0.5 M solution was not soluble; therefore additional PPG was added. After water bath sonication at 25° C. and above for at least 30 minutes, Trolox C is soluble at 125 mM.
Coumaric Acid:
  Water bath sonicated at 25° C. and above for approximately 15 minutes—not 100% soluble. An additional 1 ml PPG was added and further water bath sonicated.
n-Propyl Gallate:
  The 0.5M solution was soluble after a 20–30 minute water bath sonication.
1 M α-Lipoic Acid:
  Very soluble after 10 minute water bath sonication.
  Final Stocks of Scavengers:
    125 mM Trolox C—4 ml
    0.5 M Coumaric acid—2 ml
    0.5 M n-Propyl Gallate—2 ml
    1 M Lipoic Acid—2 ml
B. Treatment of Valves Prior to Gamma-irradiation.
  1. PV heart valves were thawed on wet ice.
  2. Cusps were dissected out from each valve and pooled into 50 ml conical tubes containing cold Dulbecco's PBS.
  3. Cusps were washed in PBS at 4° C. for approximately 1.5 hrs; changing PBS during that time a total of 6 times.
  4. 2 cusps were placed in each of six 2 ml screw cap tube.
  5. 1.2 ml of PPG were added to two tubes (one of these tubes was designated 0 kGy and the other tube was designated 30 kGy):
    1.2 ml of 125 mM Trolox C in PPG were added to another two tubes
    1.2 ml of SCb stabilizer mixture—comprising of 1.5 ml 125 mM Trolox C, 300 µl 1 M Lipoic Acid, 600 µl 0.5 M Coumaric Acid and 600 µl 0.5 M n-Propyl Gallate (Final concentrations: 62.5 mM, 100 mM, 100 mM and 100 mM respectively) were added to the final two tubes.
  6. Tubes were incubated at 4° C., with rocking for about 60 hours.
  7. Stabilizer solutions and cusps were transferred into 2 ml glass vials for gamma-irradiation.
  8. All vials were frozen on dry ice.
  9. Control samples were kept in-house at −20° C.
C. Gamma-Irradiation of Tissue.
  Samples were irradiated at a rate of 1.584 kGy/hr at −20° C. to a total dose of 30 kGy.
D. Processing Tissue for Hydrolysis/Extraction.
  1. Since PPG is viscous, PBS was added to allow for easier transfer of material.
  2. Each pair of cusps (2 per condition) were placed into a 50 ml Falcon tube filled with cold PBS and incubated on ice—inverting tubes periodically.

3. After one hour PBS was decanted from the tubes containing cusps in PPG/0 kGy and PPG/30 kGy and replenished with fresh cold PBS. For the PPG samples containing Trolox C or SCb stabilizer mixture, fresh 50 ml Falcon tubes filled with cold PBS were set-up and the cusps transferred.

4. An additional 3 washes were done.

5. One cusp was transferred into a 2 ml Eppendorf tube filled with cold PBS for extraction. The other cusp was set-up for hydrolysis.

E. Hydrolysis of Tissue.

1. Each cusp was washed 6× with acetone in an Eppendorf tube (approximately 1.5 ml/wash).

2. Each cusp was subjected to SpeedVac (with no heat) for approximately 15 minutes or until dry.

3. Samples were weighed, transferred to hydrolysis vials and 6 N HCl added at a volume of 20 mg tissue/ml HCl:

| Sample ID | Dry Weight (mg) | µl 6 N HCl |
|---|---|---|
| 1. PPG/0 | 6.49 | 325 |
| 2. PPG/30 | 7.26 | 363 |
| 3. PPG T/0 | 5.80 | 290 |
| 4. PPG T/30 | 8.20 | 410 |
| 5. PPG SCb/0 | 6.41 | 321 |
| 6. PPG SCb/30 | 8.60 | 430 |

4. Samples were hydrolyzed at 110° C. for approximately 23 hours.

5. Hydrolysates were transferred into Eppendorf tubes and centrifuged @ 12,000 rpm for 5 min.

6. Supernatent was then transferred into a clean Eppendorf.

7. 50 µl of hydrolysate was diluted in 8 ml Nerl $H_2O$ (diluting HCl to approximately 38 mM).

8. Spiked in 200 µl of 2× int-pyd. Mixed by inversion. (For 1600 µl 2× int-pyd:160 µl 20× int-pyd+1440 µl Nerl $H_2O$.)

9. Samples were loaded onto SP-Sephadex C25 column (approximately 1×1 cm packed bed volume) that had been equilibrated in water. (Column was pre-charged with NaCl)

10. Loaded flow through once again over column.

11. Washed with 20 ml 150 mM HCl.

12. Eluted crosslinks with 5 ml 2 N HCl into a low binding tube.

13. Dried entire sample in Savant.

F. Analysis of Hydrolysates.
Set-up the following:

| Sample | µl | µl $H_2O$ | µl HFBA |
|---|---|---|---|
| 1. PPG/0 kGy | 18 | 180 | 2 |
| 2. PPG/30 kGy | 59 | 139 | 2 |
| 3. PPG T/0 kGy | 67 | 171 | 2 |
| 4. PPG T/30 kGy | 64 | 134 | 2 |
| 5. PPG SCb/0 kGy | 10 | 188 | 2 |
| 6. PPG SCb/30 kGy | 32 | 166 | 2 |

Results:

According to HPLC analysis, in the presence of PPG 400, the results were nearly identical whether the heart valve had been irradiated or not. The addition of a single stabilizer (trolox C) or a stabilizer mixture produced even more effective results. Gel analysis confirmed the effectiveness of the protection provided by these conditions.

Example 2

In this experiment, the effects of gamma irradiation were determined on porcine heart valve cusps in the presence of 50% DMSO and, optionally, a stabilizer, and in the presence of polypropylene glycol 400 (PPG400).

Preparation of Tissue for Irradiation:

1. 5 vials of PV and 3 vials of atrial valves (AV) were thawed on ice.

2. Thaw media was removed and valves rinsed in beaker filled with PBS.

3. Transferred each valve to 50 ml conical containing PBS. Washed by inversion and removed.

4. Repeated wash 3 times.

5. Dissected out the 3 cusps (valves).

6. Stored in PBS in 2 ml screw top Eppendorf Vials (Eppendorfs) and kept on ice.

Preparation of Stabilizers:

All stabilizers were prepared so that the final concentration of DMSO was 50%.

1 M Ascorbate in 50% DMSO:

Aldrich: cat# 26,855-0, lot# 10801HU 200 mg dissolved in 300 µl $H_2O$. Add 500 µl DMSO. The volume was adjusted to 1 ml with $H_2O$. Final pH was ≈8.0.

1 M Coumaric Acid:

Sigma: cat# C-9008, lot# 49H3600. MW 164.2

Dissolve 34.7 mg in 106 µl DMSO, pH≈3.0

138 µl $H_2O$ was added. Sample precipitated out of solution.

Coumaric went back into solution once pH was adjusted to 7.5 with 1 N NaOH.

1 M n-Propyl Gallate:

Sigma: cat# P-3130, lot# 117H0526. MW 212.2

Dissolve 58.2 mg in 138 µl DMSO.

Add 138 µl $H_2O$. Final pH is 6.5 or slightly lower.

Stabilizer Mixture (SM-a):

1.0 ml 500 mM Ascorbate

500 µl 1 M Coumaric Acid

300 µl 1 M n-propyl gallate 1.2 ml 50% DMSO 3.0 ml

Method:

1.6 ml of a solution (stabilizer mixture or PPG400) was added to each sample and then the sample was incubated at 4° C. for 2.5 days. Valves and 1 ml of the solution in which they were incubated were then transferred into 2 ml irradiation vials. Each sample was irradiated with gamma irradiation at a rate of 1.723 kGy/hr at 3.6° C. to a total dose of 25 kGy.

Hydrolysis of Tissue:

1. Washed each cusp 6 times with acetone in a 2 ml Eppendorf Vial.

2. After final acetone wash, dried sample in Savant (without heat) for approximately 10–15 minutes or until dry.

3. Weighed the samples, transferred them to hydrolysis vials and then added 6 N HCl at a volume of 20 mg tissue/ml HCl:

| Sample ID | Dry Weight (mg) | µl 6 N HCl |
|---|---|---|
| 1. PBS/0 kGy | 11.4 | 570 |
| 2. PBS/25 kGy | 6.0 | 300 |
| 3. DMSO/0 kGy | 6.42 | 321 |
| 4. DMSO/25 kGy | 8.14 | 407 |
| 5. DMSO/SM-a/0 kGy | 8.7 | 435 |
| 6. DMSO/SM-a/25 kGy | 8.15 | 408 |

-continued

| Sample ID | Dry Weight (mg) | μl 6 N HCl |
|---|---|---|
| 7. PPG/0 kGy | 13.09 | 655 |
| 8. PPG/25 kGy | 10.88 | 544 |

SM = Stabilizer Mixture as defined above.

5. Samples were hydrolyzed at 110° C. for approximately 23 hours.
6. Hydrolysates were transferred into Eppendorf vials and centrifuged at 12,000 rpm for 5 min.
7. Sup ematent was transferred into a clean Eppendorf vial.
8. 50 μl hydrolysate was diluted in 8 ml Nerl $H_2O$ (diluting HCl to approximately 37 mM).
9. Spiked in 200 μl of 2× int-pyd. Mixed by inversion. (For 2000 μl 2× int-pyd: 200 μl 20× int-pyd+1.8 ml Nerl $H_2O$.)
10. Samples were loaded onto SP-Sephadex C25 column (approximately 1×1 cm packed bed volume) that had been equilibrated in water. (Column was pre-charged with NaCl)
11. Loaded flow through once again over column.
12. Washed with 20 ml 150 mM HCl.
13. Eluted crosslinks with 5 ml 2 N HCl into a low binding tube. 50 ml 2 N HCl:8.6 ml concentrated HCl adjusted to a volume of 50 ml with Nerl $H_2O$.
14. Dried entire sample in Savant.

Guanidine HCl Extraction and DEAE-Sepharose Purification of Proteoglycans:
4M Guanidine HCl Extraction:
1. Removed all three cusps from gamma irradiation vial and transferred to separate 50 ml conical tube.
2. Washed cusps five times with 50 ml dPBS (at 4° C. over approx. 5 hours) and determined wet weight of one cusp after drying on Kimwipe.
3. Transferred one cusp from each group to 1.5 ml microfuge tube and added appropriate volume of 4M guanidine HCl/150 mM sodium acetate buffer pH 5.8 with 2 μg/ml protease inhibitors (aprotinin, leupeptin, pepstatin A) to have volume to tissue ratio of 15 (see Methods in Enzymology Vol. 144 p.321—for optimal yield use ratio of 15 to 20).
4. Diced cusps into small pieces with scissors.
5. Nutated at 4° C. for ~48 hours.
6. Centrifuged at 16,500 RPM on Hermle Z-252M, at 4° C. for 10 min.
7. Collected guanidine soluble fraction and dialyzed against PBS in 10K MWCO Slide-A-Lyzer overnight against 5 L PBS (3 slide-a-lyzers with one 5L and 5 slide-a-lyzers in another 5L) to remove guanidine.
8. Changed PBS and dialyzed for additional 9 hours at 4° C. with stirring.
9. Collected the dialysate and stored at 4° C.
10. Centrifuged at 16,500 RPM on Hermle Z-252M, at 4° C. for 5 min
11. Removed PBS soluble fraction for DEAE-Sepharose chromatography.

DEAE-Sepharose Chromatography
1. Increased the NaCl concentration of 500 μl of PBS soluble guanidine extract to 300 mM NaCl (Assumed PBS soluble fractions were already at ~150 mM NaCl, so added 15 μl 5M NaCl stock to each 500 μl sample).
2. Equilibrated ~1 ml of packed DEAE-Sepharose (previously washed with 1M NaCl/PB pH 7.2) into 300 mM NaCl/PB pH 7.2 (Note: To make 300 mM NaCl/PB pH 7.2—added 3 ml of 5M NaCl stock to 100 ml PBS).
3. Added 200 μl of 1:1 slurry of resin to 515 μL of GuHCl extracts (both at 300 mM NaCl).
4. Nutated at ambient temperature for ~one hour.
5. Centrifuged gently to pellet resin.
6. Removed "unbound" sample and stored at −20° C.
7. Washed resin 5 times with ~1.5 ml of 300 mM NaCl/PBS pH 7.2.
8. After last wash, removed all extra buffer using a 100 μl Hamilton syringe.
9. Eluted at ambient temperature with three 100 μl volumes of 1M NaCl/PB pH 7.2 and stored at −20° C.

SDS-PAGE:
5–20% gradient gels for analysis of PBS soluble Guanidine HCl extracts and DEAE-Sepharose chromatography.
1. Gel#1: GuHCl extracts/PBS soluble fractions—Toluidine blue and then Coomassie blue stained.
2. Gel#2: DEAE-Sepharose Eluant Fraction#1—Toluidine Blue stained then Coomassie Blue stained.

Quantification of Collagen Crosslinks by HPLC:
Prepared 100–200 μl 1× solution in 1% heptafluorobutyric acid (HFBA).
Injected 50 μl on C18 HPLC column equilibrated with mobile phase.
Spectrofluorometer was set for excitation at 295 nm and emission at 395 nm.
Calculated the integrated fluorescence of Internal-Pyridinoline (Int-Pyd) per 1 μl of 1× solution of Int-Pyd.

Results:
According to HPLC analysis, the major peak represents the Internal-Pyridinoline (int-Pyd) peak. Irradiation in an aqueous environment (PBS) produced pronounced decreases in the smaller peaks. Reduction of the water content by the addition of a non-aqueous solvent (PPG 400) produced a nearly superimposable curve. DMSO was less effective, while DMSO plus a mixture of stabilizers was more effective at preserving the major peak although some minor peaks increased somewhat. The area under the pyd peak for each sample was calculated as shown in the table below. These results confirm the above conclusions and show that the amino acid crosslinks (pyd) found in mature collagen are effectively conserved in the samples containing PPG and DMSO with a scavenger mixture. Gel analysis reflected the major conclusions from the HPLC analysis, with significant loss of bands seen in PBS and retention of the major bands in the presence of non-aqueous solvents.

| Sample | Area of Pyd Peak |
|---|---|
| PBS/ 0 kGy | 94346 |
| PBS/ 25 kGy | 60324 |
| DMSO/ 0 kGy | 87880 |
| DMSO/ 25 kGy | 49030 |
| DMSO/ SM/ 0 kGy | 75515 |
| DMSO/ SM/ 25 kGy | 88714 |
| PPG/ 0 kGy | 99002 |
| PPG/ 25 kGy | 110182 |

Example 3

In this experiment, frozen porcine AV heart valves soaked in various solvents were gamma irradiated to a total dose of 30 kGy at 1.584 kGy/hr at −20° C.

Materials:
1. Porcine heart valve cusps were obtained and stored at −80° C. in a cryopreservative solution (Containing Fetal calf serum, Penicillin-Streptomycin, M199 media, and approximately 20% DMSO).

2. Dulbecco's Phosphate Buffered Saline. Gibco BRL: cat#14190-144, lot#1095027

3. 2 ml screw cap vials. VWR: cat# 20170-221, lot #0359

4. 2 ml glass vials. Wheaton: cat# 223583, lot#370000-01

13 mm stoppers. Stelmi: 6720GC, lot#G006/5511

DMSO. JT Baker: cat# 9224-01, lot# H40630

Sodium ascorbate. Aldrich: cat# 26,855-0, lot 10801HU; prepared as a 2M stock in Nerl water.

8. Fetal calf serum
9. Penicillin-Streptomycin
10. M199 media
11. DMSO

Methods:
Preparation of Solutions
  Freeze Medium:
    Fetal calf serum (FCS) (10%)=50 ml
    Penicillin-Streptomycin=2.5 ml
    M199=QS 500 ml
  2M DMSO
    DMSO=15.62 g
    Freeze Medium=QS 100 ml
  3M DMSO
    DMSO=23.44 g
    Freeze Medium=QS 100 ml
  Preparation of Tissue Placed dissected heart valves (with a small amount of conduit/muscle attached) into glass freezing tubes (label with pencil).

Added 2 ml of freeze medium.
  At 21° C., added 1 ml 2M DMSO solution.
  At 5 minutes, added 1 ml 2M DMSO solution.
At 30 minutes, added 4 ml 3M DMSO solution.
At 45 minutes and 4° C., placed freezing tubes on ice.
At 50 minutes and −7.2° C., seeded bath, which is an alcohol filled tank inside the cryopreservation machine and is used to lower the temperature quickly.
At 55 minutes and −7.2° C., nucleated. Nucleation is a processing step that allows the tissue to freeze evenly and quickly without much ice formation. This is done by placing a steel probe in a liquid nitrogen canister, touching the probe to the outside of the freezing tube at the surface of the solution, waiting for ice formation, shaking the tube and placing the tube in the bath.
At 70 minutes, cooled to −40° C. at 1° C./minute. Removed from bath and placed in canister of liquid $N_2$, and stored in cryogenic storage vessel.

Procedure for Irradiation of Heart Valves:
1. Thawed AV heart valve cusps on wet ice.
2. Pooled cusps into 50 ml tubes.
3. Washed cusps with ~50 ml dPBS at 4° C. while nutating. Changed PBS 5 times over the course of 5 hrs.
4. Transferred cusps into 2 ml screw cap tubes (2 cusps/tube).
5. Added 1.0 ml of the following to two of each of two tubes: dPBS, 50% DMSO and 50% DMSO with 200 mM sodium ascorbate (2M sodium ascorbate stock was diluted as follows: 400 µl (2M)+1.6 ml water+2 ml 100% DMSO).
6. Incubated tubes at 4° C. with nutating for ~46 hours.
7. Transferred solutions and cusps to glass 2 ml vials, stoppered and capped.
8. All vials were frozen on dry ice.
9. Frozen samples were then irradiated at −20° C. at a rate of 1.584 kGy/hr to a total dose of 30 kGy.

Results:
According to HPLC analysis, irradiation in an aqueous environment (PBS) produced decreases in the smaller peaks. Reduction of the water content by the addition of a non-aqueous solvent (20% DMSO) reproduced these peaks more faithfully. Increasing the DMSO concentration to 50% was slightly more effective, while DMSO plus a mixture of stabilizers was very effective at preserving both the major and minor peaks (the additional new peaks are due to the stabilizers themselves). Gel analysis reflected the major conclusions from the HPLC analysis, with significant loss of bands seen in PBS and retention of the major bands in the presence of non-aqueous solvents with and without stabilizers.

Example 4

In this experiment, frozen porcine AV heart valves soaked in various solvents were gamma irradiated to a total dose of 45 kGy at approximately 6 kGy/hr at −70° C.

Materials:
Porcine heart valve cusps were obtained and stored at −80° C. in a cryopreservative solution (Same solution as that in Example 3).
Dulbecco's Phosphate Buffered Saline (dPBS). Gibco BRL: cat#14190-144, lot 1095027

3. 2 ml screw cap vials. VWR: cat# 20170-221, lot #0359
4. 2 ml glass vials. Wheaton: cat# 223583, lot#370000-01
5. 13 mm stoppers. Stelmi: 6720GC, lot#G006/5511
6. DMSO. JT Baker: cat# 9224-01, lot# H40630
7. Sodium ascorbate. Aldrich: cat# 26,855-0, lot 10801HU; prepared as a 2M stock in Nerl water.
8. Polypropylene glycol 400 (PPG400). Fluka: cat#81350, lot#386716/1

Methods:
Cryopreservative Procedure is the same as that shown in Example 3.

1. Thawed AV heart valve cusps on wet ice. Dissected out cusps and washed the pooled cusps 6 times with cold PBS.
2. Dried each cusp and transferred cusps into 2 ml screw cap tubes (2 cusps/tube).
3. Added 1.2 ml of the following to two of each of two tubes: dPBS, dPBS with 200 mM sodium ascorbate, PPG400, PPG400 for rehydration, 50% DMSO and 50% DMSO with 200 mM sodium ascorbate (2M sodium ascorbate stock was diluted as follows: 400 µl (2M)+1.6 ml water+2 ml 100% DMSO).
4. Incubated tubes at 4° C. with nutating for ~46 hours.
5. Replaced all solutions with fresh solutions (with the following exception: for one PPG400 set, PPG400 was removed, the cusp washed with PBS+200 mM ascorbate, which was then removed and replaced with fresh PBS+200 mM ascorbate).
6. Incubated tubes at 4° C. with nutating for ~46 hours.
7. Changed the solution on the PPG400 dehyd./PBS+ ascorbate rehydration cusps prepared in step 5.
8. Incubated tubes at 4° C. with nutating for ~6 hours.
9. Transferred solutions and cusps to glass 2 ml vials, stoppered and capped.
10. All vials were frozen on dry ice.
11. 5Frozen samples were then irradiated at −70° C. at a rate of 6 kGy/hr to a total dose of 45 kGy.

Results:
According to HPLC analysis, irradiation in an aqueous environment (PBS) resulted in changes in the minor peaks and a right shift in the major peak. The inclusion of various non-aqueous solvents, reduction in residual water, and the addition of stabilizers produced profiles that more closely matched those of the corresponding controls. Gel analysis showed a significant loss of bands in PBS, while the other groups demonstrated a significant retention of these lost bands.

When comparing the results from Example 4 to the results from Examples 1, 2, and 3, it becomes apparent that lowering the temperature for the gamma irradiation usually results in a decrease in the amount of modification or damage to the collagen crosslinks. One illustration of this temperature dependence is the sample containing 50% DMSO and ascorbate, in which the additional peaks are markedly decreased as the temperature is lowered from −20° C. to −80° C. It is also clear that reducing residual water content by replacing it with a non-aqueous solvent results in less damage or modification, as does adding the stabilizers shown.

Example 5

In this experiment, the protective effect of the absence or presence of a stabilizer cocktail on frozen porcine ACL samples, which were gamma irradiated to a total dose of 45 kGy at approximately 6 kGy/hr at −80° C., was evaluated.
Materials:
Porcine ACL samples were obtained and placed in 15% DMSO or 15% DMSO containing 100 mM ascorbate, 100 mM deferoxamine, and 22 mM ergothioneine and incubated for 1 hour at 37° C. with agitation and then at 4° C. for 24 hours. The ACL samples were quick frozen in ethanol, dry-ice bath and then stored at −80° C. until irradiation
Methods:
ACL samples were sent to the irradiator on dry ice.
Gamma irradiation was performed at NIST at 5.18 kGy/hour to a total dose of 45 kGy at an average temperature of −75° C. The 0 kGy controls were maintained on dry ice. Irradiated samples were as follows:
4 M Guanidine—0.5 M sodium acetate, pH 5.8 extraction and SDS-PAGE;
Pepsinolysis of guanidine residue and SDS-PAGE;
CNBr digest of pepsin residue and SDS-PAGE;
SDS-PAGE of CNBr digest residue; and
Hydrolysis and evaluation of pyridinoline crosslinks by HPLC.
Results:
Fewer proteins overall were extracted by guanidine/acetate following irradiation to 45 kGy, and of those that were extracted, there was significantly less protein in the 45 kGy sample than the control sample subjected to 0 kGy of irradiation. Additionally, there were a series of bands around 205 kD that were absent from the 5 kGy sample. The top two of the four bands were detected, however, in the 45 kGy sample with the cocktail. There are three darker staining bands that run just above the 119 kD marker, the top band of which appears to be sensitive to gamma irradiation. Additionally, there are a series of bands around 205 kD that are absent from the 45 kGy sample.

Also, the SDS-PAGE analysis of the pepsin-solubilized component of the guanidine/acetate residue indicates that more material was extracted by pepsinolysis following 45 kGy of gamma irradiation compared to the 0 kGy controls. There also appeared to be a significant difference between the 0 and 45 kGy samples in the region of 52 to 119 kD. Additionally, there is evidence of increased smearing and higher molecular weight material that does not enter the gel in the 45 kGy sample lanes. There also does not seem to be a gross difference between the 45 kGy samples with or without the cocktail.

Further, no differences appeared among the samples following CNBr cleavage of the residue left after pepsin digestion. HPLC analysis of the Pyridinoline crosslinks indicated that there was about a 20% loss in crosslink of the 45 kGy samples compared to the 0 kGy sample. The peak profiles of the samples containing cocktail were broader and there appeared to be a loss of symmetry. The cocktail or ratio of tissue to HCl during may also affect the hydrolysis.

Pretreatment of the ACL tissue with the AED stabilizer cocktail provided minimal protection to radiation-induced damage. SDS-PAGE of the guanidine extracted material indicated that several higher molecular weight proteins are sensitive to gamma irradiation and therefore might serve as markers for later evaluation.

Example 6

In this experiment, the effect of gamma irradiation on frozen porcine ACL samples soaked in the absence or presence of a stabilizer was evaluated
Materials:
Porcine ACL samples with the following stabilizers were prepared:
200 mM sodium ascorbate (Spectrum S1329 QP 0839) in water;
100 mM thiourea (Sigma T8656, 11K01781) in water;
200 mM L-histidine (Sigma H8776, 69H1251) in PBS;
500 mM D(+)-trehalose (Sigma T9531, 61K7026) in water;
5 mg/mL ergothionine (Sigma E7521, 21K1683) in water;
0.01 M poly-Lysine (Sigma, MW 461);
PPG for 1 hour at 37° C., then removed and soaked in a PPG cocktail of 100 $\mu$M trolox C (Aldrich 23,881-3, 02507TS, 53188-07-01) in DPBS, 100 mM lipoic acid (Calbiochem 437692, B34484), 100 mM coumeric acid (Sigma) in ethyl alcohol and 100 mM n-propyl gallate (Sigma P3130, 60K0877) in ethyl alcohol; and
No stabilizers added (water only).
Methods:
ACL samples were prepared by cutting each sample in half in the longitudinal direction;
Porcine ACL samples were obtained and placed in one of the stabilizers for 1 hour in a shaking incubator at 37° C.;
Next, the samples were dehydrated for 1 hour at 37° C. in PPG 400;
The samples were then placed at 4° C. with the stabilizer previously used for an additional 1 hour, and then fresh stabilizers were added and soaking occurred for 3 days at 4° C. Then the samples were decanted and freeze dried. Fresh stabilizers were also added prior to freeze drying.
ACL samples were freeze dried, then gamma irradiation was performed at NIST with 0 and 45 kGy of gamma irradiation at 1.677 kGy/hr.
Irradiated samples were as follows:
Control (ACL) in water;
ACL+200 mM sodium ascorbate, pH 7.63;
ACL+100 mM thiourea, pH 6.63;
ACL+200 mM L-histidine, pH 8.24;
ACL+500 mM trehalose, pH 5.24;
ACL+5 mg/mL ergothionine, pH 6.0;
ACL+0.01 M poly-Lysine, pH 5.59; and
ACL dehydrated+PPG cocktail (100 $\mu$M trolox C, 100 mM lipoic acid, 100 mM courmeric acid and 100 mM n-propyl gallate), pH 5.24.
Guanidine HCL extraction was done with 4 M GuHCl in 0.5 NaOAC pH 5.8 and 5 mM EDTA, 10 mM NEM, 5 mM Benzamidine and 1 mM PMSF to a final concentration of 100 mg/ml of wet tissue weight/ml of extraction buffer. The samples were incubated at 4° C. on a nutator for 2 days.

Pepsin digestion was done by first centrifuging these extracts, then transferring the remaining pellets into a 2 ml tube. The pellets were then washed 3 times with 0.5 M HOAc. Pepsin was added at 1:10 of enzyme:tissue in 0.5 M HOAc and incubated at 4° C. overnight.

For pepsin-digested supernatant, NaCl form 5 M stock solution was added to a final concentration of 1M. The supernatants were centrifuged and collagen gel pellets were resuspended in 1 ml of 0.5 M HOAc with gentle mixing at 4° C.

Performed DEAE chromatography on dialysates of Guanidine extracts of samples. Eluants from the DEAE column were subjected to SDS-PAGE and visualized by staining with Toluidine Blue.

A BCA assay was performed on the dialysates of the PPG+cocktail guanidine extracted samples to determine the total protein concentration in the samples.

Extracted PPG+cocktail treated samples using Urea/SDS/β-Me extraction buffer. The extractible noncollagenous proteins were analyzed by SDS-PAGE under reducing conditions.

Results:

The ACL samples were rehydrated with water for a few hours at room temperature, where a measured length of each ligament was cut and weighed. The weights of the cut pieces is as follows:

| Sample | 0 kGy (mg) | 45 kGy (mg) |
|---|---|---|
| No stabilizer | 134.5 | 150.45 |
| sodium ascorbate | 171.95 | 148 |
| thiourea | 288.6 | 183.06 |
| L-histidine | 229.3 | 226.54 |
| D(+)-trehalose | 260 | 197.5 |
| ergothionine | 165.14 | 132.68 |
| poly-Lysine | 289.34 | 164.88 |
| PPG cocktail | 114.5 | 83.93 |

From the SDS-PAGE of pepsin digest, the cocktail treated ACL showed the best recovery compared to the other stabilizers. The HMW bands were protected after irradiation in the presence of the cocktail mix.

For the purified pepsin-digested collagen, the PPG dehydration and rehydration with cocktail showed the best recovery by SDS-PAGE. The yield was about 88% for the cocktails comparing to 32% for the control. However, some of the HMW bands were destroyed by irradiation even in the presence of the cocktails. These other stabilizers were not effective in protecting the collagen in this experiment.

The turbidity of the collagen appeared to be lower in the presence of the cocktail with a lower rate of fibril formation compared to the un-irradiated collagen.

SDS-PAGE of the guanidine extracts indicated severe damage to the extractable proteins following irradiation to 45 kGy as compared to the corresponding 0 kGy control The addition of the various stabilizers gave variable results. The 0 kGy controls differed from one another which either reflects the efficiency of their extraction in the presence of the various stabilizers or is an artefact of the dialysis. Trehalose and poy-lysine provided the least protection. Ascorbate and histidine provided the most promising results for protecting a broad spectrum of the proteins, while ergothionine showed good protection of proteins in the lower 2/3 of the gel. The cocktail provided protection to the proteins in the region above the 119 kD marker. However, the very high molecular weight proteins were not well preserved by any of the stabilizers.

Using DEAE chromatography, the proteoglycan profile appeared varied and inconsistent from sample to sample and from control to control. It is unclear whether the stabilizers were affected. It is clear, however, that there is a high molecular weight proteoglycan (>200 kD) that was purified in several of the samples. Most of the samples had a band that migrated similar to that of the recombinant human decorin. However, it is not clear whether it is porcine decorin.

Using BCA and SDS-PAGE on the PPG+Cocktail sample, guanidine extracts were evaluated based on SDS-PAGE of equal protein load. The protein concentrations were as follows:

| | |
|---|---|
| fdL/PPG + C/0 | 1270 ng/μL |
| fdL/PPG + C/45 | 249 ng/μL |

Although there appears to be significantly less protein in the 45 kGy sample based on concentration alone, there appears to be a similar amount of total protein when the volume was taken into consideration where the 45 kGy sample appears diluted. Additionally, the SDS-PAGE analysis shows loss of specific protein bands with other bands appearing to be less sensitive to radiation. Densitometry was performed on two different protein bands, as follows:

| | | |
|---|---|---|
| background | 4.52 | |
| 0 kGy | 50.26 | |
| 45 kGy | 26.87 | percent of 0 kGy: 53.5% |
| background | 2.33 | |
| 0 kGy | 70.26 | |
| 45 kGy | 50.54 | percent of 0 kGy: 71.9% |

It is appears that the different recoveries observed are due to differences in sensitivity to radiation or due to a difference in extraction ability. For example, the loss observed in the 45 kGy sample might be due to a differential loss (i.e.—damage) of the proteins or might be due to radiation-induced cross linking that results in a different ability of various proteins to be extracted.

Using Urea/SDS/β-Me extraction the initial difference in guanidine extraction of the PPG+cocktail samples can be observed. It appears that the PPG+cocktail treatment resulted in significant protection of the extractible proteins at 45 kGy of gamma irradiation compared to the 45 kGy sample without treatment. However, it is noted that the PPG+cocktail sample did not rehydrate, but the lack of rehydration appears to be irradiation independent and therefore caused by some component or combination of components in the treatment, which was investigated in Example 7, as follows.

Example 7

In this experiment, the protective effect of the PPG+cocktail treatment of Example 6 was observed to determine whether the ACL sample was adversely affected due to the lack of rehydration.

Materials:
α-Lipoic Acid (Calbiochem #437692, lot B34484);
Trolox C (Aldrich #23,881-3, lot 02507TS);
n-Propyl Gallate (Sigma #P-3130, lot 60K0877);

p-Coumaric Acid (Sigma #C-9008, lot 49H3600);
Polypropylene Glycol P400 (Fluka #81350, lot 386716/1);
5 mL tubes;
1 eft ACL (received from RadTag Technologies);
Ethyl Alcohol (Burdick & Jackson, #AH090-4, lot BX488)

Methods:

The ACL samples was sectioned and dehydrated in PPG for 2 hours @ 37° C. with shaking.

Components of the stabilizer cocktail were made individually by making the stocks, then diluting them with 40% ethanol (which alone does not prevent rehydration of the tissue), where the individual stabilizers/controls were as follows:

2 mM Trolox C in PBS (diluted 1:20 in 40% ethanol, final of 100 μM)
1 M propyl gallate dissolved in ethanol (diluted 1:10, final of 100 mM in 40% ethanol)
0.5 M coumaric acid in ethanol (diluted 1:5, final 100 mM in 40% ethanol)
0.5 M lipoic acid initially dissolved in NaOh and then the volume and pH were adjusted to neutral (diluted 1:5 in 40% ethanol)
40% ethanol
water Following a 2 hour incubation in PPG, the tissue was removed and blotted to remove excess PPG and 2 mL of the individual stabilizers/controls (a–f) were added.

Samples were then placed on a shaker at 4° C. and allowed to rehydrate overnight.

Results:

The ACL tissue samples were rehydrated to a normal appearance except the sample treated with PPG and coumaric acid. The coumaric acid was then tested without the PPG, but still did not result in a normal process by rehydration and instead led to adverse properties of the ACL tissue sample which appeared dehydrated and sticky to the touch.

Example 8

In this experiment, the protective effect of a cryopreservative on a gamma irradiated regulated or quick freeze dried ACL at −80° C. was evaluated.

Materials:

Edmonton cryopreservative media (M199, 10%FCS, Penicillin-Streptomyocin, 2 M DMSO Modified VS55 cryoprotectant (100 mM trehalose, 15 mM $KH_2PO_4$, 42 mM $K_2HPO_4$, 15 mM KCl, 10 mM $NaHCO_3$, 150 mM mannitol, 24.2% DMSO, 16.8% 1,2-propanediol, 14% formamide). See U.S. Pat. No. 6,194,137 B1.

200 mM sodium ascorbate

Methods:

ACL samples were submerged in either the Edmonton or VS 55 media.

Samples were frozen by reducing the temperature 1° C. per minute to −40° C. in the freeze dryer and then placing the samples at −80° C. (regulated freeze) or freezing in a dry ice-ethanol bath (quick freeze).

Irradiations were performed at NIST on dry ice using 5.2 kGy/h to a total dose of 50 kGy.

The following analyses were performed:
Gnd-HCL extraction and SDS-PAGE;
Urea/SDS/β-Me extraction and SDS-PAGE;
Collagenase digestion of Gnd-HCL residue and SDS-PAGE;
Collagen purification and SDS-PAGE; and
DEAE chromatography and SDS-PAGE.

Results:

Purification of proteoglycans by DEAE chromatography appeared to show that the cryopreservative treatment influenced the ability of the proteoglycans to be purified. All samples submerged in Edmonton CP had a similar profile, but varied in intensity. On the other hand, treatment with VS55 gave poor recovery of proteoglycans under the quick freezing regimen, whereas the regulated freeze resulted in good recovery except in the sample containing ascorbate.

A table of the percent recovery of the major band observed by SDS-PAGE, comparing the irradiated sample to its corresponding control for the guanidine extracts, is given below. For the samples treated with CP, those samples in which 200 mM ascorbate was added, had a lower percent recovery than the sample without ascorbate. And, the quick freeze gave better recovery than the regulated freeze. Whereas, with the mVS55 treated samples the regulated freeze had better recovery based on the densitometry of single band. However, by visual examination, the overall total protein extracted from the regulated freeze appeared to be less than that extracted from the quick freeze. Additionally, the exaggerated percent recoveries (>100%) are likely an artefact of smearing and the absence of some of the higher molecular weight proteins. However, the mVS55 does seem to give better recovery of these high molecular weight proteins (around 205 kDa) in the irradiated samples than other irradiated samples without mVS55.

The gels of the Urea/SDS/β-Me extractible proteins appear to be consistent with the results observed with the guanidine extraction. Densitometry was not performed on these samples as the smearing observed in the irradiated samples leads to inaccurate readings. To that end, the obvious presence of the smearing indicates damage to tissue proteins following irradiation.

| | Major Band Edmonton CP | | | |
|---|---|---|---|---|
| | Dens. | Blank Sub. | % Recovery | |
| Quick Freeze | | | | |
| Blank | 27.71 | 0 | | |
| 0 kGy | 137.3 | 109.59 | 100 | kGy |
| 50 kGy | 138.75 | 111.04 | 101 | kGy |
| Asc. 0 kGy | 137.05 | 109.34 | 100 | 0 kGy |
| Asc. 45 kGy | 122.75 | 95.04 | 87 | 45 kGy |
| Regulated Freeze | | | | |
| Blank | 27.71 | 0 | | |
| 0 kGy | 135.98 | 108.27 | 100 | kGy |
| 50 kGy | 104.54 | 76.83 | 71 | kGy |
| Asc. 0 kGy | 137.14 | 109.43 | 100 | 0 kGy |
| Asc. 45 kGy | 95.79 | 68.08 | 62 | 45 kGy |

From the SDS-PAGE, purified pepsin-digested collagen from the VS55 cryopreservatives without ascorbate showed the best recovery, as illustrated in the following table:

| Regulated Freezing | | |
| --- | --- | --- |
| Density of a chain Collagen | | % Recovery |
| Blk | 15.01 | 0 |
| VS55/0 kGy | 46.39 | 31.38 | 100 |
| VS55/50 kGy | 51.72 | 36.71 | 117 |
| VS/A/0 kGy | 53.53 | 38.52 | 100 |
| VS/A/50 kGy | 42.79 | 27.78 | 72 |
| CP/0 kGy | 58.7 | 43.76 | 100 |
| CP/50 kGy | 43.92 | 28.91 | 66 |
| CP/A/0 kGy | 80.98 | 65.97 | 100 |
| CP/A/50 kGy | 56.02 | 41.01 | 62 |

Turbidity results for pepsin-digested collagen from ACL in VS55 cryopreservative did not correlate well with the SDS-PAGE data for regulated freeze and quick freeze ACL samples. The collagen from irradiated ACL in VS55 did not form fibril as expected, probably due to the presence of degraded proteins and loss of high molecular weight protein bands after irradiation (which interfere with the assay). For other cryopreservatives turbidity results correlated quite well with the SDS-PAGE results for quick freeze and regulated freeze ACL samples.

Example 9

This experiment was to determine whether ethanol dehydration or drying ACL will help to remove water and whether a rehydration process would deliver cocktail of antioxidants inside ACL tissue to protect it from γ-irradiation at 4° C. with 50 kGy.

Materials:
1. 2 mM trolox C [Aldrich 23,881-3, 02507TS, 53188-07-01] in DPBS
2. 0.5M lipoic acid [Calbiochem 437692, B34484] in 100% ethanol
3. 0.5 M coumeric acid [Sigma C4400] in ethyl alcohol
4. 1M n-propyl gallate [Sigma P3130, 60K0877] in ethyl alcohol
5. 10 mg/ml Ergothionine [Sigma E7521, 21K1683] in water.

Samples were prepared by cutting ACL in small chunk and used for irradiation as following:
1. Control (ACL)
2. Cocktails (100 μM troloxC, 100 mM coumeric acid, 100 mM lipoic acid, 100 mM n-propyl gallate)
3. Cocktails+5 mg/ml ergothionine.

Methods:
1. Six pieces of ACL were dried overnight to remove water.
2. Another six pieces were soaked in 25% ethanol for 2 hr at room temperature (rt), then 50% ethanol for 1 hr at rt and 75% ethanol for overnight at rt.
3. Soaked another 6 pieces of ACL in 100% ethanol for 6 hr at rt and these ACLs were incubated with either cocktails or modified cocktails solutions for 2 hr with shaking in a shaking incubator at 37° C. After 2 hr incubation, these ACL tubes were decanted and fresh solution of anti-oxidants were added to each ACL containing tubes and incubated for overnight at 4° C.
4. All the tubes were freeze-dried for 2 days.
5. The samples were irradiated with 0 and 50 kGy at 1.656 kGy/hr at NIST.
6. The ligaments were rehydrated with water for a few hours at rt.
7. Washed extensively with DPBS.

8. For ethanol dehydration ACL samples, rehydration was repeated by washing with the gradient of 75%, 50%, and 25% ethanol. Then washed with DPBS extensively.
9. Cut a small piece from each sample and weighed all of the cut pieces.

| | |
| --- | --- |
| a) ETOH | 0 kGy = 25.12 mg |
| | 45 k = 10.5 mg |
| b) ETOH/Cocktails | 0 kGy = 25.6 mg |
| | 45 kGy = 32.4 mg |
| c) ETOH/modified | 0 kGy = 30.45 mg |
| | 45 kGy = 30.3 mg |
| d) FD | 0 kGy = 30.1 mg |
| | 45 kGy = 16.3 mg |
| e) FD/cocktails | 0 kGy = 33.3 mg |
| | 45 kGy = 31.51 mg |
| f) FD/modified | 0 kGy = 30 mg |
| | 45 kGy = 26.5 mg |

10. ACLs were digested with pepsin and collagen was purified by salt precipitation.
11. Collagen gel pellets were resuspended in 1 ml of 0.5 N HOAc with gently mixing at 4° C.
12. The pepsin-digested collagens for control and cocktails treated ACL were dialyzed against 5 mM HOAc for overnight.
13. Determined the OD 218 nm for each collagen preparation.
14. Turbidity assay was performed for these collagens.

Results:

The purified pepsin-digested collagen for ethanol dehydration of ACL with cocktails without ergothionine showed the best recovery compared with cocktails with ergothionine by SDS-PAGE. The yield was 88% for the cocktails with ethanol dehydration comparing to 83% for freeze-dried dehydration. The cocktails of scavengers and ergothionine was a little less effective than that of cocktails alone.

Ethanol dehydration seemed to give a little bit better recovery than the freeze-dried dehydration process for ACL.

Example 10

This experiment was to determine whether high salt, low salt, neutral pH and low pH treated ACL will help to deliver stabilizers into ACL tissue to protect it from γ-irradiation at −80° C. with 50 kGy.

Method
1. Prepared stock solution 2M sodium ascorbate (Spectrum S1349, Lot#QP0839) in water. Samples were prepared with the following:
   a) DPBS
   b) DPBS/200 mM sodium ascorbate
   c) 0.5N HOAc
   d) 0.5N HOAc/200 mM sodium ascorbate
   e) 20 mM sodium phosphate pH 7.6
   f) 20 mM sodium phosphate pH 7.6/200 mM sodium ascorbate
   g) 20 mM sodium phosphate pH 7.6/1M NaCl
   h) 20 mM sodium phosphate pH 7.6/1M NaCl/200 mM sodium ascorbate.
2. These samples were irradiated with 0 and 50 kGy at 1.53 kGy/hr at NIST.
3. A small piece was cut from each sample and weighed as follows:

| | |
|---|---|
| a) DPBS | 0 kGy = 32.7 mg |
| | 45 k = 10.7 mg |
| b) DPBS/Asc | 0 kGy = 25.12 mg |
| | 45 kGy = 26 mg |
| c) 0.5 N HOAc | 0 kGy = 37.3 mg |
| | 45 kGy = 35.5 mg |
| d) 0.5 N HOAc/Asc | 0 kGy = 21.2 mg |
| | 45 kGy = 41.4 mg |
| e) 20 mM $PO_4$ | 0 kGy = 22.87 mg |
| | 45 kGy = 36.3 mg |
| f) 20 mM $PO_4$/Asc | 0 kGy = 24 mg |
| | 45 kGy = 18.04 mg |
| g) 20 mM $PO_4$/NaCl | 0 kGy = 21.41 mg |
| | 45 kGy = 21.2 mg |
| h) 20 mM $PO_4$/NaCl/Asc | 0 kGy = 33.76 mg |
| | 45 kGy = 21 mg |

4. ACL were digested with pepsin and collagen purified by precipitating with salt.
Results:

The purified pepsin-digested collagen from ACL irradiated at −80° C. with 0.5N HOAc pH 3.4 showed the best recovery compared with 20 mM sodium phosphate pH 7.6 with or without 1M NaCl or PBS alone by SDS-PAGE. The yield at 50 kGy was 83% with ascorbate and 73% without ascorbate. ACL irradiated with 20 mM sodium phosphate pH 7.6 without salt yielded good recovery at 75% and 60% in the presence and absence of ascorbate, respectively. ACL irradiated with high salt showed the worst recovery only 40% with or without ascorbate.

The turbidity assay appeared to have the collagen isolated from the ACL samples. Also, the washing of the collagen gel pellet after salt precipitation seemed to help. Collagen isolated from ACL irradiated with 0.5N HOAc showed the best results, which correlated with SDS PAGE results. However, the turbidity curves of collagens from ACL irradiated in the presence of ascorbate did not quite correlate with SDS PAGE results, which showed better recovery than that of ACL irradiated under conditions without ascorbate, which may be caused because the ascorbate may not have been completely removed from the ACL sample.

Also, it appeared that the ACL sample soaking with 0.5N HOAc caused the tissue to swell and become larger than its original size. After washing with DPBS, however, the tissue appeared to change back to its original size.

Example 11

This experiment was to determine whether alcohols can protect ACL tissue samples from γ-irradiation at −80° C. with 50 kGy.
Methods:
1. ACL samples were prepared by preparing small portions of ACL sample with the following:
 a) ethanol
 b) 1,2-propanediol
 c) 2,3-butanediol
2. These samples were then incubated with different alcohols for 2 hr in a shaking incubator at 37° C.
3. After 2 hr incubation, these ACL tubes were decanted and fresh solutions were added to each ACL containing tubes and incubated overnight at −80° C.
4. These samples were irradiated with 0 and 50 kGy at 1.53 kGy/hr at NIST.
5. These ligaments were washed extensively with DPBS. Small pieces from each sample were cut, then weighed as follows:

| | |
|---|---|
| a) DPBS | 0 kGy = 22.9 mg |
| | 50 k = 16.43 mg |
| b) DPBS/Asc | 0 kGy = 47.1 mg |
| | 50 kGy = 21.85 mg |
| c) 0.5 N HOAc | 0 kGy = 32.5 mg |
| | 50 kGy = 30.8 mg |

6. ACL were digested with pepsin and collagen purified by precipitating with salt.
7. Turbidity assay was performed for these collagens using at [1 mg/ml].
8. Ran 10 μg of each purified pepsin-digested collages on 4–12% gel and quantified both alpha 1 and alpha 2 chains.
Results:

The purified pepsin-digested collagen from ACL irradiated at −80° C. with ethanol or butanediol showed good recovery. The yields for 50 kGy ACL collagen were 77% and 88% based on the densitometry of alpha 1 and 2 chains of collagen, respectively. Some of the HMW bands (possible β and γ chains of collagen) were completely destroyed by irradiation. Although the recoveries were good, the recovery of collagen isolated from ACL irradiated in the presence of 20 mM P04 and ascorbate was still better.

A turbidity assay was performed for the collagen isolated from these ACL samples. Correlation was found between the ACL collagen before and after irradiation. Collagen isolated from ACL irradiated in the presence of alcohol and propanediol could not form fibrils even at higher collagen concentration 0.5 mg/ml comparing to normal used 0.25 mg/ml concentration.

Example 12

This experiment was to compare the effects of gamma irradiation on ACL samples that were subjected to three different types of preservation: fresh frozen, freeze dried, or solvent-dried, as these methods of preservation are used by various tissue banks/processors.
Method:
1. Tissue cross sections were sliced and weighed.

| | |
|---|---|
| a. acl/fresh/−80/0 | 330.0 g |
| b. acl/fresh/−80/45 | 335.9 mg |
| c. acl/fd/−80/0 | 286.2 mg |
| d. acl/fd/−80/45 | 272.4 mg |
| e. acl/ad/−80/0 | 298.9 mg |
| f. acl/ad/−80/45 | 274.3 mg |

2. Fresh ligaments were placed in 2 mL serum vials and frozen in a dry ice-ethanol bath and then stored in a −80° C. freezer until irradiation.
3. The freeze-dried ligaments (fd) were placed in 2 mL serum vials for freeze drying. The freeze dried tissue was then stored in a −80° C. freezer until irradiation.
4. The acetone-dried ligaments were placed in 5 mL conical vials and 5 mL acetone was added. The samples were placed at 4° C. on the nutator. The acetone was changed every hour for 4 hours and the 5th acetone wash went overnight. The next morning the samples were removed from the acetone and blotted dry with a Kimwipe. The dried ligaments were placed in a 2 mL serum vial and the residual acetone was allowed to evaporate in a hood overnight. The acetone-dried ligament appeared to be dehydrated and shriveled. The samples were stored in the −80° C. freezer until irradiation.

5. All samples were irradiated at NIST to 45 kGy on dry ice (−72° C.) at 1.5 kGy/h. The 0 kGy controls traveled and were stored on dry ice at NIST.
6. Rehydrated tissue with 2 mL PBS for 1.5 h at 4° C. with shaking on the Nutator.
   a. All looked rehydrated except for the acetone-dried tissues that still appeared shriveled and hard to the touch.
   b. Transferred tissues to conical vials with 20 mL PBS and left overnight at 4° C. with shaking on the Nutator.
   c. All tissues rehydrated.
7. Extracted noncollagenous protein with Urea/SDS/B-Me extraction buffer. Analyzed samples by SDS-PAGE (4–20% gradient) under reducing conditions.
8. Pyd-cross link recovery was determined.

Results:

Gamma irradiating ACL's to 45 kGy at low temperature resulted in better recovery than irradiating freeze-dried ACL's to 45 kGy at 4° C. In addition, the freeze-dried sample irradiated to 45 kGy in this study resulted in a better recovery of noncollagenous proteins than was observed for the freeze-dried 45-kGy-sample irradiated at 4° C.

This study indicates that irradiating fresh frozen tissue yields better recovery of the noncollagenous proteins than is observed when the tissue has been dehydrated by freeze drying or solvent drying (acetone) prior to irradiating as indicated by the extensive smearing observed on the gel. Densitometry indicated that the major band seen on the gel was similar in all the 0 kGy controls.

Example 13

In this experiment, the effects of gamma irradiation an porcine ACL treated with various stabilizers was investigated.

Preparation of Antioxidant Stock Solutions
The following stock solutions were prepared:
2M sodium ascorbate in water (Spectrum S1349 QP 0839)
2 mM trolox C in DPBS(Aldrich 23,881-3, 02507TS, 53188-07-01)
0.5M lipoic acid (Calbiochem 437692, B34484)
0.5M coumaric acid in ethyl alcohol (Sigma)
1M n-propyl gallate in ethyl alcohol (Sigma P3130, 60K0877)
0.2M L-histidine in PBS (Sigma H8776, 69H1251)
2M D-(+)-trehalose in water (Sigma T9531, 61K7026)
10 mg/ml ergothionine in water (Sigma E7521, 21K1683)
0.04M poly-lysine (Sigma, MW=461)
1M thiourea (Sigma T8656, 11K01781)

Preparation of Ligament Samples

Samples were prepared by cutting ACL in half longitudinally. The lengths of each ACL were measured and used for irradiation. The samples were placed in tubes with the following conditions:
1. ACL in water (Control)
2. ACL+200 mM sodium ascorbate, pH 7.63
3. ACL+0.1M thiourea, pH 6.64
4. ACL+200 mM histidine, pH 8.24
5. ACL+500 mM trehalose, pH 5.36
6. ACL+5 mg/ml ergothionine, pH 6.0
7. ACL+0.01M poly-lysine, pH 5.59
8. ACL dehydrated+(100 µM trolox C, 100 mM coumaric acid, 100 mM lipoic acid, 100 mMn-propyl gallate), pH 5.24

Methods:

ACL's 1–7 described above were incubated for about 1 to about 2 hours with shaking in a shaking incubator at 37° C. For the dehydration (8), the ACL was incubated with polypropylene glycol 400 (PPG400) for 1 hour at 37° C. The PPG400 treated ACL was incubated with the antioxidant mixture described above for 1 hour at 37° C. After about 2 hours of incubation, the ACL tubes were decanted and fresh solutions of antioxidants, or water for 1, were added to each ACL tube. Following this, the tubes ACL's were incubated for 3 days at 4° C., decanted and freeze-dried.

The samples were irradiated with 0 kGy and 45 kGy at 1.677 kGy/hr.

The samples were rehydrated with water for a few hours at room temperature. The length of the ACL's was measured and a small piece was cut from each irradiated ACL. The cut pieces were weighed with the following results:

| Sample Number | 0 kGy (mg) | 45 kGy (mg) |
|---|---|---|
| 1 | 134.5 | 150.45 |
| 2 | 171.95 | 148 |
| 3 | 288.6 | 183.06 |
| 4 | 229.3 | 226.54 |
| 5 | 260 | 197.5 |
| 6 | 165.14 | 132.68 |
| 7 | 289.34 | 164.88 |
| 8 | 114.5 | 83.93 |

Guanidine HCl Extraction

The ACL samples were extracted with 4M GuHCl in 0.5M NaOac, pH 5.8, and 5 mM EDTA, 10 mM, 5 mM benzamidine and 1 mM PMSF for a final concentration of 100 mg/ml or wet tissue weight/ml of extraction buffer. The samples were incubated on the nutator for 2 days at 4° C.

Following incubation, the extracts were centrifuged using a tabletop centrifuge and the pellets were transferred into 2 ml tubes and washed 3 times with 2 ml of 0.5M HOAc. Pepsin was added to the pellets at a 1:10 ratio of enzyme to tissue in 0.5N HOAc. The samples were incubated at 4° C. overnight and another portion of pepsin was added to each pellet. The samples were incubated on the nutator at 4° C. overnight.

The samples were centrifuged and washed 3 times with 100 mM Tris, pH 8.0, and 20 mM CaCl$_2$. Trypsin was added at a 1:20 ratio of enzyme to wet weight. The samples were mixed and incubated at 37° C. overnight.

To the pepsin-digested supernatant, NaCl from 5M stock solution was added to a final concentration of 1M. The supernatants were centrifuged for 15 minutes at 22,000 g in a cold room. Collagen gel pellets were resuspended in 1 ml of 0.5N HOAc with gentle mixing at 4° C.

The pepsin digested collagens for the samples were dialyzed against 5 mM HOAc overnight. Determined the OD 218 nm for each collagen preparation. A turbidity assay was performed for these collagens using purified pepsin-digested collagen as a control.

Results:

From the SDS-PAGE of the pepsin digest, the antioxidant cocktail treated ACL (8) showed the best recovery compared to other antioxidants. The HMW bands were protected after irradiation in the presence of cocktails. The trypsin digest did not provide any conclusive results.

For the purified pepsin-digested collagen, the PPG dehydration and rehydration with scavenger cocktails showed the best recovery by SDS-PAGE. They yield was 88% for the cocktails compared to 32% for the control (1).

Using PPG400 for dehydration of the ACL irreversibly changed the morphology of the ACL, even after rehydration.

Example 14

Method:

Samples of human bone powder were gamma irradiated to a total dose of 20 kGy at rates of 0.19, 5 and 30 kGy/hr on dry ice. A fourth control sample was not irradiated. After irradiation, the three samples and control were ground to 75–500 µm particle size and demineralised by decalcifying for 10 hours in 10% formic acid. The ground samples were extracted with guanidine hydrochloride and 5 µg total protein from each extraction were assayed by RP-HPLC.

As the rate of irradiation increased, there was an increase in the amount of collagen breakdown products.

Example 15

Samples of human bone were gamma irradiated at dose rates of 0.2 or 0.6 kGy/hr to total doses of 30, 40 or 50 kGy. Following irradiation, the samples were ground and demineralised for 48 hours in 10% formic acid. The osteoinductive activity was measured for each sample using a conventional in vitro osteoinductive bioassay. The demineralised bone powder was added to plates containing cell cultures. At 5 and 15 days these cells were examined for the appearance of newly formed bone. The results are summarized in the following table

| Total Dose, kGy | Dose Rate, kGy/hr | Osteoinductive Activity |
|---|---|---|
| 30 | 0.2 | Good |
| 40 | 0.2 | Good |
| 50 | 0.2 | Poor |
| 30 | 0.6 | Poor |
| 40 | 0.6 | Poor |
| 50 | 0.6 | Poor |

Example 16

Samples containing 400 mg of demineralised human allograft tissue and 0.04 ml porcine parvovirus were gamma irradiated to a total dose of 0, 30, 40 or 50 kGy. The dose response for viral inactivation of the porcine parvovirus was determined. The results are summarized in the following table:

| Sample No. | Total Dose, kGy | Remaining Titer $\log_{10}$ |
|---|---|---|
| 1 | 0 | 5.03 |
| 2 | 30 | <1.65 |
| 3 | 40 | <1.65 |
| 4 | 50 | <1.65 |

Example 17

In this experiment, type I collagen at −20° C., −80° C. or freeze-dried at 4° C. were irradiated with gamma radiation to a total dose of 45 kGy in the presence of various stabilizers.

Materials:

The following stock solutions were prepared:

1M thiourea (Sigma T8656) in water;

0.5M coumarin (Sigma CC4261) in ethanol;

0.5M 0-coumaric acid (Sigma C4400) in ethanol;

0.5M curcumin (Sigma C1386) in ethanol;

1M L-cysteine (Sigma C6852) in water;

1M 1,3-dimethyl-2-thiourea (Aldrich 534-13-4) in water;

1M 2-mercaptoethylamine (Sigma M6500) in water; and 1M 1,3-dimethylurea (Sigma D6254) in water.

Phosphate buffer solution of 40 mM sodium phosphate and 100 mM NaCl; pH=7.66.

Methods:

The following samples were prepared to a final volume of 0.5 ml:

1 mg/ml collagen in 5 mM acetic acid (control);

1 mg/ml collagen+0.1 M coumaric acid;

1 mg/ml collagen+5 mM curcumin;

1 mg/ml collagen+0.1M L-cysteine;

1 mg/ml collagen+0.1M 1,3-dimethyl-2-thiourea;

1 mg/ml collagen+0.1M thiourea;

1 mg/ml collagen+0.1M 2-mercaptoethylamine; and 1 mg/ml collagen+0.1M 1,3-dimethylurea.

The samples were irradiated as follows:

freeze-dried; temperature:4.7° C.; dose rate: 1.656 kGy/hr; total dose:45 kGy;

temperature:−20.5° C.; dose rate:1.537 kGy/hr; total does:45 kGy; and temperature:72° C.; dose rate:1.530–1.528 kGy/hr;45 kGy.

Following irradiation, the samples were analyzed by SDS-PAGE. Additionally, the samples were diluted 1:2 with water to give collagen concentrations of 0.5 mg/ml and a turbidity assay was performed to detect collagen fibril formation. Collagen fibril formation was initiated by adding 100 µl of phosphate buffer solution. The assay was done in triplicate using a microtiter plate reader at 340 nm wavelength.

Results:

Thiourea and 1,3-dimethyl-2-thiourea protected collagen from gamma irradiation at −20° C., with recoveries of 83 and 86%, respectively. Thiourea and 1,3-dimethyl-2-thiourea also protected the high molecular weight protein bands (possibly gamma chain of collagen). The protective effect of curcumin, cysteine, 2-mercaptoethylamine and 1,2-dimethylurea was less than that observed with thiourea and 1,3-dimethyl-2-thiourea. For the freeze-dried samples irradiated at 4° C., the recoveries for thiourea and 1,3-dimethyl-2-thiourea were 69 and 83%, respectively. Regarding the samples irradiated at −80° C., the recoveries for curcumin, 1,3-dimethyl-2-thiourea and thiourea were 83, 91 and 85%, respectively.

The turbidity assays showed that samples treated with thiourea and 1,3-dimethyl-2-thiourea could form fibrils after irradiation. Additionally, for the samples irradiated at −80° C., 1,2-dimethylthiourea, thiourea, cysteine and 2-mercaptoethylamine could form fibrils after irradiation.

Example 18

In this experiment, the effects of gamma irradiation on liquid and gel collagen samples containing various stabilizers were investigated.

Methods:

The following stock solutions were prepared:

(1) 2M sodium ascorbate (Spectrum S1349 QP 0839) in water;

(2) 0.25M L-methionine (Sigma M6039 88H11341) in water;

(3) 1M Gly-Gly (Sigma G3915 127H54052) in water;

(4) 1M thiourea (Sigma T8656 11k01781) in water; and (5) Phosphate buffer solution of 40 mM sodium phosphate and 100 mM NaCl; pH=7.66.

The following samples were prepared in duplicate containing either gel or liquid collagen to a final volume of 1 ml by adding 0.5 ml of phosphate buffer solution with 0.5 ml of collagen (1 mg/ml) in the presence of the stabilizer(s) indicated:

(1) Collagen (0.5 mg/ml)+no stabilizer (control);
(2) Collagen (0.5 mg/ml)+50 mM ascorbate;
(3) Collagen (0.5 mg.ml)+50 mM ascorbate+50 mM Gly-Gly;
(4) Collagen (0.5 mg/ml)+25 mM thiourea; and
(5) Collagen (0.5 mg/ml)+25 mM methionine.

or gel samples, after mixing with the phosphate buffer solution the samples were incubated at room temperature for about 30 minutes. The liquid collagen samples were maintained at 4° C. to prevent them from gelling.

The samples were gamma irradiated at about 72° C. (frozen on dry ice) at dose rates of about 1.29–1.41 kGy to a total dose of 48.73 to 53.38 kGy. The irradiated samples were analyzed by SDS-PAGE. Additionally, the samples were diluted 1:2 with water to give collagen concentrations of 0.5 mg/ml and a turbidity assay was performed to detect collagen fibril formation. Collagen fibril formation was initiated by adding 100 µl of phosphate buffer solution. The assay was done in triplicate using a microtiter plate reader at 340 nm wavelength.

Results:

From SDS-PAGE data, the sample containing the ascorbate/Gly-Gly stabilizer mixture showed the best protective effect for collagen. This stabilizer mixture protected gel collagen more effectively than liquid collagen, with recoveries of 86 and 75%, respectively. Generally, the stabilizers protected gel collagen more effectively than liquid collagen. This may be due the stabilizers being trapped in the gel matrix, thereby being more available to minimize the effects of irradiation.

The turbidity assay results were consistent with the SDS-PAGE analysis. Ascorbate and the ascorbate/Gly-Gly mixture were most effective at protecting gel collagen or liquid collagen.

Example 19

In this experiment, the effects of gamma irradiation on samples containing collagen and various stabilizers were investigated.

Methods:

The following stock solutions were prepared:
(1) 2M sodium ascorbate in water;
(2) 1M Gly-Gly in water;
(3) 2 mM Trolox C in Dulbecco's Phosphate Buffered Saline (DPBS)
(4) 0.5M lipoic acid; and
(5) 1M thiouroea in water.
(6) Phosphate buffer solution of 40 mM sodium phosphate and 100 mM NaCl; pH=7.66.

Samples were prepared in duplicate to a final volume of 0.5 ml containing the stabilizer(s) indicated:
(1) Collagen (1 mg/ml) in 5 mM acetic acid (control);
(2) Collagen (1 mg/ml)+200 mM sodium ascorbate;
(3) Collagen (1 mg/ml)+200 mM sodium ascorbate+200 mM Gly-Gly;
(4) Collagen (1 mg/ml)+200 mM sodium ascorbate+200 mM lipoic acid;
(5) Collagen (1 mg/ml)+0.1M thiourea; and
(6) Collagen (1 mg/ml)+200 µM Trolox C The samples were irradiated as follows:
(1) Liquid; temperature: 3.7° C.; dose rate: 1.67 kGy/hr; total dose: 30 kGy;
(2) Liquid; temperature: −20.3° C.; dose rate:1.552 kGy/hr; total dose: 30 kGy;
(3) Liquid; temperature: −72.5° C.; dose rate: 5.136 kGy/hr; total dose: 30 kGy;
(4) Liquid; temperature: 3.7 to 5.4° C.; dose rate: 1.67 kGy/hr; total dose: 45 kGy;
(5) Liquid; temperature: −18.6 to −20.3° C.; dose rate 1.552 kGy/hr; total dose: 45 kGy;
(6) Liquid; temperature: −72.5 to −78° C.; dose rate: 5.136 kGy/hr; total dose: 45 kGy;
(7) Freeze dried; temperature: 3.7° C.; dose rate: 1.67 kGy/hr; total dose: 30 kGy; and
(8) Freeze dried; temperature 3.3° C.; dose rate: 1.673 kGy/hr; total dose: 45 kGy.

The samples were analyzed by SDS-PAGE.

Results:

From SDS-PAGE analysis, the samples containing thiourea irradiated to 30 kGy and 45 kGy at about −20° C. had recoveries of 89 and 86%, respectively. Thiourea also protected the high molecular weight protein bands (possibly gamma chain of collagen). The samples irradiated to 30 kGy and 45 kGy at about −20° C. and containing the ascorbate/Gly-Gly stabilizer mixture had recoveries of 81 and 74%, respectively.

Regarding the samples irradiated at about −80° C., those irradiated to a total dose of about 30 kGy and containing thiourea, ascorbate, ascorbate/Gly-Gly, and ascorbate/lipoic acid, showed recoveries of 84, 77, 88 and 86%, respectively. The samples irradiated to a total dose of about 45 kGy had recoveries of 78, 81, 89 and 84%, respectively. The high molecular weight protein bands were also protected by these stabilizers.

Regarding the samples irradiated at about 4° C., for the liquid samples, thiourea appeared to afford the most effective protection. With respect to the freeze dried samples, the samples irradiated to a total dose of about 30 kGy and containing ascorbate, ascorbate/Gly-Gly and ascorbate/lipoic acid had recoveries of 99, 85 and 88% respectively. The samples irradiated to a total dose of about 45 kGy and containing ascorbate, ascorbate/Gly-Gly and ascorbate/lipoic acid had recoveries of 83, 81 and 85% respectively.

Example 20

In this experiment, the effects of gamma irradiation on *Clostridium sordellii* in bovine bone was investigated.

Methods:

Freeze-dried vials of *Clostridium sordellii* purchased from ATCC were placed in a bovine bone that contained four holes with a diameter slightly greater than the circumference of the vials that extended to the midpoint of the bone. The bone containing the vials was then irradiated at 1.5 kGy/hr with 0, 25 or 50 kGy of gamma radiation at either 4° C. or on dry ice. The contents of the vials were then resuspended in 10 mL of Reinforced Clostridial Medium supplemented with Oxyrase to provide an anaerobic environment. Serial ten-fold dilutions were made to a dilution of $10^{-9}$. Fifty microliters of each dilution was then spread on a plate containing Reinforced Clostridial Medium plus 1.5% agar. A BBL GasPak Anaerobic System was used to provide an anaerobic environment for growth of the plated bacteria. The broth cultures and the plates were incubated at 37° C. for 48 hours. Following incubation turbidity was visualized and absorbance readings were taken at 620 nm in the broth cultures and colonies were counted on the plates. Similar cultures of *Staph. epidermidis* and *E. coli* were also set up and irradiated. These cultures were prepared using media and conditions conventional for the organisms.

Results:

Unirradiated tubes of *Clostridium sordellii* showed frank growth as detected by obvious turbidity at dilutions ranging from the Stock suspension to $10^{-8}$. When exposed to 25 kGy at 4° C., all tubes were clear of growth from $10^{-1}$ to $10^{-9}$. Only the undiluted Stock suspension showed signs of growth. When the irradiation dose was increased to 50 kGy, no growth was observed in any of the tubes. Similar results were seen for the materials irradiated on dry ice. These results are shown in the following table:

| Bacteria | Description | Temperature | Log reduction 25 kGy | Log reduction 50 kGy |
|---|---|---|---|---|
| S. epidermidis | Gram Positive | 4° C. | >6.0* | >6.0* |
| E. coli | Gram Negative | 4° C. | >7.1* | >7.1* |
| C. sordellii | Spore Former | 4° C. | 6.3 | >8.0* |
| C. sordellii | Spore Former | −72° C. to −76° C. | 4.5 | >8.0* |

*: Maximum reduction detectable in the assay

Example 21

In this experiment, the effects of physical agitation on dye penetration into human bone and porcine anterior cruciate ligament (ACL) were investigated.

Method:

Materials and Equipment:

(a) 2.54 mM crystal violet (Sigma #C-6158) solution in water;

(b) Dimethyl sulfoxide (DMSO), density=1.1 g/ml (Sigma #D-1435);

(c) DMSO solution (20% w/v) made with 4.545 ml DMSO in 20.455 ml crystal violet solution;

(d) Polysorbate 80 (Tween 80, Spectrum #PO138) made at 1% (v/v) and 0.1% (v/v) with crystal violet solution;

(e) Human bone;

(f) Porcine anterior cruciate ligament;

(g) Lab Line Shaker; and (h) Branson 2510 sonicator bath.

Procedure:

One piece of human bone (approximately 1 cm in length and 0.5 mm in width and height) and ligament (approximately 0.5 cm in length) were placed in 15 ml conical tubes. The following solutions were added to the tubes, in duplicate, to give two sets of samples:

(a) 20% DMSO solution with crystal violet;

(b) 1% Tween with crystal violet solution;

(c) 0.1% Tween with crystal violet solution: and (d) crystal violet solution.

One set of samples were placed in the sonicator and sonicated for approximately 4 hours. The other set of samples were placed in the shaker for approximately 4 hours at 50° C. and 375 rpm. Following sonication or shaking, the samples were removed and stored at 4° C. overnight. The samples were then cut in half to examine the penetration of crystal violet dye into the bone and ligaments.

Results:

By visual inspection of the ligaments, the shaken samples showed better penetration than the sonicated samples. The order of penetration, from best to worst, was DMSO, crystal violet, 1% Tween and 0.1% Tween.

By visual inspection of the bones, the sonicated samples showed better penetration than the shaken samples. The sonicated samples appeared to have full penetration throughout the bone, whereas the shaken samples only had a ring of dye that did not penetrate the entire bone. For the shaken samples, the 1% Tween solution had the best penetration, the 20% DMSO and 0.1% Tween solutions had comparable penetration and the crystal violet solution had the worst penetration.

Example 22

In this experiment, the effects of irradiation on porcine anterior cruciate ligament in the presence of 10, 20 or 30% DMSO and various stablizers and stabilizer mixtures irradiated at −80° C. to a total dose of 50 kGy was investigated.

Materials:

Stock Solutions:

(a) 2M sodium ascorbate in water (Spectrum S1349);

(b) 0.5M coumaric acid (Sigma C4400, 51k3660);

(c) 0.5M n-propylgallate (Sigma P3130, 117H0526); and (d) Dimethyl sulfoxide (DMSO) (JT Baker 9224-01 H40630C).

Method:

Samples of ACL in the following solvents were prepared in duplicate (one set to be irradiated and one set not to be irradiated):

(a) 10% DMSO;

(b) 20% DMSO;

(c) 30% DMSO;

(d) 10% DMSO+200 mM sodium ascorbate+100 mM n-propylgallate+100 mM coumaric acid;

(e) 20% DMSO+200 mM sodium ascorbate+100 mM n-propylgallate+100 mM coumaric acid;

(f) 30% DMSO+200 mM sodium ascorbate+100 mM n-propylgallate+100 mM coumaric acid;

(g) 10% DMSO+100 mM thiourea;

(h) 20% DMSO+100 mM thiourea; and (i) 30% DMSO+100 mM thiourea.

The ACL's were incubated overnight with shaking at about 4° C. Following incubation, the samples were decanted and fresh solutions were added. The samples were then incubated overnight at about −80° C. and one set was irradiated to a total dose of 50 kGy at a dose rate of 1.53 kGy/hr. The other set of samples was not irradiated.

The ligaments were then washed with DPBS, cut into small samples, weighed and placed into tubes. 1.3 ml of 0.5M acetic acid was added to each tube. Pepsin was added to each tube at a 1:10 ratio of enzyme:tissue in 0.5M acetic acid and the samples were incubated overnight on a nutator at about 4° C.

Following incubation, the pepsin-digested supernatant was decanted and NaCl from a 5M stock solution was added to a final concentration of 1M. The supernatants were then centrifuged for about 30 minutes at 18,300 rpm at about 4° C. Collagen gel pellets were resuspended in 1 ml of 0.5M acetic acid with gentle mixing at 4° C. and dialyzed against 5 mM acetic acid.

These samples were analyzed by SDS-PAGE analysis and a turbidity assay.

Results:

According to SDS-PAGE analysis, the purified pepsin digested collagen from ACL irradiated at −80° C. with 10%DMSO+200 mM sodium ascorbate+100 mM n-propylgallate+100 mM coumaric acid showed the best recovery. The yields for samples treated with 10%DMSO+200 mM sodium ascorbate+100 mM n-propylgallate+100 mM coumaric acid, 20%DMSO+200 mM sodium ascorbate+100 mM n-propylgallate+100 mM coumaric acid and 30%DMSO+200 mM sodium ascorbate+100 mM n-propylgallate+100 mM coumaric acid were 90%, 88% and 80%, respectively. For thiourea, the yield for samples containing 10% DMSO+100 mM thiourea, 20% DMSO+100 mM thiourea and 30% DMSO+100 mM thiourea were 87%, 76% and 67%, respectively.

Example 23

In this experiment, the effects of various stabilizers on human femur as measured by a three point bending test were investigated.

Methods:

Blocks of human femur measuring 5 mm×5 mm×10 mm were cut using a bone saw equipped with diamond edged blade.

Femur samples were prepared as follows:

(1) Sample treatment +A: samples were soaked in 200 mM ascorbate for about 24 hours and then either not irradiated or irradiated at about 5.2° C. at a dose rate of about 1.6 kGy/hr to a total dose of either 25 kGy or 50 kGy;

(2) Sample treatment −A: samples were soaked in water for about 24 hours; and then either not irradiated or irradiated at about 5.2° C. at a dose rate of about 1.6 kGy/hr to a total dose of either 25 kGy or 50 kGy;

(3) Sample treatment +A/a.d.: samples were soaked in 200 mM ascorbate for about 24 hours, air-dried overnight and then either not irradiated or irradiated as air-dried bone at a dose rate of about 1.6 kGy/hr to a total dose of either 25 kGy (at about 4.1° C.) or 50 kGy (at about 6.1° C.);

(4) Sample treatment −A/a.d.: samples were soaked in water for about 24 hours, air-dried overnight and then either not irradiated or irradiated as air-dried bone at a dose rate of about 1.6 kGy/hr to a total dose of either 25 kGy (at about 4.1° C.) or 50 kGy (at about 6.1° C.);

(5) Sample treatment +CK2: samples were soaked in a cryoprotectant cocktail containing 100 mM trehalose, 150 mM mannitol, 24.2%DMSO, 16.8% butanediol and 14% formamide for about 24 hours, quick frozen in a dry-ice/ethanol bath and then either not irradiated or irradiated at about −72° C. at a dose rate of about 2.45 kGy/hr to a total dose of either 25 kGy or 50 kGy;

(6) Sample treatment −CK2: samples were soaked in 24.2%DMSO for about 24 hours, quick frozen in a dry-ice/ethanol bath and then either not irradiated or irradiated at about −72° C. at a dose rate of about 2.45 kGy/hr to a total dose of either 25 kGy or 50 kGy;

(7) Sample treatment +CK1: samples were soaked in polypropylene glycol (PPG) overnight, removed from PPG and wiped of excess PPG. The samples were then soaked in a stabilizer cocktail containing 100 μM trolox, 100 mM coumaric acid, 100 mM lipoic acid and 100 mM propyl gallate for about 24 hours, quick frozen in a dry-ice/ethanol bath and then either not irradiated or irradiated at about −72° C. at a dose of about 2.45 kGy/hr to a total dose of either 25 kGy or 50 kGy (samples +CK1); and (8) Sample treatment −CK1: samples were soaked in PPG overnight, removed from PPG and wiped of excess PPG. The samples were then either not irradiated or irradiated at about −72° C. at a dose of about 2.45 kGy/hr to a total dose of either 25 kGy or 50 kGy.

Following treatment as outlined above, the samples were subjected to a three point bending test. The results and test are presented in the following table:

3 Point Bending Test of Human Femur $$\sigma_b = (3PL)/(2bh^2)$$

where:

$\sigma_b$=bending stress (MPa);

P=maximum load bone (N);

L=support span (12.6 mm);

b=sample width (mm); and h=sample height (mm).

| Sample Treatment | Total Dose | Ave $\sigma_b$ | Std Dev |
|---|---|---|---|
| +A | 0 | 204.310 | 24.229 |
|  | 25 | 160.299 | 20.320 |
|  | 50 | 114.695 | 19.115 |
| −A | 0 | 180.402 | 14.706 |
|  | 25 | 138.366 | 41.132 |
|  | 50 | 125.557 | 9.180 |
| +CK2 | 0 | 217.925 | 13.033 |
|  | 25 | 207.496 | 16.058 |
|  | 50 | 186.578 | 30.182 |
| −CK2 | 0 | 194.240 | 21.253 |
|  | 25 | 176.385 | 11.249 |
|  | 50 | 144.499 | 28.051 |
| +A/a.d. | 0 | 184.969 | 43.349 |
|  | 25 | 146.857 | 14.741 |
|  | 50 | 78.102 | 24.446 |
| −A/a.d. | 0 | 182.516 | 34.202 |
|  | 25 | 139.275 | 16.984 |
|  | 50 | 88.670 | 10.876 |
| +CK1 | 0 | 190.267 | 24.822 |
|  | 25 | 172.056 | 7.042 |
|  | 50 | 132.895 | 16.209 |
| −CK1 | 0 | 190.014 | 17.244 |
|  | 25 | 148.423 | 8.087 |
|  | 50 | 110.263 | 15.832 |

Example 24

In this experiment, the effects of gamma radiation on liquid and gel collagen samples irradiated at about −20° C. at a dose rate of about 1.486 kGy/hr to a total dose of 45 kGy.

Methods:

The following stock solutions were prepared:

(1) 2M sodium ascorbate (Spectrum S1349 QP 0839) in water;

(2) 0.24M L-methionine (Sigma M6039 88H111341) in water;

(3) 1M Gly-Gly (Sigma G3915 127H54052) in water; and (4) 1M thiourea (Sigma T8656 11k01781) in water.

Samples were prepared in the final volume of 1 ml for irradiation. Samples were prepared by adding 0.5 ml of 40 mM NaCl with 0.5 ml liquid or gel collagen (1 mg/ml) in the presence of the following stabilizers:

(1) Control: collagen (0.5 mg/ml);

(2) Collagen (0.5 mg/ml)+50 mM ascorbate;

(3) Collagen (0.5 mg/ml)+50 mM ascorbate+50 mM Gly-Gly;

(4) Collagen (0.5 mg/ml)+25 mM thiourea; and (5) Collagen (0.5 mg/ml)+25 mM methionine.

The gel samples were incubated for about 30 minutes at room temperature after mixing with phosphate buffer. The liquid collagen samples were kept at about 4° C. to prevent gelling. Then, both gel and liquid collagen samples were frozen at −20° C. and irradiated at −20° C. at a dose rate of about 1.486 kGy/hr to a total dose of about 45 kGy.

The samples were analyzed by SDS-PAGE and a turbidity assay.

Results:

According to SDS-PAGE, the samples containing ascorbate+Gly-Gly showed recoveries of 77% for gel collagen and 81% for liquid collagen. The samples containing thiourea showed recoveries of 80% for gel collagen and 87% for liquid collagen.

From turbidity data, thiourea appeared to be the best stabilizer in protecting either gel or liquid collagen at −20° C.

Example 25

In this experiment, the protective effects of various stabilizers on porcine anterior cruciate ligament (ACL) irradiated at about −72° C. to a total dose of about 50 kGy were investigated.

Methods:

The following stock solutions were prepared:

(1) 400 mM propyl gallate (Sigma P-3130, lot 60K0877) and 400 mM butylated hydroxyanisole (BHA) (Sigma B-1253, lot 19H0261) in 100% DMSO;

(2) 400 mM N-t-butyl-α-phenyl nitrone (BPN) (Sigma B-7263, lot 60K1191) in 50% DMSO;

(3) 100 mM curcumin (Sigma C-1386, lot 100K3447) in 50% DMSO;

(4) 200 mM probucol (Sigma P-9672, lot 128H0695) in 50% PPG and 50% tocopherol; and (5) 400 mM Trp-Ala (Sigma T-8152, lot 129F58502) in 100% DMSO.

Following dehydration with PPG, the ligaments were blotted to remove excess PPG and placed in 2 ml serum vials. Stabilizers were added to the following final concentrations in duplicate (one set will receive 0 kGy irradiation and the other will receive 50 kGy):

(1) 200 mM proply gallate and 200 mM BHA in 50% DMSO;

(2) 200 mM BPN in 25% DMSO;

(3) 100 mM curcumin in 50% DMSO;

(4) 200 mM probucol in 50:50 PPG:Tocopherol;

(5) 200 mM Trp-Ala in 50% DMSO; and (6) Control, 50% DMSO.

The vials were then nutated at about 4° C. for about 136 hours. Following nutation, the samples were quick frozen in a dry-ice/ethanol bath and stored at about −80° C. One set of samples were then irradiated at about −72° C. at a dose rate of about 1.35 kGy/hr to a total dose of about 50 kGy and the other set was not irradiated.

Following irradiation, the samples were treated as follows:

(1) the samples were washed 5 times with PBS to remove the stabilizers and stored in PBS at about 4° C.;

(2) a small piece from the center of the ligament was cut, pressed to remove excess PBS and quick frozen on a dry-ice/ethanol bath;

(3) the frozen ligaments were then minced with a razor blade and weighed;

(4) 20× (w/v) of 0.5N acetic acid and pepsin at 1:10 (w/w substrate to enzyme) were added to the samples and the samples were digested for about 24 hours at about 4° C. with vigorous shaking;

(5) another volume of pepsin was added to the samples and the samples were digested for about 24 hours at about 4° C. with vigorous shaking;

(6) 200 µl of 0.5N acetic acid were added to the samples;

(7) the samples were centrifuged for about 1 hour at 4° C. and 20,000 rpm;

(8) following centrifugation, the supernatant was removed and the collagen was precipitated by adding NaCl to 2M;

(9) the samples were then vigorously shaken for 3 hours at 4° C., placed on an ice bath for 3 hours without shaking and centrifuged at 20,000 rpm for 1 hour at 4° C.; and

(10) the pellets were solubilized with 0.5N acetic acid overnight on a nutator at 4° C.

Results:

Irradiating at low temperature in the presence of stabilizers results in improved recovery compared to samples not containing stabilizers. Particularly good recovery was observed with the samples containing probucol in 50:50 PPG:tocopherol irradiated to about 50 kGy.

Experiment 26

In this experiment, the effects of "fast freezing" as compared to "slow freezing" on porcine heart valves in the presence or absence of various cryopreservatives irradiated at a dose rate of about 5.109 kGy/hr to a total dose of 50 kGy at about −72° C. were investigated.

Methods:

The following stock solutions were prepared:

(1) 1M trehalose (Sigma T-9531, lot 61K7026);

(2) 1M $KH_2PO_4$ (Sigma P-5655, lot 41H07875);

(3) 1M $K_2HPO_4$ (Sigma P-2222, lot 80K1035);

(4) 1M KCl (Sigma P-5405, lot 52H6876);

(5) 1M mannitol (Sigma M-849, lot 106H00842);

(6) 1M $NaHCO_3$ (Sigma 5761); and (7) 2M sodium ascorbate (Spectrum S 1349, lot QP0839).

Additionally, the following reagents were employed:

(1) ethanol (Spectrum S1349, lot QP0839);

(2) DMSO (J. T. Baker, 9224-01, lot K50664);

(3) 1,2-propanediol (Aldrich 39,803-9, lot 09521HO);

(4) formamide (EM Science, 4650, lot 3631B33); and (5) PBS.

A cryopreservative mixture to the following final concentrations was prepared:

| | |
|---|---|
| Trehalose | 100 mM |
| $KH_2PO_4$ | 15 mM |
| $K_2HPO_4$ | 42 mM |
| KCl | 15 mM |
| $NaHCO_3$ | 10 mM |
| mannitol | 150 mM |
| DMSO | 24.2% |
| 1,2-propanediol | 16.8% |
| formamide | 14.0% |

Frozen porcine heart valves were thawed on ice and the 3 cusps from were dissected. The cusps were rinsed in PBS and transferred to 2 ml irradiation vials. 900 µl of the cryopreservative mixture were added to the samples. 100 µl of $H_2O$ were added to half of the samples (designated −Asc samples) and 100 µl sodium ascorbate was added to the other half of the samples.

Samples were either slow frozen or fast frozen, as follows:

(1) Slow freezing: the vials were placed without stoppers into a freeze dryer and frozen to about −65° C. at a rate of approximately −1° C./min; and (2) Fast freezing: the vials were quick frozen in less than about 5 minutes in a dry-ice/ethanol bath.

Following freezing, half of the samples were irradiated at about −72° C. at a dose rate of about 5.1 kGy/hr to a total dose of 50 kGy.

Following irradiation, the samples were analyzed by SDS-PAGE analysis, western blotting with anti-decorin and anti-fibronectin, and uronic acid determination.

Results:

According to SDS-PAGE analysis, the irradiated samples had an increase in the intensity of the lowest molecular weight band of the triplet observed at about 130 kDa. There appeared not to be significant differences between samples that were slow frozen and those that were fast frozen. Additionally, the irradiated samples showed good recovery of the pentuplet band at about 205 kDa.

Western blotting with anti-decorin showed weaker staining of the band at about 116 kDa for the irradiated samples as compared to the unirradiated samples. The antifibronectin antibody showed weaker reactivity with three or four of the bands at about 220 kDa in the irradiated samples as compared to the unirradiated samples.

All irradiated samples had less total uric acid than their unirradiated controls (43–74%). The fast frozen samples irradiated in the presence of the stabilizer mixture and ascorbate showed recovery of about 74%.

Example 27

In this experiment, the effects of various cryopreservatives on porcine heart valves irradiated to about 50 kGy at about −80° C. in the presence or absence of sodium ascorbate were investigated.

Methods:

Dissected porcine heart valve cusp samples were divided into two groups. The groups were treated with one of the following solutions:

(1) Solution CP1 containing 10% FCS, Penicillin-streptomycin, M199 and 2M DMSO; and (2) Solution CP2 containing 100 mM trehalose, 15 mM KH2PO4, 42 mM K2HPO4, 15 mM KCl, 10 mM NaHCO3, 150 mM mannitol, 24.2% DMSO, 16.8% 1,2-propanediol, and 14% formamide.

In addition, 200 mM sodium ascorbate (Asc) was added to half of the samples containing solution CP1 and half of the samples containing solution CP2 to give the following four sets of samples: CP1+Asc, CP1−Asc, CP2+Asc and CP2−Asc. For each of these sets, half of the samples were fast frozen and half were slow frozen, in duplicate. (See Example 26). One set of these samples was irradiated to 50 kGy at about −80° C. and the other set was not irradiated.

Following irradiation, the heart valve cusps were minced into small pieces and resuspended in 1 ml of 0.5N acetic acid. Pepsin was added to these pellets at a 1:10 ratio of enzyme:tissue in 0.5N acetic acid. The samples were incubated at about 4° C. on the nutator for 2 days. Following incubation, another portion of pepsin was added to each sample and the samples were incubated on the nutator overnight at about 4° C.

The pepsin digests were then centrifuged at 22,000 rpm at 4° C. for 30 minutes. Following centrifugation, 5M NaCl was added to the supernatants to a final concentration of 1M. The supernatants were then cenrifuged at 22,000 rpm for 30 min at 4° C. The collagen pellets were then resuspended in 1 ml of 0.5N acetic acid with gentle mixing at 4° C. 10 μg of the pepsin digested collagen from each sample were run on 4–12% gel.

The pepsin digested collagens were dialyzed against 5 mM acetic acid. and absorption was measured at 218 nm.

Results:

From the SDS-PAGE, purified pepsin digested collagen treated from samples treated with solution CP2 showed better recovery than samples treated with solution CP1. For these samples, the yield for collagen α-chain was 93.7% for the slow freeze samples and >100% for the fast freeze samples. The inclusion of ascorbate appeared to increase the recovery somewhat for all samples.

Example 28

In this experiment, the effects of "fast freezing" as compared to "slow freezing" on porcine heart valves in the presence or absence of various cryopreservative with or without sodium ascorbate irradiated at a dose rate of about 5.13 kGy/hr to a total dose of 50 kGy at about −72° C. were investigated.

Methods:

The following stock solutions were prepared:

(1) Freeze medium (M199/FCS/P-S):

fetal calf serum (FCS) (10%)=50 ml penicillin-strepotomycin (P-S)=2.5 ml

M199=QS 500 ml;

(2) 2M DMSO solution:

DMSO=15.62 g

Freeze medium=QS 100 ml. and (3) 3M DSMO solution:

DMSO=23.44 g

Freeze medium=QS 100 ml

Frozen procine heart valves were thawed on ice. The three heart cusps were then dissected out and placed in 2 ml irradiation vials. Half of the samples were treated with the 2M DMSO solution and the other half were treated with the 3M DSMO solution. For each set of samples, 100 μl of H$_2$O were added to half of the samples and 100 μl of 2M sodium ascorbate were added to the other half. Half of the samples were fast frozen and half were slow frozen. (See Example 26).

The samples were then irradiatated at about −72° C. at a dose rate of about 5.14 kGy/hr to a total dose of 50 kGy. Control samples were not irradiated.

Following irradiation, the samples were washed several times with approximately 30 ml of cold PBS and incubated on ice for about 30–45 minutes. The samples were washed and incubated a total of 5 times. After the final wash, 2 cusps from each sample were transferred into eppendorfs containing 1 ml cold PBS and the third cusp was transferred to a separate eppendorf reserved for histological analysis also containing 1 ml cold PBS.

Each cusp was then washed 6 times with acetone in the eppendorf (approximately 1.5 ml per wash) and subjected to vacuum drying, with no heat, for about 15 minutes, or until dry. The samples were then weigh and hydrolized at a ratio of 10 mg tissue to 1 ml 6N HCl. Following hydrolysis, the samples were centrifuged at 4,000 rpm for about 10 minutes. The supernatants were transferred into clean eppendorfs.

The samples were analyzed by SDS-PAGE.

Results:

SDS-PAGE analysis showed that there was no clear difference between cusps that were fast frozen and those that were slow frozen in either the 2M DMSO solution or the 3M DMSO solution. The presence or absence of ascorbate appeared not to impact recovery.

Example 29

In this experiment, the dose distribution and temperature profile for a volume of bovine paste gamma irradiated in an insulated container were evaluated.

Equipment and Materials

32 Omega Type T thermocouples (Stock # 5SC-TT-T-36-72)
36-gauge wire
72" length

Omega TC readers—Model HH202A, Ser. Nos. 20910 (Reader 1) & 20909 (Reader 2)

Envirocooler insulated container EVC-30-40-LL
Outer dimensions—24"×23.75" 23.75" (H×W×L)
Inner dimensions—17.5"×17.75"×17.75" (H×W×L)

Cardboard paste container—14"×10.25"×10.5" (H×W×L)

Dry ice (pellets)
Bovine Fraction "A" paste—filter press paste (50–60% IgG), diatomaceous earth and Perlite Dosimeters—Alanine pellets (Gamma Service, Batch T79801); Red 4034 Perspex GH 44 Microfuge tubes (plastic, 0.6 ml)

Cardboard slip sheets

Paper Thermometer Co. Set #10 thermal labels (range: 32.2–54.4° C.)

STERIS batch-type irradiator (IR-131), Whippany, N.J.

Procedure

Part A

1. Checked the functionality of thirty-two (32) Type T thermocouples (TCs) using two readout instruments.
   a. Uniquely identified each TC.
   b. Performed a 3-point verification at nominal temperatures of 22, 0 and −78° C. using baths appropriate to achieve these nominal temperatures. Where available, used a thermometer to independently determine bath temperature.
   c. Only those TCs that performed accurately (to within 2° C. of reference temperature) and reliably were used.
   d. Added labels at the ends of each TC with the corresponding identifier.

2. Prepared a cardboard carton to contain the bovine paste.
   a. The carton was sturdy/rigid and lined appropriately to withstand the rigors of adding the heavy, moist paste. This carton was placed within the insulated Envirocooler container.
   b. Documented the dimensions of the fabricated carton.

3. Prepared forty-four (44) dosimeters—each dosimeter consists of three (3) alanine dosimeters in a 0.6 ml microfuge tube (vial). Each vial was uniquely labeled.

4. Positioned the dosimeters and TCs to individual cardboard slip sheets (3) as illustrated in FIG. 1, and recorded the TC and dosimeter numbers corresponding to the positions.

5. Labeled both the Envirocooler container and paste carton to identify FRONT, REAR and TOP.

Part B

1. Placed the first slip sheet (Layer 1) in the bottom of the paste carton, noting the corresponding TC and dosimeter positions within the past carton.

2. Unwrapped the TC wire so the leads exited the paste carton. The TCs for each corresponding layer were ultimately bundled together.

3. Added bovine paste (previously prepared) to approximately the mid-height of the paste carton.

4. Placed the second slip sheet (Layer 2) at mid-height of the carton, noting the corresponding TC and dosimeter positions. Recorded the height of Layer 2 relative to Layer 1.

5. Unwrapped the TC wire so the leads exited the paste carton.

6. Added more paste to fill the carton.

7. Added the third slip sheet (Layer 3), noting the corresponding TC and dosimeter positions. Recorded the height of Layer 3 relative to Layers 1 and 2.

8. Sealed the carton.

9. Secured the TCs, creating bundles (as described above) for ease of manipulation and subsequent temperature measurements.

10. Froze the paste in a nominal −40° C. freezer.

Figure 2:
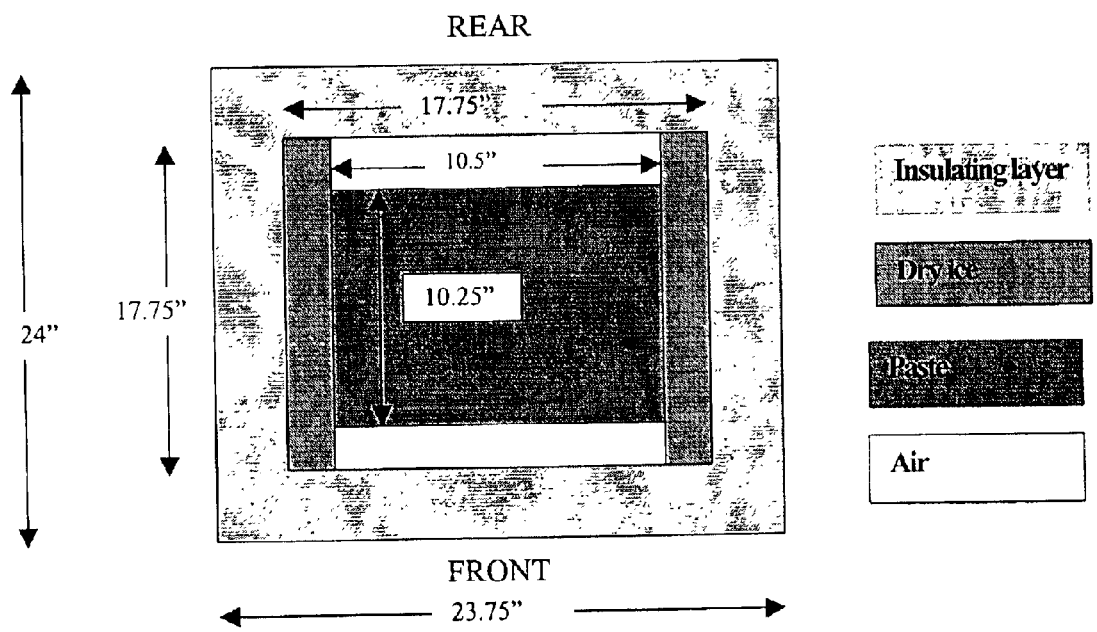
FIG. 2 illustrates a top view of the insulated container and contents of Example 29 of the present invention.

11. Once the paste was frozen:
    a. Measured and recorded the paste carton dimensions,
    b. Weighed the paste carton and recorded the resulting weight.
    c. Placed the paste carton in the Envirocooler insulated container oriented per FIG. 2.

12. Extended the TC leads (bundled) to the exterior of the Envirocooler container and secured to the exterior surface of the container.

13. Added cardboard 'sleeves' to the sides of the paste container that extended from front to back of the insulating layer. Note: These sleeves were used to secure the dry ice and keep it from falling into the void space in front of (and behind) the paste.

14. Inserted low density material (styrofoam peanuts) into the void space between the paste carton and insulating layer to stabilize, and maintained the position of the paste carton within the Envirocooler container.

15. Weighed the container and recorded the weight, date and time.

16. Added dry ice (approximately 3") between the cardboard sleeves and the insulating layer of the Envirocooler container, and sealed the container.

17. Weighed the (sealed) Envirocooler container and recorded the weight.

Part C

1. Weighed the Envirocooler container and recorded the weight, date and time of measurement.

2. Measured the temperature for each TC and documented the results along with date/time of measurement.

3. Coordinated with the irradiation facility regarding date/time irradiation is expected to begin.

4. Once the irradiation was scheduled and the container was being prepared for transport to the irradiation site:
   a. Opened the Envirocooler container and examined the status of the dry ice.
   b. Added dry ice (as necessary) to maintain the configuration in FIG. 2.
   c. Sealed the container for transport.

5. Collected all additional dosimeters, TCs and readers, thermal strips, etc. required.

Part D

1. Upon arrival at the irradiation facility, weighed the container and documented the weight, time and date.

Figure 3A:
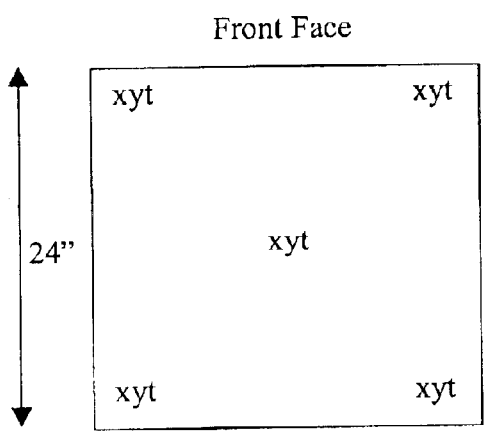
FIGS. 3A–3C illustrate the external placement of dosimeters of Example 29 of the present invention.
Figure 3B:
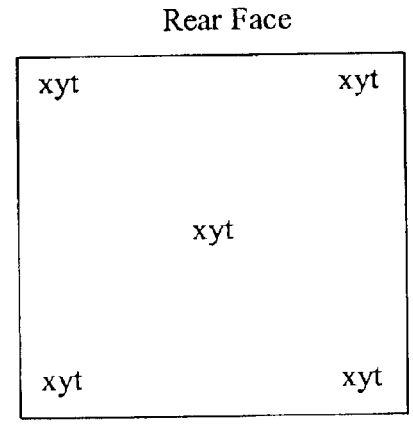
Figure 3C:
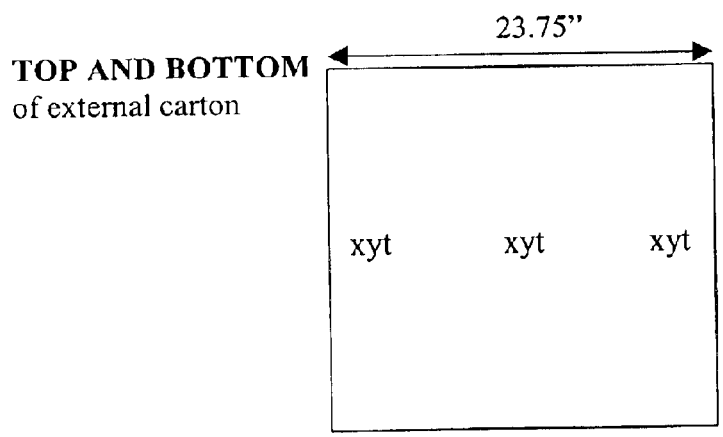

2. Added the external and irradiation facility dosimeters as well as the thermal strips to the container at the positions illustrated in FIG. 3(a, b and c).

3. Just prior to the start of irradiation, measured the temperature of each TC and recorded the result, time and date.

4. Loaded the irradiation carrier with 32" of cardboard.

5. Placed the container in the carrier on top of the cardboard such that the FRONT and REAR faces of the container (and paste carton) were parallel to the source plaque. Centered the container within the carrier.

6. Irradiated the container to achieve a surface dose of 50 kGy (dose in water) or 48.5 kGy (dose in PMMA).
7. Once the carrier was loaded into the irradiation cell ready to be irradiated, used a TC and reader to record the ambient temperature. Noted the date and time of measurement.
8. Following irradiation, recorded the temperature for each TC, time and date.
9. After the final irradiation event:
    a. Removed the container from the carrier.
    b. Removed external dosimeters for analysis.
    c. Weighed the container and recorded the date/time of measurement.
    d. Recorded the resulting thermal label results and corresponding positions.

Results

Weight summary (and dry ice accountability)

| Item | Weight (lbs.) |
| --- | --- |
| Envirocooler container (empty) | 17.2 |
| Paste carton (filled, with TCs) | 42.2 |
| Dry ice | |
| Start (Mar. 26, 2002, 5 PM) | 63.6 |
| End (Mar. 28, 2002, 10 AM) | 40.0 |
| Net loss (41 hours elapsed) | 23.6 |
| Total weight (packed container) | 123 |

Verification of Thermocouple Performance

The functionality of each Type T thermocouple (TC) was demonstrated both prior to use (Mar. 21, 2002) and following irradiation (Apr. 8, 2002).

Pre-irradiation performance

Omega Reader #1 consistently read higher than Omega Reader #2, with differences up to 1.5° C. Omega Reader #1 was used for subsequent temperature measurements.

Most TCs demonstrated agreement to within 2° C. at the 3 nominal temperature test points (20, 0 and −78° C.) using both readers. However, TC #11 (previously irradiated) demonstrated a larger difference (3.5° C.) at the dry ice temperature test point for Reader #1.

Post-irradiation performance

Only Reader #1 was used to check thermocouples.

Most TCs demonstrated agreement to within 1° C. at nominal temperature test points of +20 and 0° C.). At the dry ice test point, most TCs demonstrated agreement to within 2° C. with selected TCs—not previously irradiated—having differences of 3.5° C.

Thermal Label Data

Maximum recorded temperatures ranged from 38 to 54° C. (approximately a 15 to 30° C. rise above ambient) for all labels.

FRONT face labels ranged from 49 to 54° C. while REAR face labels ranged from 38 to 43° C.

TOP and BOTTOM labels all read 38° C.

Temperatures were observed to have reached the maximum reported values during the first dose fraction.

Thermocouple Data

In general, temperatures within the paste rose 15° C. or less. However, the maximum observed temperature rise during irradiation was approximately 19° C. (MIDSECTION Bottom Center).

The Bottom Center position resulted in the highest temperature for all 3 faces.

Temperature continued to increase during the time that measurements were being taken following irradiation (for both the $1^{st}$ and $2^{nd}$ fractions). Temperatures increased as much as 3° C. between readings taken 10 minutes apart.

Internal Alanine Dosimetry Data

The minimum dose in the paste, 37.4 kGy, occurred at the geometric center.

The maximum dose in the paste, 55.4 kGy, occurred at the REAR Top Center position.

The maximum/minimum dose ratio for the paste was 1.48 (REAR Top Center and REAR Top Right locations).

The maximum/minimum dose ratio for the FRONT, MID-SECTION and REAR faces was 1.15, 1.30 and 1.16, respectively.

The dose 'drop off' from the FRONT or REAR Center position to the MIDSECTION Center position (5.25") was approximately 30%.

Lateral dose distribution within each face (FRONT, MID-SECTION and REAR) was relatively uniform with greatest difference being 8% at the MIDSECTION (Layer 2).

External Alanine and Red 4034 Dosimetry

Alanine doses were consistently higher than their corresponding Red 4034 dose values. There was good correlation (to within 2 kGy) between the alanine and Red 4034 dose results for 11 locations—TOP(3), BOTTOM (3) and E1 through E5(5). However, alanine doses at positions A1–A5 were approximately 3.5 to 8.5 kGy higher than the Red 4034 dosimeters.

The corresponding Front and Rear surface dosimetry demonstrated relatively similar dosing for the alanine. However, the same was not true for Red 4034 dose values—differences in corresponding positions ranged from approximately 3 to 6 kGy which were directly related to the first dose fraction delivered.

Dose Distribution

The dose distribution within the paste (max/min) was 1.48. The 'drop off' from FRONT/REAR face to MID-SECTION face (ratio) was 1.30.

Higher doses were observed on the top layer of the paste. This was likely due to less shielding above the container (4" cardboard) than below the container (32" cardboard).

FRONT and REAR faces internally and externally showed comparable dosing (based on the alanine results), illustrating uniformity in surface dose delivery for on-carrier (double-sided) irradiation.

Temperature Control

The Envirocooler insulated container (3") and dry ice arrangement provided temperature control throughout all stages of preparation, irradiation, and post-irradiation handling.

Over a 41-hour period 23 lbs of dry ice was lost.

Temperature rise in the paste was approximately 15° C. rise with delivery of 50 kGy surface dose in two unequal fractions.

Thermocouple Performance

Calibration results indicated consistent difference in the readings for the 2 Omega readers, with Reader 1 reading higher than Reader 2.

TCs #1 through #14 had been previously exposed in other irradiation experiments, and generally performed comparably to other TCs that had not been previously irradiated.

Having now fully described this invention, it will be understood to those of ordinary skill in the art that the methods of the present invention can be carried out with a wide and equivalent range of conditions, formulations and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A method for sterilizing a biological material that is sensitive to radiation, said method comprising: (a) determining the maximum acceptable temperature ($T_{max}$) for said biological material during irradiation; and (b) irradiating said biological material with radiation for a time effective to sterilize said biological material at a rate effective to sterilize said biological material, wherein said irradiating is performed under conditions whereby the temperature of said biological material increases during said irradiating from an initial temperature ($T_i$) to a final temperature ($T_f$), wherein said initial temperature ($T_i$) is no greater than about $T_{max}-T$, wherein T is about equal to the total dose of said radiation (D) divided by the specific heat capacity (c) of said biological material.

2. A method for sterilizing a biological material that is sensitive to radiation, said method comprising; (a) determining the maximum acceptable temperature ($T_{max}$) for said biological material during irradiation; and (b) irradiating said biological material with radiation for a time effective to sterilize said biological material at a rate effective to sterilize said biological material, wherein said irradiating is performed under conditions whereby the temperature of said biological material increases during said irradiating from an initial temperature ($T_i$) to a final temperature ($T_f$), wherein said initial temperature ($T_i$) is no greater than about $T_{max}-T_{obs}$, wherein $T_{obs}$ is determined by a process comprising irradiating a sample of said biological material or a suitable substitute therefore with said radiation under the conditions under which said biological material is to be irradiated in step (b) while measuring the increase in temperature of said sample.

3. The method according to claim 1 or 2, wherein said final temperature ($T_f$) is at or below a temperature effective to protect said biological material from said radiation.

4. The method according to claim 1 or 2, wherein at least one stabilizing process is applied to said biological material prior to said irradiating, said stabilizing process being selected from the group consisting of: (a) adding to said biological material at least one stabilizer; (b) reducing the residual solvent content of said biological material; (c) reducing the oxygen content of said biological material; (d) adjusting the pH of said biological material; and (e) adding to said biological material at least one non-aqueous solvent, wherein said stabilizing process is effective to protect said biological material from said radiation.

5. The method according to claim 1 or 2, wherein said increase in the temperature of the biological material is about 0.25° C./kGy.

6. The method according to claim 1 or 2, wherein said increase in the temperature of the biological material is about 1.2° C./kGy.

7. The method according to claim 1 or 2, wherein said rate is effective to protect said biological material from said radiation.

8. The method according to claim 4, wherein at least two stabilizing processes are applied to said biological material prior to said irradiating.

9. The method according to claim 1 or 2, wherein said rate is at least about 3.0 kGy/hr.

10. The method according to claim 1 or 2, wherein said rate is at least about 30.0 kGy/hr.

11. The method according to claim 1 or 2, wherein said rate is at least about 45.0 kGy/hr.

12. The method according to claim 1 or 2, wherein said biological material is maintained in a low oxygen atmosphere.

13. The method according to claim 1 or 2, wherein said biological material is maintained in an atmosphere comprising at least one noble gas or nitrogen.

14. The method according to claim 13, wherein said noble gas is argon.

15. The method according to claim 1 or 2, wherein said biological material is maintained in a vacuum.

16. The method according to claim 1 or 2, wherein at least one sensitizer is added to said biological material prior to said step of irradiating said biological material.

17. The method according to claim 1 or 2, wherein said radiation is selected from the group consisting of gamma, corpuscular, electromagnetic and combinations thereof.

18. The method according to claim 17, wherein said electromagnetic radiation is selected from the group consisting of radio waves, microwaves, visible and invisible light, ultraviolet light, x-ray radiation, gamma radiation and combinations thereof.

19. The method according to claim 1 or 2, wherein said irradiation is conducted at a temperature below ambient temperature.

20. The method according to claim 1 or 2, wherein said radiation is conducted at a temperature below the freezing point of said biological material.

21. The method according to claim 1 or 2, wherein said biological material is selected from the group consisting of dextrose, urokinase, thrombin, purified protein fraction, blood, blood cells, alpha-1 proteinase inhibitor, digestive enzymes, blood proteins and tissue.

22. The method according to claim 21, wherein said tissue is selected from the group consisting of tendons, nerves, bone, teeth, bone marrow, skin grafts, cartilage, corneas, arteries, veins, heart valves, ligaments and demineralized bone matrix.

23. The method according to claim 21, wherein said digestive enzymes are selected from the group consisting of galactosidases and sulfatases.

24. The method according to claim 21, wherein said blood proteins are selected from the group consisting of albumin, Factor VIII, Factor VII, Factor IV, fibrinogen, monoclonal immunoglobulins and polyclonal immunoglobulins.

25. The method according to claim 1 or 2, wherein said biological material is milk.

26. The method according to claim 1 or 2, wherein said biological material is serum or plasma.

27. The method according to claim 4, wherein said residual solvent content is reduced by a method selected from the group consisting of lyophilization, drying, concentration, addition of solute, evaporation, chemical extraction, spray-drying and vitrification.

28. The method according to claim 4, wherein said residual solvent content is reduced to a level less than about 33%.

29. The method according to claim 4, wherein said residual solvent content is reduced to a level less than about 15%.

30. The method according to claim 4, wherein said residual solvent content is reduced to a level less than about 8%.

31. The method according to claim 4, wherein said residual solvent is an organic solvent.

32. The method according to claim 31, wherein said organic solvent is selected from the group consisting of ethanol, isopropanol, polyethylene glycol and mixtures thereof.

33. The method according to claim 4, wherein said residual solvent is an aqueous solvent.

34. The method according to claim 4, wherein said at least one stabilizer is an antioxidant.

35. The method according to claim 4, wherein said at least one stabilizer is selected from the group consisting of: ascorbic acid or a salt or ester thereof; glutathione; vitamin E or a derivative thereof; albumin; sucrose; glycyiglycine; L-carnosine; cysteine; silymarin; diosmin; hydroquinonesulfonic acid; 6-hydroxy-2,5,7,8-tetramethylchroman-2-carboxylic acid; uric acid or a salt or ester thereof; methionine; histidine; N-acetyl cysteine; lipoic acid; sodium formaldehyde sulfoxylate; gallic acid or a derivative thereof; propyl gallate; ethanol; acetone; rutin; epicatechin; biacalein; purpurogallin; mannitol; trehalose; DMSO and mixtures of two or more thereof.

36. The method according to claim 35, wherein said at least one stabilizer is selected from the group consisting of mannitol, propylene glycol, trehalose, DMSO and mixtures thereof.

37. The method according to claim 35, wherein said mixtures of two or more stabilizers comprise ascorbic acid or a salt or ester thereof and at least one stabilizer selected from the group consisting of: ethanol; acetone; 6-hydroxy-2,5,7,8-tetramethylchroman-2-carboxylic acid; 6-hydroxy-2,5,7,8-tetramethylchroman-2-carboxylic acid; albumin; sucrose; glycylglycine; L-camosine; N-acetyl cysteine; silymarin; diosmin; lipoic acid; hydroquinonesulfonic acid; sodium formaldehyde sulfoxylate; and gallic acid or a derivative thereof.

38. The method according to claim 35, wherein said mixtures of two or more stabilizers comprise uric acid or a salt or ester thereof and at least one stabilizer selected from the group consisting of: ascorbic acid or a salt or ester thereof; ethanol; acetone; 6-hydroxy-2,5,7,8-tetramethylchroman-2-carboxylic acid; 6-hydroxy-2,5,7,8-tetraniethylchroman-2-carboxylic acid; albumin; sucrose; glycylglycine; L-camosine; N-acetyl cysteine; silymarin; diosmin; lipoic acid; hydroquinonesulfonic acid; sodium formaldehyde sulfoxylate; and gallic acid or a derivative thereof.

39. The method according to claim 4, wherein said at least one stabilizer is a dipeptide stabilizer.

40. The method according to claim 4, wherein said non-aqueous solvent is selected from the group consisting of glycerol, DMSO, ethanol, acetone, PPG and combinations thereof.

41. The method according to claim 1 or 2, wherein the recovery of the desired activity of the biological material after sterilization by irradiation is at least about 50% of the pre-irradiation value.

42. A method for prophylaxis or treatment of a condition or disease in a mammal comprising administering to a mammal in need thereof an effective amount of a biological material made according to a method of claim 1 or 2.

43. The method according to claim 4, wherein said biological material is tissue and said at least one stabilizer is introduced into said tissue by a method comprising: (a) soaking said tissue in a solution containing said at least one stabilizer; (b) applying a gas containing said at least one stabilizer to said tissue; (c) injecting said at least one stabilizer into said tissue; (d) injecting a solution containing said at least one stabilizer into said tissue; (e) placing said tissue under reduced pressure and contacting said tissue with a gas or solution containing said at least one stabilizer; and (f) dehydrating said tissue and rehydrating said tissue with a solution containing said at least one stabilizer.

44. A biological material made according to a method of claim 1 or 2.

45. The biological material according to claim 44, wherein said biological material is selected from the group consisting of dextrose, urokinase, thrombin, purified protein fraction, blood, blood cells, alpha-1 proteinase inhibitor, digestive enzymes, blood proteins and tissue.

46. The biological material according to claim 45, wherein said tissue is selected from the group consisting of tendons, nerves, bone, teeth, bone marrow, skin grafts, cartilage, corneas, arteries, veins, heart valves, ligaments and demineralized bone matrix.

47. The biological material according to claim 45, wherein said digestive enzymes are selected from the group consisting of galactosidases and sulfatases.

48. The biological material according to claim 45, wherein said blood proteins are selected from the group consisting of albumin, Factor VIII, Factor VII, Factor IV, fibrinogen, monoclonal immunoglobulins and polyclonal immunoglobulins.

49. The biological material according to claim 44, wherein said biological material is milk.

50. The biological material according to claim 44, wherein said biological material is serum or plasma.

* * * * *